US008017754B2

(12) United States Patent
Wicker et al.

(10) Patent No.: US 8,017,754 B2
(45) Date of Patent: Sep. 13, 2011

(54) ATTENUATED VIRUS STRAINS AND USES THEREOF

(75) Inventors: Jason A. Wicker, Galveston, TX (US); Melissa C. Whiteman, Rochester, NY (US); Michael D. T. Barrett, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 421 days.

(21) Appl. No.: 11/995,920

(22) PCT Filed: Jul. 14, 2006

(86) PCT No.: PCT/US2006/027565

§ 371 (c)(1), (2), (4) Date: Dec. 5, 2008

(87) PCT Pub. No.: WO2007/015783

PCT Pub. Date: Feb. 8, 2007

(65) Prior Publication Data

US 2009/0117149 A1 May 7, 2009

Related U.S. Application Data

(60) Provisional application No. 60/701,765, filed on Jul. 22, 2005.

(51) Int. Cl.
*A61K 39/12* (2006.01)

(52) U.S. Cl. ................ 536/23.72; 424/218.1; 424/199.1

(58) Field of Classification Search ........................ None
See application file for complete search history.

(56) References Cited

U.S. PATENT DOCUMENTS

| | | | | |
|---|---|---|---|---|
| 4,579,945 | A | 4/1986 | Schwartzman et al. | 536/127 |
| 4,877,611 | A | 10/1989 | Cantrell | 424/277.1 |
| 4,950,645 | A | 8/1990 | Vosika et al. | 424/279.1 |
| 6,696,281 | B1 | 2/2004 | Chambers et al. | 435/235.1 |
| 6,878,372 | B2 | 4/2005 | Monath et al. | 424/93.1 |
| 2005/0053624 | A1 | 3/2005 | Arroyo et al. | 424/218.1 |

FOREIGN PATENT DOCUMENTS

WO WO 03/092592 11/2003

OTHER PUBLICATIONS

Wicker, J., et al., Virology, Jun. 5, 2006, 349(2):245-253.*

Arroyo et al., "ChimeriVax-West Nile virus live-attenuated vaccine: preclinical evaluation of safety, immunogenicity, and efficacy," *J. Virol.*, 78(22):12497-12507, 2004.

Beasley et al., "Envelope protein glycosylation status influences mouse neuroinvasion phenotype of genetic lineage 1 West Nile virus strains," *J. Virol.*, 79:8339-8347, 2005.

Beasley et al., "Genome sequence and attenuating mutation in West Nile virus isolate from Mexico," *Emerging Infect. Dis.*, Internet Publication, Dec. 2004.

Beasley et al., "Mouse neuroinvasive phenotype of West Nile virus strains varies depending upon virus genotype," *Virology*, 296:17-23, 2002.

Blaney Jr. et al., "Mutations which enhance the replication of dengue virus type 4 and an antigenic chimeric dengue virus type 2/4 vaccine candidate in Vero cells," *Vaccine*, 21:4317-4327, 2003.

Blitvich et al., "A novel complex formed between the flavivirus E and NS1 proteins: analysis of its structure and function," *Arch. Virol.*, 140:145-156, 1995.

Blitvich et al., "Determination of the intramolecular disulfide bond arrangement and biochemical identification of the glycosylation sites of the nonstructural protein NS1 of Murray Valley encephalitis virus," *J. Gen. Virol.*, 82:2251-2256, 2001.

Blitvich et al., "Identification and analysis of truncated and elongated species of the flavivirus NS1 protein," *Virus Res.*, 60:67-79, 1999.

Chang et al., "Facilitation of cell adhesion by immobilized dengue viral nonstructural protein 1 (NS1): arginine-glycine-aspartic acid structural mimicry within the dengue viral NS1 antigen," *J. Infect. Dis.*, 186:743-751, 2002.

Crabtree et al., "Deglycosylation of the NS1 protein of dengue 2 virus, strain 16681: construction and characterization of mutant viruses," *Arch. Virol.*, 150:771-786, 2005.

Davis et al., "Emergence of attenuated West Nile virus variants in Texas, 2003," *Virology*, 330:342-350, 2004.

Estrada-Franco, "West Nile Virus in Mexico: Evidence of Widespread Circulation since Jul. 2002," *Emerging Infect. Dis.*, 9(12):1604-1607, 2003.

Falconar, "The dengue virus nonstructural-1 protein (NS1) generates antibodies to common epitopes on human blood clotting, integrin/adhesin proteins and binds to human endothelial cells: potential implications in haemorrhagic fever pathogenesis," *Arch. Virol.*, 142(5):897-916, 1997.

Falgout and Markoff, "Evidence that flavivirus NS1-NS2A cleavage is mediated by a membrane-bound host protease in the endoplasmic reticulum," *J. Virol.*, 69(11):7232-7243, 1995.

Flamand et al., "Dengue virus type 1 nonstructural glycoprotein NS1 is secreted from mammalian cells as a soluble hexamer in a glycosylation-dependent fashion," *J. Virol.*, 73:6104-6110, 1999.

Hahn et al., "Comparison of the virulent Asibi strain of yellow fever virus with the 17D vaccine strain derived from it," *Proc. Natl. Acad. Sci*. USA, 84:2019-2023, 1987. Hall et al., "Loss of dimerisation of the nonstructural protein NS1 of Kunjin virus delays viral replication and reduces virulence in mice, but still allows secretion of NS1," *Virology*, 264:66-75, 1999.

Hall et al., "Protective immune responses to the E and NS1 proteins of Murray Valley encephalitis virus in hybrids of flavivirus-resistant mice," *J. Gen. Virol.*, 77:1287-1294, 1996.

Hanley et al., "A trade-off in replication in mosquito versus mammalian systems conferred by a point mutation in the NS4B protein of dengue virus type 4," *Virology*, 312:222-232, 2003.

Lindenbach and Rice, "trans-Complementation of yellow fever virus NS1 reveals a role in early RNA replication," *J. Virol.*, 71:9608-9617, 1997.

Lindenbach and Rice, "Flaviviridae: The Viruses and Their Replication," In: Fields Virology, $4^{th}$ Edition, 991-1041, 2001.

(Continued)

*Primary Examiner* — Stacy B Chen

(74) *Attorney, Agent, or Firm* — Fulbright & Jaworski L.L.P.

(57) ABSTRACT

Methods and compositions concerning mutant flaviviruses with reduced virulence. In some embodiments the invention concerns nucleotide sequences that encode mutant flaviviral proteins. Viruses comprising mutant NS1 and NS4B genes display reduced virulence are provided. In further aspects of the invention, flavivirus vaccine compositions such as West Nile virus vaccines are provided. In another embodiment the invention provides methods for vaccination against flavivirus infection.

24 Claims, 10 Drawing Sheets

OTHER PUBLICATIONS

Lundin et al., "Topology of the membrane-associated hepatitis C virus protein NS4B," *J. Virol.*, 77:5428-5438, 2003.

Mackenzie et al., "Immunolocalization of the dengue virus nonstructural glycoprotein NS1 suggests a role in viral RNA replication," *Virology*, 220:232-240, 1996.

McArthur et al., "Molecular characterization of a hamster viscerotropic strain of yellow fever virus," *J. Virol.*, 77:1462-1468, 2003.

Monath et al., "West Nile virus vaccine," *Curr. Drug Targets Infect. Disord.*, 1:37-50, 2001.

Munoz-Jordan et al., "Inhibition of alpha/beta interferon signaling by the NS4B protein of flaviviruses," *Journal of Virology*, 79(13):8004-8013, 2005.

Munoz-Jordan et al., "Inhibition of interferon signaling by dengue virus," *PNAS*, 100(24):14333-14338, 2003.

Muylaert et al., "Mutagenesis of the N-linked glycosylation sites of the yellow fever virus NS1 protein: effects on virus replication and mouse neurovirulence," *Virology*, 222:159-168, 1996.

Nestorowicz et al., "Mutagenesis of the yellow fever virus NS2A/2B cleavage site: effects on proteolytic processing, viral replication, and evidence for alternative processing of the NS2A protein," *Virology*, 199:114-123, 1994.

Ni et al., "Molecular basis of attenuation of neurovirulence of wild-type Japanese encephalitis virus strain SA14," *J. Gen. Virol.*, 76:409-413, 1995.

PCT International Preliminary Report on Patentability, issued in International Application No. PCT/US2006/027565, dated Dec. 7, 2007.

PCT International Search Report and Written Opinion, issued in International Application No. PCT/US2006/027565, dated Jun. 13, 2007.

PCT Invitation to Pay Additional Fees, issued in International Application No. PCT/US2006/027565, dated Mar. 12, 2007.

Pletnev et al., "Chimeric tick-borne encephalitis and dengue type 4 viruses: effects of mutations on neurovirulence in mice," *J. Virol.*, 67(8):4956-4963, 1993.

Pletnev et al., "West Nile virus/dengue type 4 virus chimeras that are reduced in neurovirulence and peripheral virulence without loss of immunogenicity or protective efficacy," *Proc. Natl. Acad. Sci. USA*, 99:3036-3041, 2002.

Pletnev, "Infectious cDNA clone of attenuated Langat tick-borne flavivirus (strain E5) and a 3' deletion mutant constructed from it exhibit decreased neuroinvasiveness in immunodeficient mice," *Virology*, 282:288-300, 2001.

Pryor and Wright, "Glycosylation mutants of dengue virus NS1 protein," *J. Gen. Virol.*, 75:1183-1187, 1994.

Pryor and Wright, "The effects of site-directed mutagenesis on the dimerization and secretion of the NS1 protein specified by dengue virus," *Virology*, 194:769-780, 1993.

Pryor et al., "Growth restriction of dengue virus type 2 by site-specific mutagenesis of virus-encoded glycoproteins," *J. Gen. Virol.*, 79:2631-2639, 1998.

Wang et al., "Comparison of the genomes of the wild-type French viscerotropic strain of yellow fever virus with its vaccine derivative French neurotropic vaccine," *J. Gen. Virol.*, 76:2749-2755, 1995.

Westaway et al., "Proteins C and NS4B of the flavivirus Kunjin translocate independently into the nucleus," *Virology*, 234:31-41, 1997.

Westaway et al., "Ultrastructure of Kunjin virus-infected cells: colocalization of NS1 and NS3 with double-stranded RNA, and of NS2B with NS3, in virus-induced membrane structures," *J. Virol.*, 71:6650-6661, 1997.

Yamshchikov et al., "An attenuated West Nile prototype virus is highly immunogenic and protects against the deadly NY99 strain: a candidate for live WN vaccine development," *Virology*, 330:304-312, 2004.

\* cited by examiner

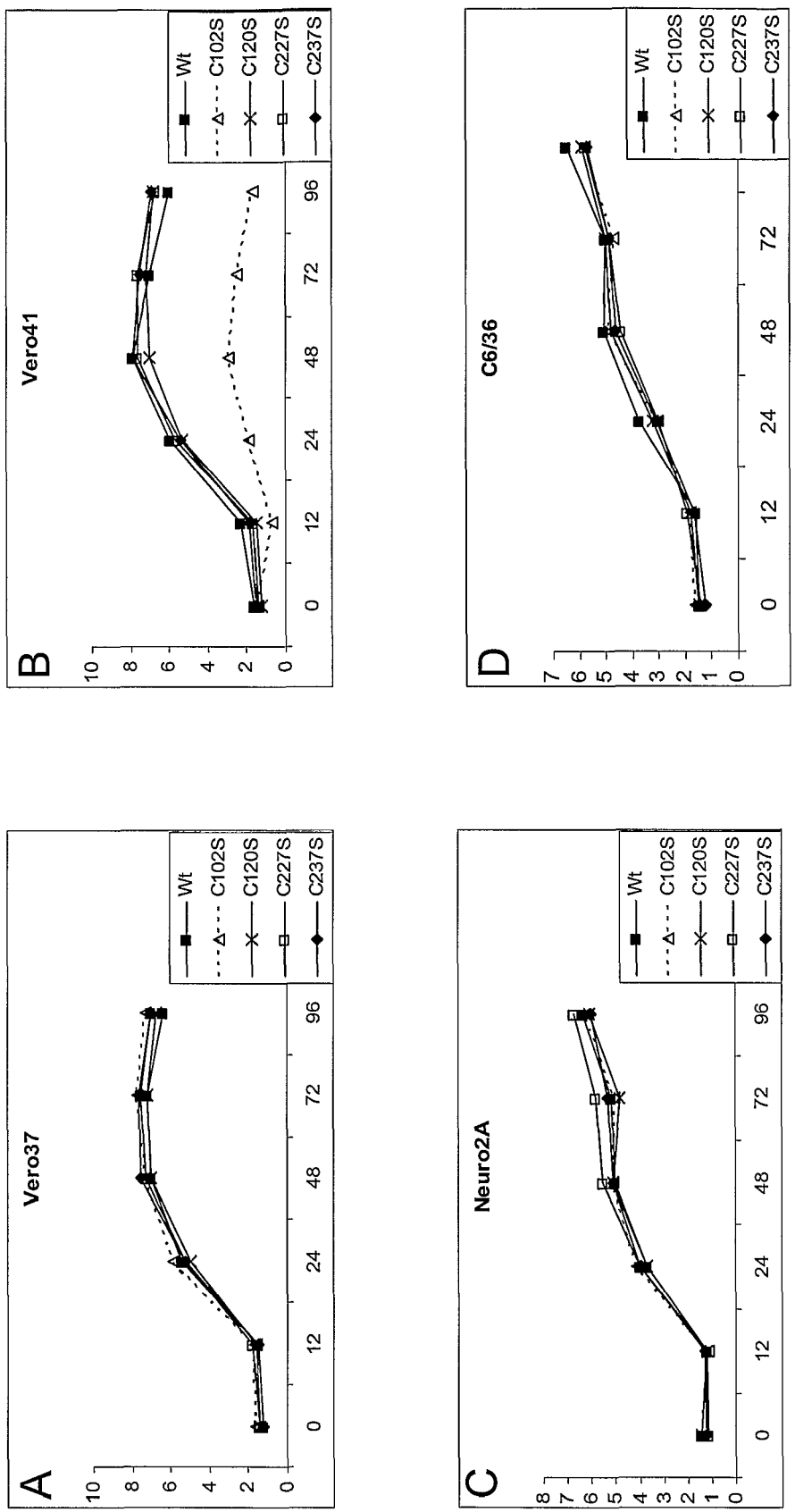
FIG. 2A-D

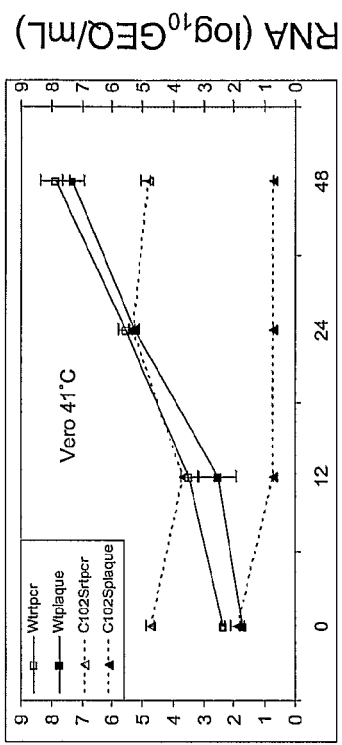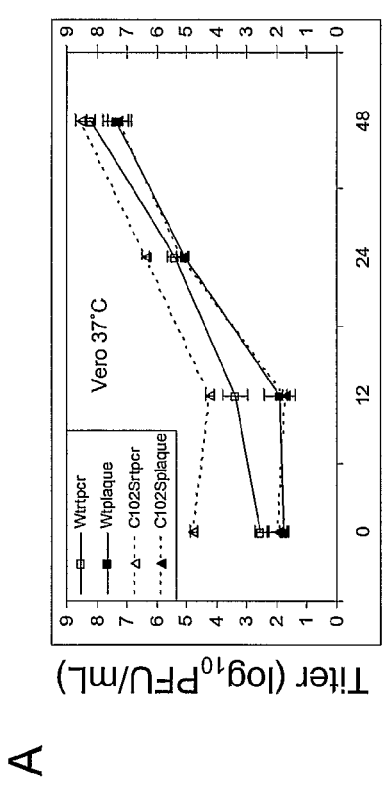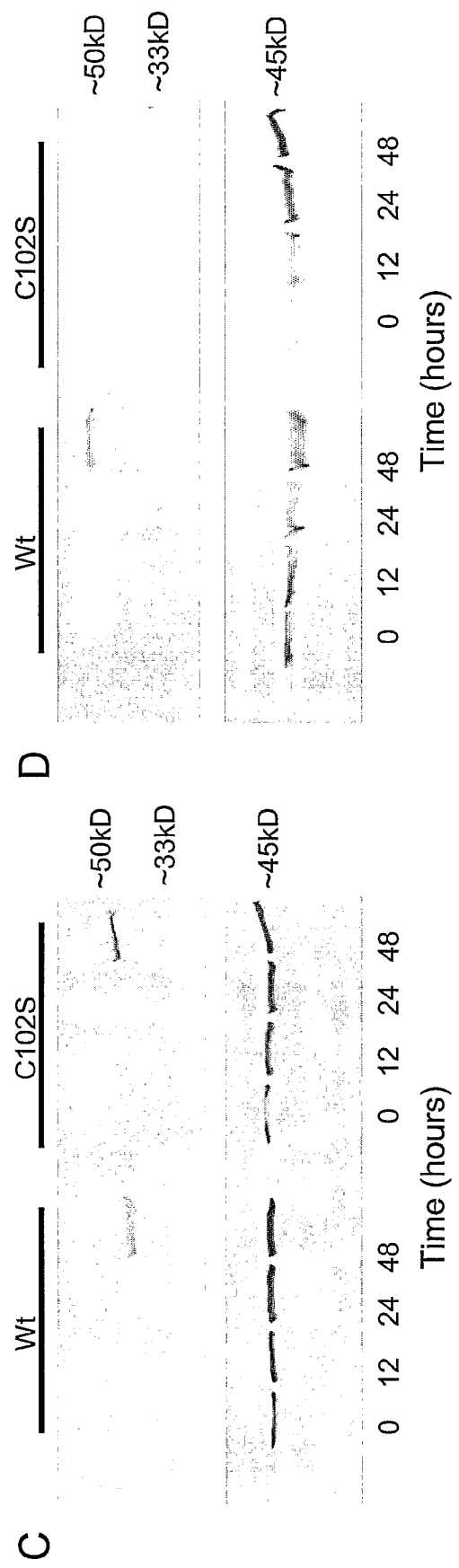
FIG. 3A-D

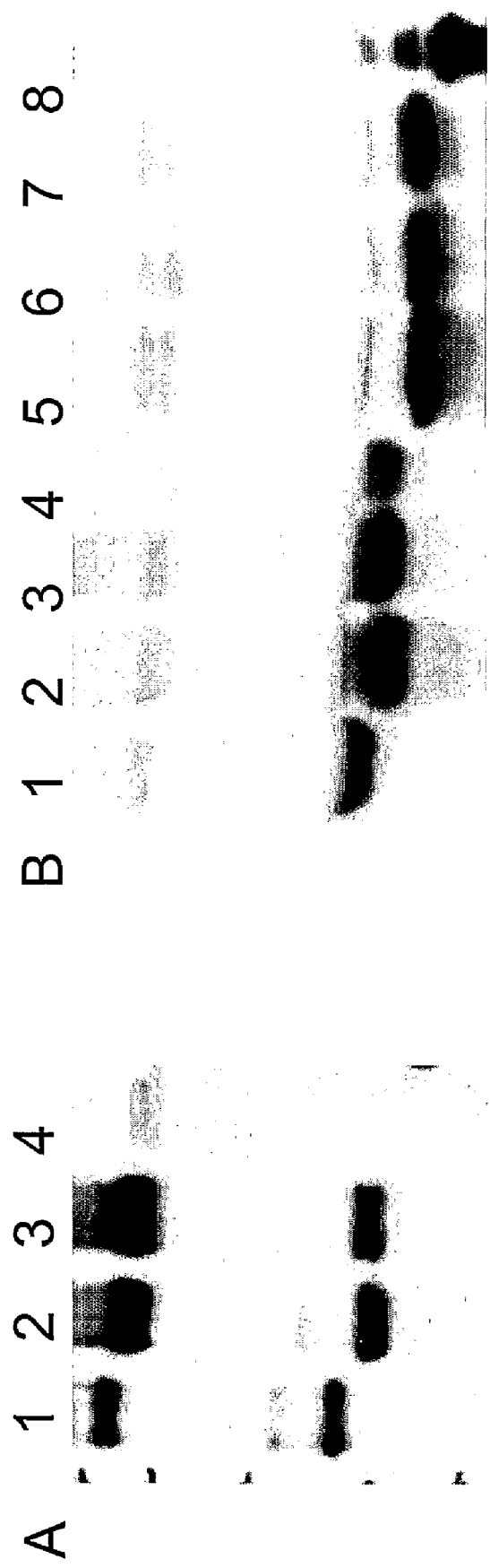
FIG. 4A-B

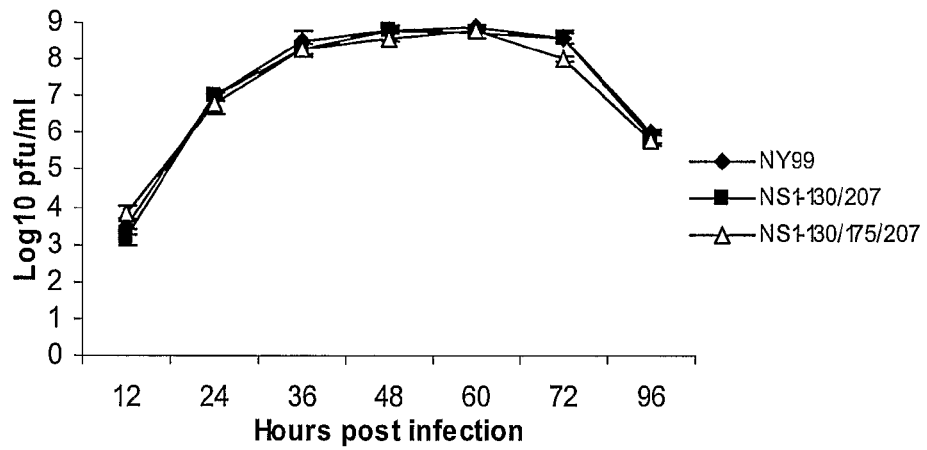
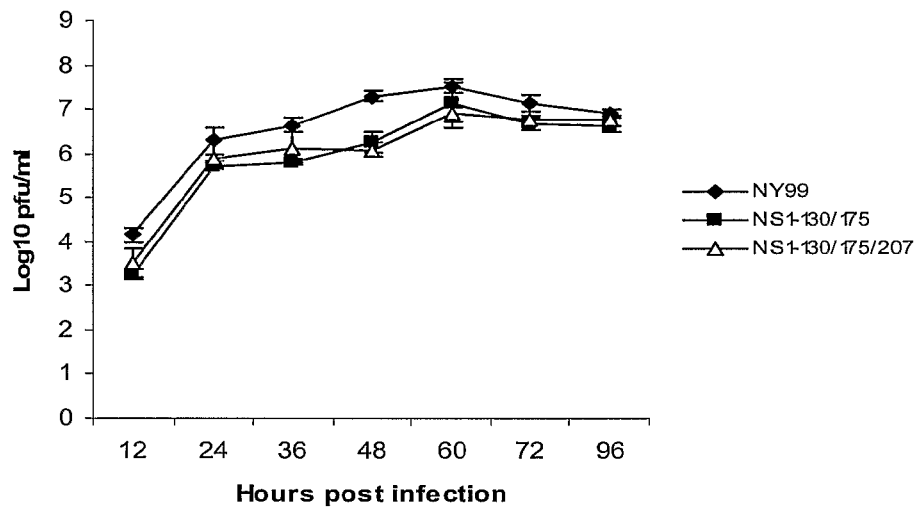
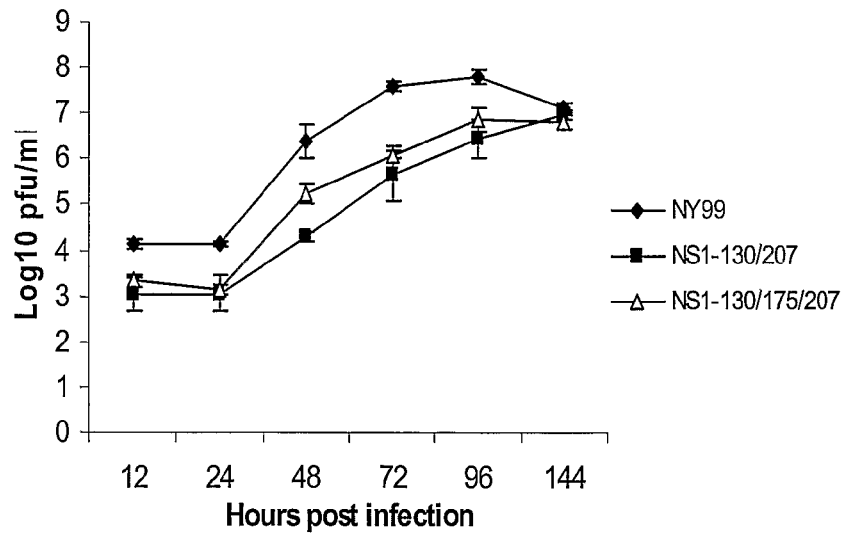
FIG. 5A-C

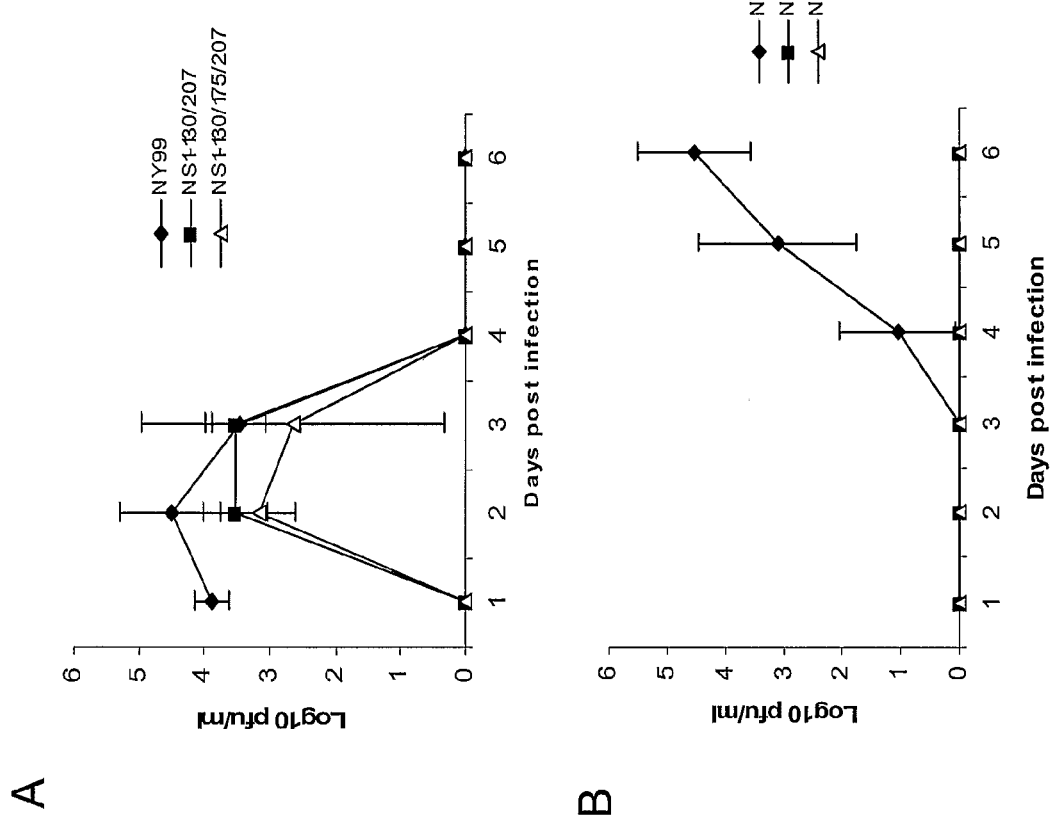
FIG. 6A-B

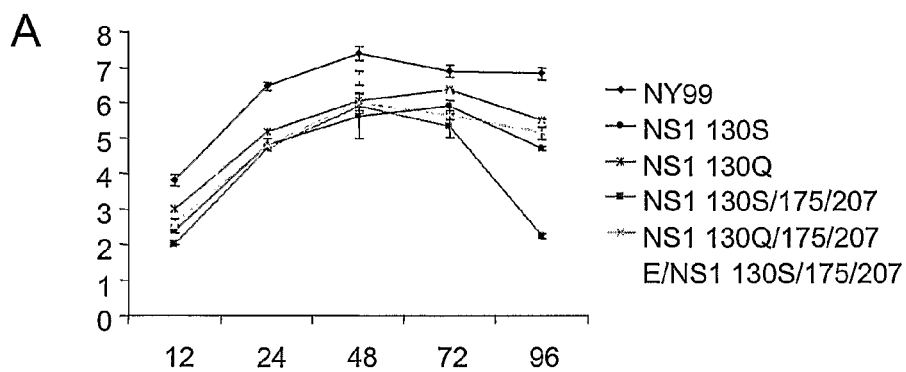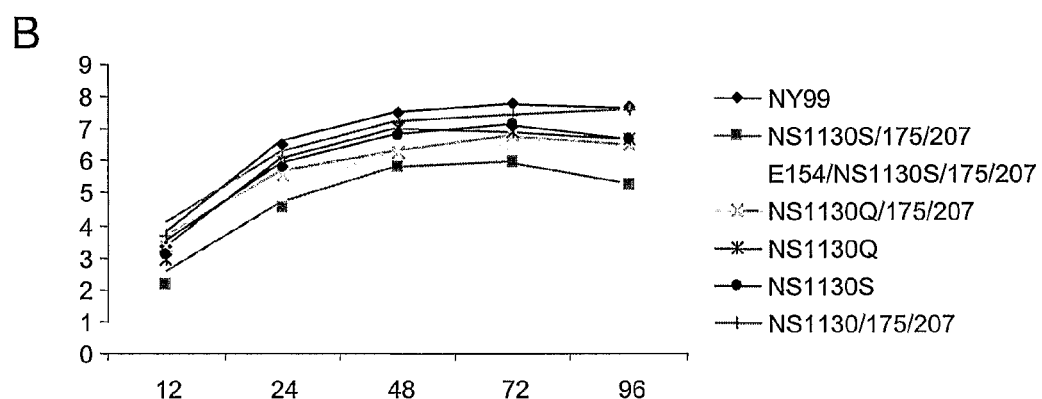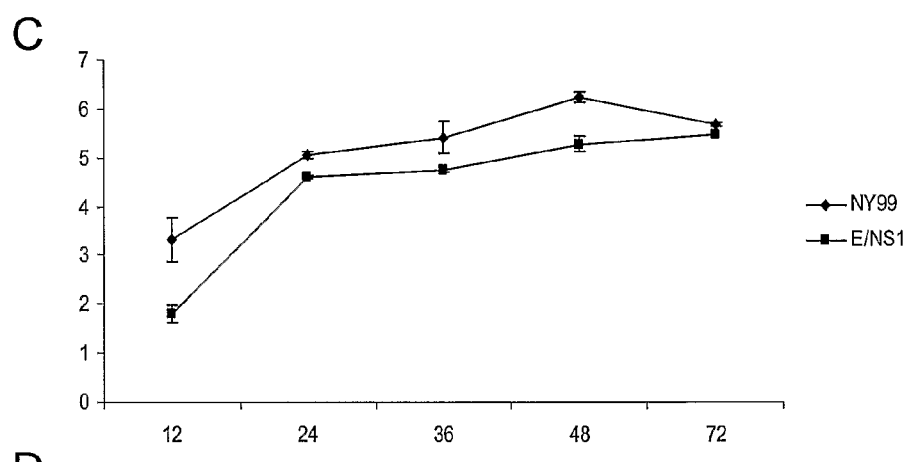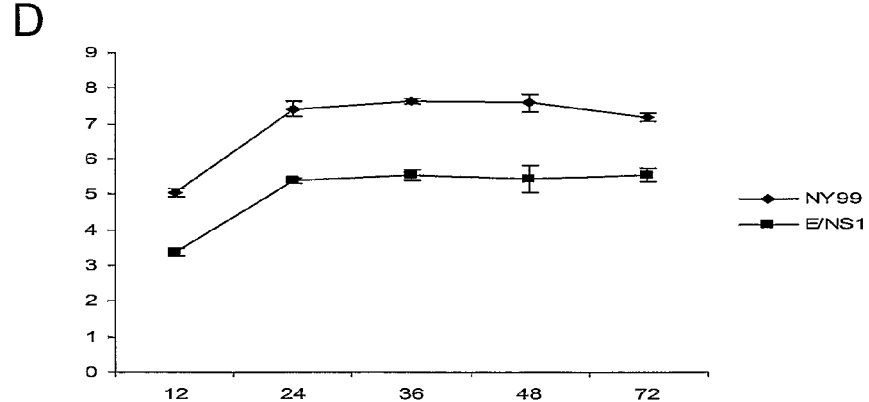
FIG. 7A-D

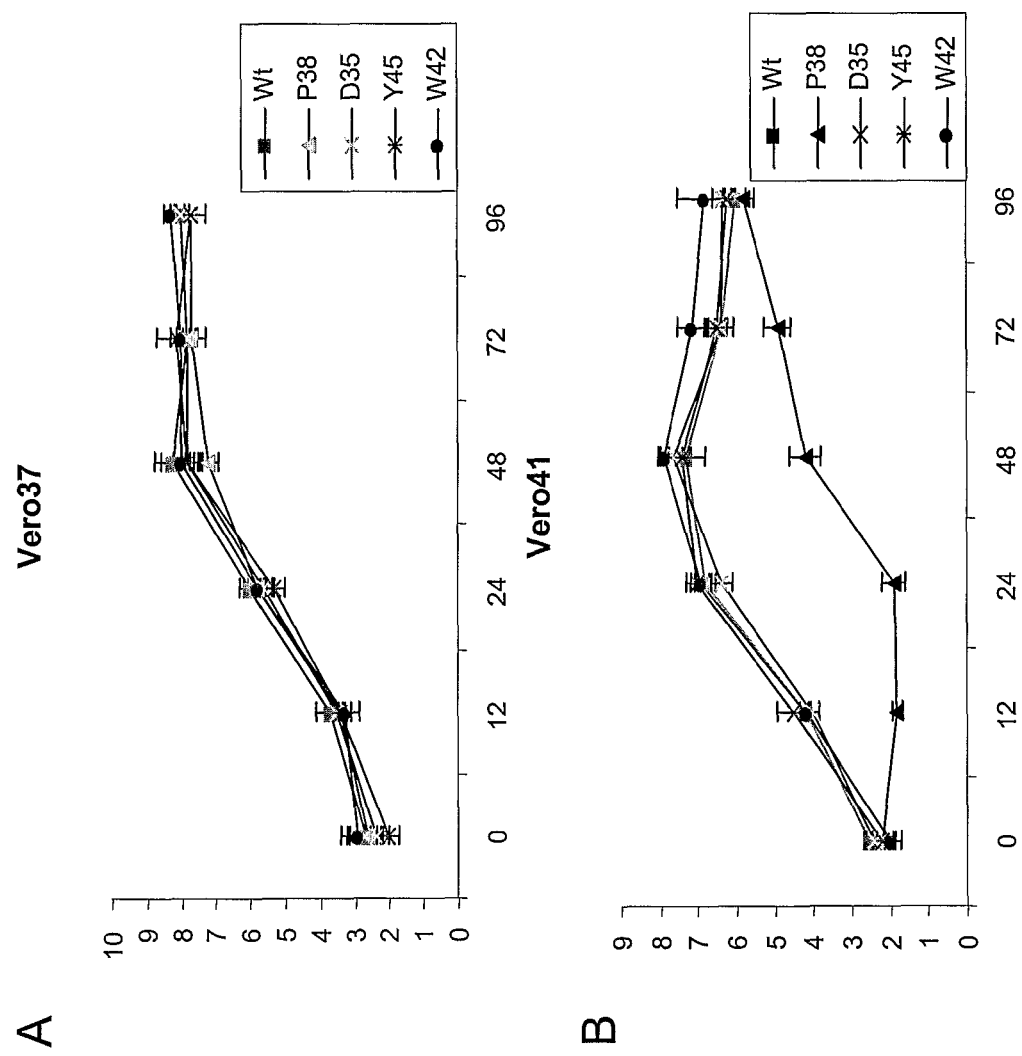
FIG. 8A-B

SEQUENCE LISTING

<160> NUMBER OF SEQ ID NOS: 22

<210> SEQ ID NO 1
<211> LENGTH: 11029
<212> TYPE: DNA
<213> ORGANISM: West Nile virus
<220> FEATURE:
<221> NAME/KEY: CDS
<222> LOCATION: (97)..(10398)

<400> SEQUENCE: 1

```
agtagttcgc ctgtgtgagc tgacaaactt agtagtgttt gtgaggatta acaacaatta         60
acacagtgcg agctgtttct tagcacgaag atctcg atg tct aag aaa cca gga          114
                                        Met Ser Lys Lys Pro Gly
                                         1               5 ggg ccc ggc aag agc cgg gct gtc aat atg cta aaa cgc gga atg ccc          162
Gly Pro Gly Lys Ser Arg Ala Val Asn Met Leu Lys Arg Gly Met Pro
            10                  15                  20 cgc gtg ttg tcc ttg att gga ctg aag agg gct atg ttg agc ctg atc          210
Arg Val Leu Ser Leu Ile Gly Leu Lys Arg Ala Met Leu Ser Leu Ile
        25                  30                  35 gac ggc aag ggg cca ata cga ttt gtg ttg gct ctc ttg gcg ttc ttc          258
Asp Gly Lys Gly Pro Ile Arg Phe Val Leu Ala Leu Leu Ala Phe Phe
    40                  45                  50 agg ttc aca gca att gct ccg acc cga gca gtg ctg gat cga tgg aga          306
Arg Phe Thr Ala Ile Ala Pro Thr Arg Ala Val Leu Asp Arg Trp Arg
55                  60                  65                  70 ggt gtg aac aaa caa aca gcg atg aaa cac ctt ctg agt ttt aag aag          354
Gly Val Asn Lys Gln Thr Ala Met Lys His Leu Leu Ser Phe Lys Lys
                75                  80                  85 gaa cta ggg acc ttg acc agt gct atc aat cgg cgg agc tca aaa caa          402
Glu Leu Gly Thr Leu Thr Ser Ala Ile Asn Arg Arg Ser Ser Lys Gln
            90                  95                 100 aag aaa aga gga gga aag acc gga att gca gtc atg att ggc ctg atc          450
Lys Lys Arg Gly Gly Lys Thr Gly Ile Ala Val Met Ile Gly Leu Ile
        105                 110                 115 gcc agc gta gga gca gtt acc ctc tct aac ttc caa ggg aag gtg atg          498
Ala Ser Val Gly Ala Val Thr Leu Ser Asn Phe Gln Gly Lys Val Met
    120                 125                 130 atg acg gta aat gct act gac gtc aca gat gtc atc acg att cca aca          546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac          594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt          642
Met Cys Asp Asp Thr Ile Thr Tyr Glu Cys Pro Val Leu Ser Ala Gly
            170                 175                 180 aat gat cca gaa gac atc gac tgt tgg tgc aca aag tca gca gtc tac          690
Asn Asp Pro Glu Asp Ile Asp Cys Trp Cys Thr Lys Ser Ala Val Tyr
        185                 190                 195 gtc agg tat gga aga tgc acc aag aca cgc cac tca aga cgc agt cgg          738
Val Arg Tyr Gly Arg Cys Thr Lys Thr Arg His Ser Arg Arg Ser Arg
    200                 205                 210 agg tca ctg aca gtg cag aca cac gga gaa agc act cta gcg aac aag          786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa          834
Lys Gly Ala Trp Met Asp Ser Thr Lys Ala Thr Arg Tyr Leu Val Lys
                235                 240                 245
```

| | | |
|---|---|---|
| aca gaa tca tgg atc ttg agg aac cct gga tat gcc ctg gtg gca gcc<br>Thr Glu Ser Trp Ile Leu Arg Asn Pro Gly Tyr Ala Leu Val Ala Ala<br>250 255 260 | | 882 |
| gtc att ggt tgg atg ctt ggg agc aac acc atg cag aga gtt gtg ttt<br>Val Ile Gly Trp Met Leu Gly Ser Asn Thr Met Gln Arg Val Val Phe<br>265 270 275 | | 930 |
| gtc gtg cta ttg ctt ttg gtg gcc cca gct tac agc ttc aac tgc ctt<br>Val Val Leu Leu Leu Leu Val Ala Pro Ala Tyr Ser Phe Asn Cys Leu<br>280 285 290 | | 978 |
| gga atg agc aac aga gac ttc ttg gaa gga gtg tct gga gca aca tgg<br>Gly Met Ser Asn Arg Asp Phe Leu Glu Gly Val Ser Gly Ala Thr Trp<br>295 300 305 310 | | 1026 |
| gtg gat ttg gtt ctc gaa ggc gac agc tgc gtg act atc atg tct aag<br>Val Asp Leu Val Leu Glu Gly Asp Ser Cys Val Thr Ile Met Ser Lys<br>315 320 325 | | 1074 |
| gac aag cct acc atc gat gtg aag atg atg aat atg gag gcg gcc aac<br>Asp Lys Pro Thr Ile Asp Val Lys Met Met Asn Met Glu Ala Ala Asn<br>330 335 340 | | 1122 |
| ctg gca gag gtc cgc agt tat tgc tat ttg gct acc gtc agc gat ctc<br>Leu Ala Glu Val Arg Ser Tyr Cys Tyr Leu Ala Thr Val Ser Asp Leu<br>345 350 355 | | 1170 |
| tcc acc aaa gct gcg tgc ccg acc atg gga gaa gct cac aat gac aaa<br>Ser Thr Lys Ala Ala Cys Pro Thr Met Gly Glu Ala His Asn Asp Lys<br>360 365 370 | | 1218 |
| cgt gct gac cca gct ttt gtg tgc aga caa gga gtg gtg gac agg ggc<br>Arg Ala Asp Pro Ala Phe Val Cys Arg Gln Gly Val Val Asp Arg Gly<br>375 380 385 390 | | 1266 |
| tgg ggc aac ggc tgc gga cta ttt ggc aaa gga agc att gac aca tgc<br>Trp Gly Asn Gly Cys Gly Leu Phe Gly Lys Gly Ser Ile Asp Thr Cys<br>395 400 405 | | 1314 |
| gcc aaa ttt gcc tgc tct acc aag gca ata gga aga acc atc ttg aaa<br>Ala Lys Phe Ala Cys Ser Thr Lys Ala Ile Gly Arg Thr Ile Leu Lys<br>410 415 420 | | 1362 |
| gag aat atc aag tac gaa gtg gcc att ttt gtc cat gga cca act act<br>Glu Asn Ile Lys Tyr Glu Val Ala Ile Phe Val His Gly Pro Thr Thr<br>425 430 435 | | 1410 |
| gtg gag tcg cac gga aac tac tcc aca cag gtt gga gcc act cag gca<br>Val Glu Ser His Gly Asn Tyr Ser Thr Gln Val Gly Ala Thr Gln Ala<br>440 445 450 | | 1458 |
| ggg aga ttc agc atc act cct gcg gcg cct tca tac aca cta aag ctt<br>Gly Arg Phe Ser Ile Thr Pro Ala Ala Pro Ser Tyr Thr Leu Lys Leu<br>455 460 465 470 | | 1506 |
| gga gaa tat gga gag gtg aca gtg gac tgt gaa cca cgg tca ggg att<br>Gly Glu Tyr Gly Glu Val Thr Val Asp Cys Glu Pro Arg Ser Gly Ile<br>475 480 485 | | 1554 |
| gac acc aat gca tac tac gtg atg act gtt gga aca aag acg ttc ttg<br>Asp Thr Asn Ala Tyr Tyr Val Met Thr Val Gly Thr Lys Thr Phe Leu<br>490 495 500 | | 1602 |
| gtc cat cgt gag tgg ttc atg gac ctc aac ctc cct tgg agc agt gct<br>Val His Arg Glu Trp Phe Met Asp Leu Asn Leu Pro Trp Ser Ser Ala<br>505 510 515 | | 1650 |
| gga agt act gtg tgg agg aac aga gag acg tta atg gag ttt gag gaa<br>Gly Ser Thr Val Trp Arg Asn Arg Glu Thr Leu Met Glu Phe Glu Glu<br>520 525 530 | | 1698 |
| cca cac gcc acg aag cag tct gtg ata gca ttg ggc tca caa gag gga<br>Pro His Ala Thr Lys Gln Ser Val Ile Ala Leu Gly Ser Gln Glu Gly<br>535 540 545 550 | | 1746 |
| gct ctg cat caa gct ttg gct gga gcc att cct gtg gaa ttt tca agc<br>Ala Leu His Gln Ala Leu Ala Gly Ala Ile Pro Val Glu Phe Ser Ser<br>555 560 565 | | 1794 |

| | | | | | | | | | | | | | | | | |
|---|---|---|---|---|---|---|---|---|---|---|---|---|---|---|---|---|
| aac | act | gtc | aag | ttg | acg | tcg | ggt | cat | ttg | aag | tgt | aga | gtg | aag | atg | 1842 |
| Asn | Thr | Val | Lys | Leu | Thr | Ser | Gly | His | Leu | Lys | Cys | Arg | Val | Lys | Met | |
| | | | 570 | | | | | 575 | | | | | 580 | | | |
| gaa | aaa | ttg | cag | ttg | aag | gga | aca | acc | tat | ggc | gtc | tgt | tca | aag | gct | 1890 |
| Glu | Lys | Leu | Gln | Leu | Lys | Gly | Thr | Thr | Tyr | Gly | Val | Cys | Ser | Lys | Ala | |
| | | 585 | | | | | 590 | | | | | 595 | | | | |
| ttc | aag | ttt | ctt | ggg | act | ccc | gca | gac | aca | ggt | cac | ggc | act | gtg | gtg | 1938 |
| Phe | Lys | Phe | Leu | Gly | Thr | Pro | Ala | Asp | Thr | Gly | His | Gly | Thr | Val | Val | |
| | 600 | | | | | 605 | | | | | 610 | | | | | |
| ttg | gaa | ttg | cag | tac | act | ggc | acg | gat | gga | cct | tgc | aaa | gtt | cct | atc | 1986 |
| Leu | Glu | Leu | Gln | Tyr | Thr | Gly | Thr | Asp | Gly | Pro | Cys | Lys | Val | Pro | Ile | |
| 615 | | | | 620 | | | | | 625 | | | | | 630 | | |
| tcg | tca | gtg | gct | tca | ttg | aac | gac | cta | acg | cca | gtg | ggc | aga | ttg | gtc | 2034 |
| Ser | Ser | Val | Ala | Ser | Leu | Asn | Asp | Leu | Thr | Pro | Val | Gly | Arg | Leu | Val | |
| | | | | 635 | | | | | 640 | | | | | 645 | | |
| act | gtc | aac | cct | ttt | gtt | tca | gtg | gcc | acg | gcc | aac | gct | aag | gtc | ctg | 2082 |
| Thr | Val | Asn | Pro | Phe | Val | Ser | Val | Ala | Thr | Ala | Asn | Ala | Lys | Val | Leu | |
| | | | 650 | | | | | 655 | | | | | 660 | | | |
| att | gaa | ttg | gaa | cca | ccc | ttt | gga | gac | tca | tac | ata | gtg | gtg | ggc | aga | 2130 |
| Ile | Glu | Leu | Glu | Pro | Pro | Phe | Gly | Asp | Ser | Tyr | Ile | Val | Val | Gly | Arg | |
| | | 665 | | | | | 670 | | | | | 675 | | | | |
| gga | gaa | caa | cag | atc | aat | cac | cat | tgg | cac | aag | tct | gga | agc | agc | att | 2178 |
| Gly | Glu | Gln | Gln | Ile | Asn | His | His | Trp | His | Lys | Ser | Gly | Ser | Ser | Ile | |
| | 680 | | | | | 685 | | | | | 690 | | | | | |
| ggc | aaa | gcc | ttt | aca | acc | acc | ctc | aaa | gga | gcg | cag | aga | cta | gcc | gct | 2226 |
| Gly | Lys | Ala | Phe | Thr | Thr | Thr | Leu | Lys | Gly | Ala | Gln | Arg | Leu | Ala | Ala | |
| 695 | | | | 700 | | | | | 705 | | | | | 710 | | |
| cta | gga | gac | aca | gct | tgg | gac | ttt | gga | tca | gtt | gga | ggg | gtg | ttc | acc | 2274 |
| Leu | Gly | Asp | Thr | Ala | Trp | Asp | Phe | Gly | Ser | Val | Gly | Gly | Val | Phe | Thr | |
| | | | | 715 | | | | | 720 | | | | | 725 | | |
| tca | gtt | ggg | aag | gct | gtc | cat | caa | gtg | ttc | gga | gga | gca | ttc | cgc | tca | 2322 |
| Ser | Val | Gly | Lys | Ala | Val | His | Gln | Val | Phe | Gly | Gly | Ala | Phe | Arg | Ser | |
| | | 730 | | | | | 735 | | | | | 740 | | | | |
| ctg | ttc | gga | ggc | atg | tcc | tgg | ata | acg | caa | gga | ttg | ctg | ggg | gct | ctc | 2370 |
| Leu | Phe | Gly | Gly | Met | Ser | Trp | Ile | Thr | Gln | Gly | Leu | Leu | Gly | Ala | Leu | |
| | 745 | | | | | 750 | | | | | 755 | | | | | |
| ctg | ttg | tgg | atg | ggc | atc | aat | gct | cgt | gat | agg | tcc | ata | gct | ctc | acg | 2418 |
| Leu | Leu | Trp | Met | Gly | Ile | Asn | Ala | Arg | Asp | Arg | Ser | Ile | Ala | Leu | Thr | |
| 760 | | | | 765 | | | | | 770 | | | | | | | |
| ttt | ctc | gca | gtt | gga | gga | gtt | ctg | ctc | ttc | ctc | tcc | gtg | aac | gtg | cac | 2466 |
| Phe | Leu | Ala | Val | Gly | Gly | Val | Leu | Leu | Phe | Leu | Ser | Val | Asn | Val | His | |
| 775 | | | | 780 | | | | | 785 | | | | | 790 | | |
| gct | gac | act | ggg | tgt | gcc | ata | gac | atc | agc | cgg | caa | gag | ctg | aga | tgt | 2514 |
| Ala | Asp | Thr | Gly | Cys | Ala | Ile | Asp | Ile | Ser | Arg | Gln | Glu | Leu | Arg | Cys | |
| | | | 795 | | | | | 800 | | | | | 805 | | | |
| gga | agt | gga | gtg | ttc | ata | cac | aat | gat | gtg | gag | gct | tgg | atg | gac | cgg | 2562 |
| Gly | Ser | Gly | Val | Phe | Ile | His | Asn | Asp | Val | Glu | Ala | Trp | Met | Asp | Arg | |
| | | 810 | | | | | 815 | | | | | 820 | | | | |
| tac | aag | tat | tac | cct | gaa | acg | cca | caa | ggc | cta | gcc | aag | atc | att | cag | 2610 |
| Tyr | Lys | Tyr | Tyr | Pro | Glu | Thr | Pro | Gln | Gly | Leu | Ala | Lys | Ile | Ile | Gln | |
| | 825 | | | | | 830 | | | | | 835 | | | | | |
| aaa | gct | cat | aag | gaa | gga | gtg | tgc | ggt | cta | cga | tca | gtt | tcc | aga | ctg | 2658 |
| Lys | Ala | His | Lys | Glu | Gly | Val | Cys | Gly | Leu | Arg | Ser | Val | Ser | Arg | Leu | |
| 840 | | | | 845 | | | | | 850 | | | | | | | |
| gag | cat | caa | atg | tgg | gaa | gca | gtg | aag | gac | gag | ctg | aac | act | ctt | ttg | 2706 |
| Glu | His | Gln | Met | Trp | Glu | Ala | Val | Lys | Asp | Glu | Leu | Asn | Thr | Leu | Leu | |
| 855 | | | | 860 | | | | | 865 | | | | | 870 | | |
| aag | gag | aat | ggt | gtg | gac | ctt | agt | gtc | gtg | gtt | gag | aaa | cag | gag | gga | 2754 |
| Lys | Glu | Asn | Gly | Val | Asp | Leu | Ser | Val | Val | Val | Glu | Lys | Gln | Glu | Gly | |
| | | | | 875 | | | | | 880 | | | | | 885 | | |

```
atg tac aag tca gca cct aaa cgc ctc acc gcc acc acg gaa aaa ttg      2802
Met Tyr Lys Ser Ala Pro Lys Arg Leu Thr Ala Thr Thr Glu Lys Leu
            890                 895                 900 gaa att ggc tgg aag gcc tgg gga aag agt att tta ttt gca cca gaa      2850
Glu Ile Gly Trp Lys Ala Trp Gly Lys Ser Ile Leu Phe Ala Pro Glu
            905                 910                 915 ctc gcc aac aac acc ttt gtg gtt gat ggt ccg gag acc aag gaa tgt      2898
Leu Ala Asn Asn Thr Phe Val Val Asp Gly Pro Glu Thr Lys Glu Cys
            920                 925                 930 ccg act cag aat cgc gct tgg aat agc tta gaa gtg gag gat ttt gga      2946
Pro Thr Gln Asn Arg Ala Trp Asn Ser Leu Glu Val Glu Asp Phe Gly
935                 940                 945                 950 ttt ggt ctc acc agc act cgg atg ttc ctg aag gtc aga gag agc aac      2994
Phe Gly Leu Thr Ser Thr Arg Met Phe Leu Lys Val Arg Glu Ser Asn
            955                 960                 965 aca act gaa tgt gac tcg aag atc att gga acg gct gtc aag aac aac      3042
Thr Thr Glu Cys Asp Ser Lys Ile Ile Gly Thr Ala Val Lys Asn Asn
            970                 975                 980 ttg gcg atc cac agt gac ctg tcc tat tgg att gaa agc agg ctc aat      3090
Leu Ala Ile His Ser Asp Leu Ser Tyr Trp Ile Glu Ser Arg Leu Asn
            985                 990                 995 gat acg tgg aag ctt gaa agg gca gtt ctg ggt gaa gtc aaa tca tgt      3138
Asp Thr Trp Lys Leu Glu Arg Ala Val Leu Gly Glu Val Lys Ser Cys
            1000                1005                1010 acg tgg cct gag acg cat acc ttg tgg ggc gat gga atc ctt gag agt      3186
Thr Trp Pro Glu Thr His Thr Leu Trp Gly Asp Gly Ile Leu Glu Ser
1015                1020                1025                1030 gac ttg ata ata cca gtc aca ctg gcg gga cca cga agc aat cac aat      3234
Asp Leu Ile Ile Pro Val Thr Leu Ala Gly Pro Arg Ser Asn His Asn
            1035                1040                1045 cgg aga cct ggg tac aag aca caa aac cag ggc cca tgg gac gaa ggc      3282
Arg Arg Pro Gly Tyr Lys Thr Gln Asn Gln Gly Pro Trp Asp Glu Gly
            1050                1055                1060 cgg gta gag att gac ttc gat tac tgc cca gga act acg gtc acc ctg      3330
Arg Val Glu Ile Asp Phe Asp Tyr Cys Pro Gly Thr Thr Val Thr Leu
            1065                1070                1075 agt gag agc tgc gga cac cgt gga cct gcc act cgc acc acc aca gag      3378
Ser Glu Ser Cys Gly His Arg Gly Pro Ala Thr Arg Thr Thr Thr Glu
            1080                1085                1090 agc gga aag ttg ata aca gat tgg tgc tgc agg agc tgc acc tta cca      3426
Ser Gly Lys Leu Ile Thr Asp Trp Cys Cys Arg Ser Cys Thr Leu Pro
1095                1100                1105                1110 cca ctg cgc tac caa act gac agc ggc tgt tgg tat ggt atg gag atc      3474
Pro Leu Arg Tyr Gln Thr Asp Ser Gly Cys Trp Tyr Gly Met Glu Ile
            1115                1120                1125 aga cca cag aga cat gat gaa aag acc ctc gtg cag tca caa gtg aat      3522
Arg Pro Gln Arg His Asp Glu Lys Thr Leu Val Gln Ser Gln Val Asn
            1130                1135                1140 gct tat aat gct gat atg att gac cct ttt cag ttg ggc ctt ctg gtc      3570
Ala Tyr Asn Ala Asp Met Ile Asp Pro Phe Gln Leu Gly Leu Leu Val
            1145                1150                1155 gtg ttc ttg gcc acc cag gag gtc ctt cgc aag agg tgg aca gcc aag      3618
Val Phe Leu Ala Thr Gln Glu Val Leu Arg Lys Arg Trp Thr Ala Lys
            1160                1165                1170 atc agc atg cca gct ata ctg att gct ctg cta gtc ctg gtg ttt ggg      3666
Ile Ser Met Pro Ala Ile Leu Ile Ala Leu Leu Val Leu Val Phe Gly
1175                1180                1185                1190 ggc att act tac act gat gtg tta cgc tat gtc atc ttg gtg ggg gca      3714
Gly Ile Thr Tyr Thr Asp Val Leu Arg Tyr Val Ile Leu Val Gly Ala
            1195                1200                1205
```

|  |  |
|---|---|
| gct ttc gca gaa tct aat tcg gga gga gac gtg gta cac ttg gcg ctc<br>Ala Phe Ala Glu Ser Asn Ser Gly Gly Asp Val Val His Leu Ala Leu<br>　　　　1210　　　　　　　　　1215　　　　　　　　　1220 | 3762 |
| atg gcg acc ttc aag ata caa cca gtg ttt atg gtg gca tcg ttt ctc<br>Met Ala Thr Phe Lys Ile Gln Pro Val Phe Met Val Ala Ser Phe Leu<br>1225　　　　　　　　　1230　　　　　　　　　1235 | 3810 |
| aaa gcg aga tgg acc aac cag gag aac att ttg ttg atg ttg gcg gct<br>Lys Ala Arg Trp Thr Asn Gln Glu Asn Ile Leu Leu Met Leu Ala Ala<br>　　　1240　　　　　　　　　1245　　　　　　　　　1250 | 3858 |
| gtt ttc ttt caa atg gct tat cac gat gcc cgc caa att ctg ctc tgg<br>Val Phe Phe Gln Met Ala Tyr His Asp Ala Arg Gln Ile Leu Leu Trp<br>1255　　　　　　　　　1260　　　　　　　　　1265　　　　　　　　　1270 | 3906 |
| gag atc cct gat gtg ttg aat tca ctg gcg gta gct tgg atg ata ctg<br>Glu Ile Pro Asp Val Leu Asn Ser Leu Ala Val Ala Trp Met Ile Leu<br>　　　　　　　　　1275　　　　　　　　　1280　　　　　　　　　1285 | 3954 |
| aga gcc ata aca ttc aca acg aca tca aac gtg gtt gtt ccg ctg cta<br>Arg Ala Ile Thr Phe Thr Thr Thr Ser Asn Val Val Val Pro Leu Leu<br>　　　1290　　　　　　　　　1295　　　　　　　　　1300 | 4002 |
| gcc ctg cta aca ccc ggg ctg aga tgc ttg aat ctg gat gtg tac agg<br>Ala Leu Leu Thr Pro Gly Leu Arg Cys Leu Asn Leu Asp Val Tyr Arg<br>1305　　　　　　　　　1310　　　　　　　　　1315 | 4050 |
| ata ctg ctg ttg atg gtc gga ata ggc agc ttg atc agg gag aag agg<br>Ile Leu Leu Leu Met Val Gly Ile Gly Ser Leu Ile Arg Glu Lys Arg<br>　　　1320　　　　　　　　　1325　　　　　　　　　1330 | 4098 |
| agt gca gct gca aaa aag aaa gga gca agt ctg cta tgc ttg gct cta<br>Ser Ala Ala Ala Lys Lys Lys Gly Ala Ser Leu Leu Cys Leu Ala Leu<br>1335　　　　　　　　　1340　　　　　　　　　1345　　　　　　　　　1350 | 4146 |
| gcc tca aca gga ctt ttc aac ccc atg atc ctt gct gct gga ctg att<br>Ala Ser Thr Gly Leu Phe Asn Pro Met Ile Leu Ala Ala Gly Leu Ile<br>　　　　　　　　　1355　　　　　　　　　1360　　　　　　　　　1365 | 4194 |
| gca tgt gat ccc aac cgt aaa cgc gga tgg ccc gca act gaa gtg atg<br>Ala Cys Asp Pro Asn Arg Lys Arg Gly Trp Pro Ala Thr Glu Val Met<br>　　　1370　　　　　　　　　1375　　　　　　　　　1380 | 4242 |
| aca gct gtc ggc cta atg ttt gcc atc gtc gga ggg ctg gca gag ctt<br>Thr Ala Val Gly Leu Met Phe Ala Ile Val Gly Gly Leu Ala Glu Leu<br>　　　　　　　　　1385　　　　　　　　　1390　　　　　　　　　1395 | 4290 |
| gac att gac tcc atg gcc att cca atg act atc gcg ggg ctc atg ttt<br>Asp Ile Asp Ser Met Ala Ile Pro Met Thr Ile Ala Gly Leu Met Phe<br>　　　1400　　　　　　　　　1405　　　　　　　　　1410 | 4338 |
| gct gct ttc gtg att tct ggg aaa tca aca gat atg tgg att gag aga<br>Ala Ala Phe Val Ile Ser Gly Lys Ser Thr Asp Met Trp Ile Glu Arg<br>1415　　　　　　　　　1420　　　　　　　　　1425　　　　　　　　　1430 | 4386 |
| acg gcg gac att tcc tgg gaa agt gat gca gaa att aca ggc tcg agc<br>Thr Ala Asp Ile Ser Trp Glu Ser Asp Ala Glu Ile Thr Gly Ser Ser<br>　　　　　　　　　1435　　　　　　　　　1440　　　　　　　　　1445 | 4434 |
| gaa aga gtt gat gtg cgg ctt gat gat gat gga aac ttc cag ctc atg<br>Glu Arg Val Asp Val Arg Leu Asp Asp Asp Gly Asn Phe Gln Leu Met<br>　　　1450　　　　　　　　　1455　　　　　　　　　1460 | 4482 |
| aat gat cca gga gca cct tgg aag ata tgg atg ctc aga atg gtc tgt<br>Asn Asp Pro Gly Ala Pro Trp Lys Ile Trp Met Leu Arg Met Val Cys<br>1465　　　　　　　　　1470　　　　　　　　　1475 | 4530 |
| ctc gcg att agt gcg tac acc ccc tgg gca atc ttg ccc tca gta gtt<br>Leu Ala Ile Ser Ala Tyr Thr Pro Trp Ala Ile Leu Pro Ser Val Val<br>　　　1480　　　　　　　　　1485　　　　　　　　　1490 | 4578 |
| gga ttt tgg ata act ctc caa tac aca aag aga gga ggc gtg ttg tgg<br>Gly Phe Trp Ile Thr Leu Gln Tyr Thr Lys Arg Gly Gly Val Leu Trp<br>1495　　　　　　　　　1500　　　　　　　　　1505　　　　　　　　　1510 | 4626 |
| gac act ccc tca cca aag gag tac aaa aag ggg gac acg acc acc ggc<br>Asp Thr Pro Ser Pro Lys Glu Tyr Lys Lys Gly Asp Thr Thr Thr Gly<br>　　　　　　　　　1515　　　　　　　　　1520　　　　　　　　　1525 | 4674 |

| | |
|---|---|
| gtc tac agg atc atg act cgt ggg ctg ctc ggc agt tat caa gca gga<br>Val Tyr Arg Ile Met Thr Arg Gly Leu Leu Gly Ser Tyr Gln Ala Gly<br>          1530                    1535                    1540 | 4722 |
| gcg ggc gtg atg gtt gaa ggt gtt ttc cac acc ctt tgg cat aca aca<br>Ala Gly Val Met Val Glu Gly Val Phe His Thr Leu Trp His Thr Thr<br>1545                    1550                    1555 | 4770 |
| aaa gga gcc gct ttg atg agc gga gag ggc cgc ctg gac cca tac tgg<br>Lys Gly Ala Ala Leu Met Ser Gly Glu Gly Arg Leu Asp Pro Tyr Trp<br>1560                    1565                    1570 | 4818 |
| ggc agt gtc aag gag gat cga ctt tgt tac gga gga ccc tgg aaa ttg<br>Gly Ser Val Lys Glu Asp Arg Leu Cys Tyr Gly Gly Pro Trp Lys Leu<br>1575                  1580                    1585                    1590 | 4866 |
| cag cac aag tgg aac ggg cag gat gag gtg cag atg att gtg gtg gaa<br>Gln His Lys Trp Asn Gly Gln Asp Glu Val Gln Met Ile Val Val Glu<br>                    1595                    1600                    1605 | 4914 |
| cct ggc aag aac gtt aag aac gtc cag acg aaa cca ggg gtg ttc aaa<br>Pro Gly Lys Asn Val Lys Asn Val Gln Thr Lys Pro Gly Val Phe Lys<br>                    1610                    1615                    1620 | 4962 |
| aca cct gaa gga gaa atc ggg gcc gtg act ttg gac ttc ccc act gga<br>Thr Pro Glu Gly Glu Ile Gly Ala Val Thr Leu Asp Phe Pro Thr Gly<br>1625                    1630                    1635 | 5010 |
| aca tca ggc tca cca ata gtg gac aaa aac ggt gat gtg att ggg ctt<br>Thr Ser Gly Ser Pro Ile Val Asp Lys Asn Gly Asp Val Ile Gly Leu<br>                    1640                    1645                    1650 | 5058 |
| tat ggc aat gga gtc ata atg ccc aac ggc tca tac ata agc gcg ata<br>Tyr Gly Asn Gly Val Ile Met Pro Asn Gly Ser Tyr Ile Ser Ala Ile<br>1655                    1660                    1665                    1670 | 5106 |
| gtg cag ggt gaa agg atg gat gag cca atc cca gcc gga ttc gaa cct<br>Val Gln Gly Glu Arg Met Asp Glu Pro Ile Pro Ala Gly Phe Glu Pro<br>                                1675                    1680                    1685 | 5154 |
| gag atg ctg agg aaa aaa cag atc act gta ctg gat ctc cat ccc ggc<br>Glu Met Leu Arg Lys Lys Gln Ile Thr Val Leu Asp Leu His Pro Gly<br>                    1690                    1695                    1700 | 5202 |
| gcc ggt aaa aca agg agg att ctg cca cag atc atc aaa gag gcc ata<br>Ala Gly Lys Thr Arg Arg Ile Leu Pro Gln Ile Ile Lys Glu Ala Ile<br>1705                    1710                    1715 | 5250 |
| aac aga aga ctg aga aca gcc gtg cta gca cca acc agg gtt gtg gct<br>Asn Arg Arg Leu Arg Thr Ala Val Leu Ala Pro Thr Arg Val Val Ala<br>                    1720                    1725                    1730 | 5298 |
| gct gag atg gct gaa gca ctg aga gga ctg ccc atc cgg tac cag aca<br>Ala Glu Met Ala Glu Ala Leu Arg Gly Leu Pro Ile Arg Tyr Gln Thr<br>1735                    1740                    1745                    1750 | 5346 |
| tcc gca gtg ccc aga gaa cat aat gga aat gag att gtt gat gtc atg<br>Ser Ala Val Pro Arg Glu His Asn Gly Asn Glu Ile Val Asp Val Met<br>                    1755                    1760                    1765 | 5394 |
| tgt cat gct acc ctc acc cac agg ctg atg tct cct cac agg gtg ccg<br>Cys His Ala Thr Leu Thr His Arg Leu Met Ser Pro His Arg Val Pro<br>                    1770                    1775                    1780 | 5442 |
| aac tac aac ctg ttc gtg atg gat gag gct cat ttc acc gac cca gct<br>Asn Tyr Asn Leu Phe Val Met Asp Glu Ala His Phe Thr Asp Pro Ala<br>1785                    1790                    1795 | 5490 |
| agc att gca gca aga ggt tac att tcc aca aag gtc gag cta ggg gag<br>Ser Ile Ala Ala Arg Gly Tyr Ile Ser Thr Lys Val Glu Leu Gly Glu<br>1800                    1805                    1810 | 5538 |
| gcg gcg gca ata ttc atg aca gcc acc cca cca ggc act tca gat cca<br>Ala Ala Ala Ile Phe Met Thr Ala Thr Pro Pro Gly Thr Ser Asp Pro<br>1815                    1820                    1825                    1830 | 5586 |
| ttc cca gag tcc aat tca cca att tcc gac tta cag act gag atc ccg<br>Phe Pro Glu Ser Asn Ser Pro Ile Ser Asp Leu Gln Thr Glu Ile Pro<br>                    1835                    1840                    1845 | 5634 |

| | |
|---|---:|
| gat cga gct tgg aac tct gga tac gaa tgg atc aca gaa tac acc ggg<br>Asp Arg Ala Trp Asn Ser Gly Tyr Glu Trp Ile Thr Glu Tyr Thr Gly<br>        1850                    1855                 1860 | 5682 |
| aag acg gtt tgg ttt gtg cct agt gtc aag atg ggg aat gag att gcc<br>Lys Thr Val Trp Phe Val Pro Ser Val Lys Met Gly Asn Glu Ile Ala<br>1865                    1870                    1875 | 5730 |
| ctt tgc cta caa cgt gct gga aag aaa gta gtc caa ttg aac aga aag<br>Leu Cys Leu Gln Arg Ala Gly Lys Lys Val Val Gln Leu Asn Arg Lys<br>       1880                    1885                 1890 | 5778 |
| tcg tac gag acg gag tac cca aaa tgt aag aac gat gat tgg gac ttt<br>Ser Tyr Glu Thr Glu Tyr Pro Lys Cys Lys Asn Asp Asp Trp Asp Phe<br>1895                    1900                    1905                 1910 | 5826 |
| gtt atc aca aca gac ata tct gaa atg ggg gct aac ttc aag gcg agc<br>Val Ile Thr Thr Asp Ile Ser Glu Met Gly Ala Asn Phe Lys Ala Ser<br>                  1915                    1920                 1925 | 5874 |
| agg gtg att gac agc cgg aag agt gtg aaa cca acc atc ata aca gaa<br>Arg Val Ile Asp Ser Arg Lys Ser Val Lys Pro Thr Ile Ile Thr Glu<br>       1930                    1935                 1940 | 5922 |
| gga gaa ggg aga gtg atc ctg gga gaa cca tct gca gtg aca gca gct<br>Gly Glu Gly Arg Val Ile Leu Gly Glu Pro Ser Ala Val Thr Ala Ala<br>1945                    1950                    1955 | 5970 |
| agt gcc gcc cag aga cgt gga cgt atc ggt aga aat ccg tcg caa gtt<br>Ser Ala Ala Gln Arg Arg Gly Arg Ile Gly Arg Asn Pro Ser Gln Val<br>       1960                    1965                 1970 | 6018 |
| ggt gat gag tac tgt tat ggg ggg cac acg aat gaa gac gac tcg aac<br>Gly Asp Glu Tyr Cys Tyr Gly Gly His Thr Asn Glu Asp Asp Ser Asn<br>1975                    1980                    1985                 1990 | 6066 |
| ttc gcc cat tgg act gag gca cga atc atg ctg gac aac atc aac atg<br>Phe Ala His Trp Thr Glu Ala Arg Ile Met Leu Asp Asn Ile Asn Met<br>                  1995                    2000                 2005 | 6114 |
| cca aac gga ctg atc gct caa ttc tac caa cca gag cgt gag aag gta<br>Pro Asn Gly Leu Ile Ala Gln Phe Tyr Gln Pro Glu Arg Glu Lys Val<br>       2010                    2015                 2020 | 6162 |
| tat acc atg gat ggg gaa tac cgg ctc aga gga gaa gag aga aaa aac<br>Tyr Thr Met Asp Gly Glu Tyr Arg Leu Arg Gly Glu Glu Arg Lys Asn<br>                  2025                    2030                 2035 | 6210 |
| ttt ctg gaa ctg ttg agg act gca gat ctg cca gtt tgg ctg gct tac<br>Phe Leu Glu Leu Leu Arg Thr Ala Asp Leu Pro Val Trp Leu Ala Tyr<br>2040                    2045                    2050 | 6258 |
| aag gtt gca gcg gct gga gtg tca tac cac gac cgg agg tgg tgc ttt<br>Lys Val Ala Ala Ala Gly Val Ser Tyr His Asp Arg Arg Trp Cys Phe<br>2055                    2060                    2065                 2070 | 6306 |
| gat ggt cct agg aca aac aca att tta gaa gac aac aac gaa gtg gaa<br>Asp Gly Pro Arg Thr Asn Thr Ile Leu Glu Asp Asn Asn Glu Val Glu<br>                  2075                    2080                 2085 | 6354 |
| gtc atc acg aag ctt ggt gaa agg aag att ctg agg ccg cgc tgg att<br>Val Ile Thr Lys Leu Gly Glu Arg Lys Ile Leu Arg Pro Arg Trp Ile<br>       2090                    2095                 2100 | 6402 |
| gac gcc agg gtg tac tcg gat cac cag gca cta aag gcg ttc aag gac<br>Asp Ala Arg Val Tyr Ser Asp His Gln Ala Leu Lys Ala Phe Lys Asp<br>               2105                    2110                 2115 | 6450 |
| ttc gcc tcg gga aaa cgt tct cag ata ggg ctc att gag gtt ctg gga<br>Phe Ala Ser Gly Lys Arg Ser Gln Ile Gly Leu Ile Glu Val Leu Gly<br>       2120                    2125                 2130 | 6498 |
| aag atg cct gag cac ttc atg ggg aag aca tgg gaa gca ctt gac acc<br>Lys Met Pro Glu His Phe Met Gly Lys Thr Trp Glu Ala Leu Asp Thr<br>2135                    2140                    2145                 2150 | 6546 |
| atg tac gtt gtg gcc act gca gag aaa gga gga aga gct cac aga atg<br>Met Tyr Val Val Ala Thr Ala Glu Lys Gly Gly Arg Ala His Arg Met<br>                  2155                    2160                 2165 | 6594 |

|  |  |
|---|---|
| gcc ctg gag gaa ctg cca gat gct ctt cag aca att gcc ttg att gcc<br>Ala Leu Glu Glu Leu Pro Asp Ala Leu Gln Thr Ile Ala Leu Ile Ala<br>              2170                         2175                          2180 | 6642 |
| tta ttg agt gtg atg acc atg gga gta ttc ttc ctc atg cag cgg<br>Leu Leu Ser Val Met Thr Met Gly Val Phe Phe Leu Met Gln Arg<br>     2185                         2190                         2195 | 6690 |
| aag ggc att gga aag ata ggt tgg gga ggc gct gtc ttg gga gtc gcg<br>Lys Gly Ile Gly Lys Ile Gly Leu Gly Gly Ala Val Leu Gly Val Ala<br>              2200                       2205                       2210 | 6738 |
| acc ttt ttc tgt tgg atg gct gaa gtt cca gga acg aag atc gcc gga<br>Thr Phe Phe Cys Trp Met Ala Glu Val Pro Gly Thr Lys Ile Ala Gly<br>2215                    2220                       2225                        2230 | 6786 |
| atg ttg ctg ctc tcc ctt ctc ttg atg att gtg cta att cct gag cca<br>Met Leu Leu Leu Ser Leu Leu Leu Met Ile Val Leu Ile Pro Glu Pro<br>                2235                       2240                       2245 | 6834 |
| gag aag caa cgt tcg cag aca gac aac cag cta gcc gtg ttc ctg att<br>Glu Lys Gln Arg Ser Gln Thr Asp Asn Gln Leu Ala Val Phe Leu Ile<br>            2250                       2255                       2260 | 6882 |
| tgt gtc atg acc ctt gtg agc gca gtg gca gcc aac gag atg ggt tgg<br>Cys Val Met Thr Leu Val Ser Ala Val Ala Ala Asn Glu Met Gly Trp<br>        2265                     2270                       2275 | 6930 |
| cta gat aag acc aag agt gac ata agc agt ttg ttt ggg caa aga att<br>Leu Asp Lys Thr Lys Ser Asp Ile Ser Ser Leu Phe Gly Gln Arg Ile<br>    2280                    2285                       2290 | 6978 |
| gag gtc aag gag aat ttc agc atg gga gag ttt ctt ttg gac ttg agg<br>Glu Val Lys Glu Asn Phe Ser Met Gly Glu Phe Leu Leu Asp Leu Arg<br>2295                  2300                       2305                       2310 | 7026 |
| ccg gca aca gcc tgg tca ctg tac gct gtg aca aca gcg gtc ctc act<br>Pro Ala Thr Ala Trp Ser Leu Tyr Ala Val Thr Thr Ala Val Leu Thr<br>              2315                       2320                       2325 | 7074 |
| cca ctg cta aag cat ttg atc acg tca gat tac atc aac acc tca ttg<br>Pro Leu Leu Lys His Leu Ile Thr Ser Asp Tyr Ile Asn Thr Ser Leu<br>          2330                       2335                       2340 | 7122 |
| acc tca ata aac gtt cag gca agt gca cta ttc aca ctc gcg cga ggc<br>Thr Ser Ile Asn Val Gln Ala Ser Ala Leu Phe Thr Leu Ala Arg Gly<br>        2345                     2350                       2355 | 7170 |
| ttc ccc ttc gtc gat gtt gga gtg tcg gct ctc ctg cta gca gcc gga<br>Phe Pro Phe Val Asp Val Gly Val Ser Ala Leu Leu Leu Ala Ala Gly<br>      2360                     2365                       2370 | 7218 |
| tgc tgg gga caa gtc acc ctc acc gtt acg gta aca gcg gca aca ctc<br>Cys Trp Gly Gln Val Thr Leu Thr Val Thr Val Thr Ala Ala Thr Leu<br>2375                  2380                       2385                       2390 | 7266 |
| ctt ttt tgc cac tat gcc tac atg gtt ccc ggt tgg caa gct gag gca<br>Leu Phe Cys His Tyr Ala Tyr Met Val Pro Gly Trp Gln Ala Glu Ala<br>              2395                       2400                       2405 | 7314 |
| atg cgc tca gcc cag cgg cgg aca gcg gcc gga atc atg aag aac gct<br>Met Arg Ser Ala Gln Arg Arg Thr Ala Ala Gly Ile Met Lys Asn Ala<br>           2410                       2415                       2420 | 7362 |
| gta gtg gat ggc atc gtg gcc acg gac gtc cca gaa tta gag cgc acc<br>Val Val Asp Gly Ile Val Ala Thr Asp Val Pro Glu Leu Glu Arg Thr<br>         2425                       2430                       2435 | 7410 |
| aca ccc atc atg cag aag aaa gtt gga cag atc atg ctg atc ttg gtg<br>Thr Pro Ile Met Gln Lys Lys Val Gly Gln Ile Met Leu Ile Leu Val<br>       2440                     2445                       2450 | 7458 |
| tct cta gct gca gta gta gtg aac ccg tct gtg aag aca gta cga gaa<br>Ser Leu Ala Ala Val Val Val Asn Pro Ser Val Lys Thr Val Arg Glu<br>2455                  2460                       2465                       2470 | 7506 |
| gcc gga att ttg atc acg gcc gca gcg gtg acg ctt tgg gag aat gga<br>Ala Gly Ile Leu Ile Thr Ala Ala Ala Val Thr Leu Trp Glu Asn Gly<br>              2475                       2480                       2485 | 7554 |

```
gca agc tct gtt tgg aac gca aca act gcc atc gga ctc tgc cac atc      7602
Ala Ser Ser Val Trp Asn Ala Thr Thr Ala Ile Gly Leu Cys His Ile
            2490                2495                2500 atg cgt ggg ggt tgg ttg tca tgt cta tcc ata aca tgg aca ctc ata      7650
Met Arg Gly Gly Trp Leu Ser Cys Leu Ser Ile Thr Trp Thr Leu Ile
        2505                2510                2515 aag aac atg gaa aaa cca gga cta aaa aga ggt ggg gca aaa gga cgc      7698
Lys Asn Met Glu Lys Pro Gly Leu Lys Arg Gly Gly Ala Lys Gly Arg
    2520                2525                2530 acc ttg gga gag gtt tgg aaa gaa aga ctc aac cag atg aca aaa gaa      7746
Thr Leu Gly Glu Val Trp Lys Glu Arg Leu Asn Gln Met Thr Lys Glu
2535                2540                2545                2550 gag ttc act agg tac cgc aaa gag gcc atc atc gaa gtc gat cgc tca      7794
Glu Phe Thr Arg Tyr Arg Lys Glu Ala Ile Ile Glu Val Asp Arg Ser
            2555                2560                2565 gcg gca aaa cac gcc agg aaa gaa ggc aat gtc act gga ggg cat cca      7842
Ala Ala Lys His Ala Arg Lys Glu Gly Asn Val Thr Gly Gly His Pro
        2570                2575                2580 gtc tct agg ggc aca gca aaa ctg aga tgg ctg gtc gaa cgg agg ttt      7890
Val Ser Arg Gly Thr Ala Lys Leu Arg Trp Leu Val Glu Arg Arg Phe
    2585                2590                2595 ctc gaa ccg gtc gga aaa gtg att gac ctt gga tgt gga aga ggc ggt      7938
Leu Glu Pro Val Gly Lys Val Ile Asp Leu Gly Cys Gly Arg Gly Gly
2600                2605                2610 tgg tgt tac tat atg gca acc caa aaa aga gtc caa gaa gtc aga ggg      7986
Trp Cys Tyr Tyr Met Ala Thr Gln Lys Arg Val Gln Glu Val Arg Gly
2615                2620                2625                2630 tac aca aag ggc ggt ccc gga cat gaa gag ccc caa cta gtg caa agt      8034
Tyr Thr Lys Gly Gly Pro Gly His Glu Glu Pro Gln Leu Val Gln Ser
            2635                2640                2645 tat gga tgg aac att gtc acc atg aag agt gga gtg gat gtg ttc tac      8082
Tyr Gly Trp Asn Ile Val Thr Met Lys Ser Gly Val Asp Val Phe Tyr
        2650                2655                2660 aga cct tct gag tgt tgt gac acc ctc ctt tgt gac atc gga gag tcc      8130
Arg Pro Ser Glu Cys Cys Asp Thr Leu Leu Cys Asp Ile Gly Glu Ser
    2665                2670                2675 tcg tca agt gct gag gtt gaa gag cat agg acg att cgg gtc ctt gaa      8178
Ser Ser Ser Ala Glu Val Glu Glu His Arg Thr Ile Arg Val Leu Glu
2680                2685                2690 atg gtt gag gac tgg ctg cac cga ggg cca agg gaa ttt tgc gtg aag      8226
Met Val Glu Asp Trp Leu His Arg Gly Pro Arg Glu Phe Cys Val Lys
2695                2700                2705                2710 gtg ctc tgc ccc tac atg ccg aaa gtc ata gag aag atg gag ctg ctc      8274
Val Leu Cys Pro Tyr Met Pro Lys Val Ile Glu Lys Met Glu Leu Leu
            2715                2720                2725 caa cgc cgg tat ggg ggg gga ctg gtc aga aac cca ctc tca cgg aat      8322
Gln Arg Arg Tyr Gly Gly Gly Leu Val Arg Asn Pro Leu Ser Arg Asn
        2730                2735                2740 tcc acg cac gag atg tat tgg gtg agt cga gct tca ggc aat gtg gta      8370
Ser Thr His Glu Met Tyr Trp Val Ser Arg Ala Ser Gly Asn Val Val
    2745                2750                2755 cat tca gtg aat atg acc agc cag gtg ctc cta gga aga atg gaa aaa      8418
His Ser Val Asn Met Thr Ser Gln Val Leu Leu Gly Arg Met Glu Lys
2760                2765                2770 agg acc tgg aag gga ccc caa tac gag gaa gat gta aac ttg gga agt      8466
Arg Thr Trp Lys Gly Pro Gln Tyr Glu Glu Asp Val Asn Leu Gly Ser
2775                2780                2785                2790 gga acc agg gcg gtg gga aaa ccc ctg ctc aac tca gac acc agt aaa      8514
Gly Thr Arg Ala Val Gly Lys Pro Leu Leu Asn Ser Asp Thr Ser Lys
            2795                2800                2805
```

| | |
|---|---|
| atc aag aac agg att gaa cga ctc agg cgt gag tac agt tcg acg tgg<br>Ile Lys Asn Arg Ile Glu Arg Leu Arg Arg Glu Tyr Ser Ser Thr Trp<br>    2810                         2815                    2820 | 8562 |
| cac cac gat gag aac cac cca tat aga acc tgg aac tat cac ggc agt<br>His His Asp Glu Asn His Pro Tyr Arg Thr Trp Asn Tyr His Gly Ser<br>    2825                         2830                    2835 | 8610 |
| tat gat gtg aag ccc aca ggc tcc gcc agt tcg ctg gtc aat gga gtg<br>Tyr Asp Val Lys Pro Thr Gly Ser Ala Ser Ser Leu Val Asn Gly Val<br>    2840                         2845                    2850 | 8658 |
| gtc agg ctc ctc tca aaa cca tgg gac acc atc acg aat gtt acc acc<br>Val Arg Leu Leu Ser Lys Pro Trp Asp Thr Ile Thr Asn Val Thr Thr<br>2855                  2860                    2865                    2870 | 8706 |
| atg gcc atg act gac act act ccc ttc ggg cag cag cga gtg ttc aaa<br>Met Ala Met Thr Asp Thr Thr Pro Phe Gly Gln Gln Arg Val Phe Lys<br>                      2875                    2880                    2885 | 8754 |
| gag aag gtg gac acg aaa gct cct gaa ccg cca gaa gga gtg aag tac<br>Glu Lys Val Asp Thr Lys Ala Pro Glu Pro Pro Glu Gly Val Lys Tyr<br>    2890                         2895                    2900 | 8802 |
| gtg ctc aat gag acc acc aac tgg ttg tgg gcg ttt ttg gcc aga gaa<br>Val Leu Asn Glu Thr Thr Asn Trp Leu Trp Ala Phe Leu Ala Arg Glu<br>                      2905                    2910                    2915 | 8850 |
| aaa cgt ccc aga atg tgc tct cga gag gaa ttc ata aga aag gtc aac<br>Lys Arg Pro Arg Met Cys Ser Arg Glu Glu Phe Ile Arg Lys Val Asn<br>    2920                         2925                    2930 | 8898 |
| agc aat gca gct ttg ggt gcc atg ttt gaa gag cag aat caa tgg agg<br>Ser Asn Ala Ala Leu Gly Ala Met Phe Glu Glu Gln Asn Gln Trp Arg<br>2935                  2940                    2945                    2950 | 8946 |
| agc gcc aga gaa gca gtt gaa gat cca aaa ttt tgg gag atg gtg gat<br>Ser Ala Arg Glu Ala Val Glu Asp Pro Lys Phe Trp Glu Met Val Asp<br>                      2955                    2960                    2965 | 8994 |
| gag gag cgc gag gca cat ctg cgg ggg gaa tgt cac act tgc att tac<br>Glu Glu Arg Glu Ala His Leu Arg Gly Glu Cys His Thr Cys Ile Tyr<br>    2970                         2975                    2980 | 9042 |
| aac atg atg gga aag aga gag aaa aaa ccc gga gag ttc gga aag gcc<br>Asn Met Met Gly Lys Arg Glu Lys Lys Pro Gly Glu Phe Gly Lys Ala<br>                      2985                    2990                    2995 | 9090 |
| aag gga agc aga gcc att tgg ttc atg tgg ctc gga gct cgc ttt ctg<br>Lys Gly Ser Arg Ala Ile Trp Phe Met Trp Leu Gly Ala Arg Phe Leu<br>    3000                         3005                    3010 | 9138 |
| gag ttc gag gct ctg ggt ttt ctc aat gaa gac cac tgg ctt gga aga<br>Glu Phe Glu Ala Leu Gly Phe Leu Asn Glu Asp His Trp Leu Gly Arg<br>3015                  3020                    3025                    3030 | 9186 |
| aag aac tca gga gga ggt gtc gag ggc ttg ggc ctc caa aaa ctg ggt<br>Lys Asn Ser Gly Gly Gly Val Glu Gly Leu Gly Leu Gln Lys Leu Gly<br>                      3035                    3040                    3045 | 9234 |
| tac atc ctg cgt gaa gtt ggc acc cgg cct ggg ggc aag atc tat gct<br>Tyr Ile Leu Arg Glu Val Gly Thr Arg Pro Gly Gly Lys Ile Tyr Ala<br>    3050                         3055                    3060 | 9282 |
| gat gac aca gct ggc tgg gac acc cgc atc acg aga gct gac ttg gaa<br>Asp Asp Thr Ala Gly Trp Asp Thr Arg Ile Thr Arg Ala Asp Leu Glu<br>                      3065                    3070                    3075 | 9330 |
| aat gaa gct aag gtg ctt gag ctg ctt gat ggg gaa cat cgg cgt ctt<br>Asn Glu Ala Lys Val Leu Glu Leu Leu Asp Gly Glu His Arg Arg Leu<br>    3080                         3085                    3090 | 9378 |
| gcc agg gcc atc att gag ctc acc tat cgt cac aaa gtt gtg aaa gtg<br>Ala Arg Ala Ile Ile Glu Leu Thr Tyr Arg His Lys Val Val Lys Val<br>3095                  3100                    3105                    3110 | 9426 |
| atg cgc ccg gct gct gat gga aga acc gtc atg gat gtt atc tcc aga<br>Met Arg Pro Ala Ala Asp Gly Arg Thr Val Met Asp Val Ile Ser Arg<br>                      3115                    3120                    3125 | 9474 |

```
gaa gat cag agg ggg agt gga caa gtt gtc acc tac gcc cta aac act    9522
Glu Asp Gln Arg Gly Ser Gly Gln Val Val Thr Tyr Ala Leu Asn Thr
            3130                3135                3140 ttc acc aac ctg gcc gtc cag ctg gtg agg atg atg gaa ggg gaa gga    9570
Phe Thr Asn Leu Ala Val Gln Leu Val Arg Met Met Glu Gly Glu Gly
        3145                3150                3155 gtg att ggc cca gat gat gtg gag aaa ctc aca aaa ggg aaa gga ccc    9618
Val Ile Gly Pro Asp Asp Val Glu Lys Leu Thr Lys Gly Lys Gly Pro
    3160                3165                3170 aaa gtc agg acc tgg ctg ttt gag aat ggg gaa gaa aga ctc agc cgc    9666
Lys Val Arg Thr Trp Leu Phe Glu Asn Gly Glu Glu Arg Leu Ser Arg
3175                3180                3185                3190 atg gct gtc agt gga gat gac tgt gtg gta aag ccc ctg gac gat cgc    9714
Met Ala Val Ser Gly Asp Asp Cys Val Val Lys Pro Leu Asp Asp Arg
                3195                3200                3205 ttt gcc acc tcg ctc cac ttc ctc aat gct atg tca aag gtt cgc aaa    9762
Phe Ala Thr Ser Leu His Phe Leu Asn Ala Met Ser Lys Val Arg Lys
            3210                3215                3220 gac atc caa gag tgg aaa ccg tca act gga tgg tat gat tgg cag cag    9810
Asp Ile Gln Glu Trp Lys Pro Ser Thr Gly Trp Tyr Asp Trp Gln Gln
        3225                3230                3235 gtt cca ttt tgc tca aac cat ttc act gaa ttg atc atg aaa gat gga    9858
Val Pro Phe Cys Ser Asn His Phe Thr Glu Leu Ile Met Lys Asp Gly
    3240                3245                3250 aga aca ctg gtg gtt cca tgc cga gga cag gat gaa ttg gta ggc aga    9906
Arg Thr Leu Val Val Pro Cys Arg Gly Gln Asp Glu Leu Val Gly Arg
3255                3260                3265                3270 gct cgc ata tct cca ggg gcc gga tgg aac gtc cgc gac act gct tgt    9954
Ala Arg Ile Ser Pro Gly Ala Gly Trp Asn Val Arg Asp Thr Ala Cys
                3275                3280                3285 ctg gct aag tct tat gcc cag atg tgg ctg ctt ctg tac ttc cac aga   10002
Leu Ala Lys Ser Tyr Ala Gln Met Trp Leu Leu Leu Tyr Phe His Arg
            3290                3295                3300 aga gac ctg cgg ctc atg gcc aac gcc att tgc tcc gct gtc cct gtg   10050
Arg Asp Leu Arg Leu Met Ala Asn Ala Ile Cys Ser Ala Val Pro Val
        3305                3310                3315 aat tgg gtc cct acc gga aga acc acg tgg tcc atc cat gca gga gga   10098
Asn Trp Val Pro Thr Gly Arg Thr Thr Trp Ser Ile His Ala Gly Gly
    3320                3325                3330 gag tgg atg aca aca gag gac atg ttg gag gtc tgg aac cgt gtt tgg   10146
Glu Trp Met Thr Thr Glu Asp Met Leu Glu Val Trp Asn Arg Val Trp
3335                3340                3345                3350 ata gag gag aat gaa tgg atg gaa gac aaa acc cca gtg gag aaa tgg   10194
Ile Glu Glu Asn Glu Trp Met Glu Asp Lys Thr Pro Val Glu Lys Trp
                3355                3360                3365 agt gac gtc cca tat tca gga aaa cga gag gac atc tgg tgt ggc agc   10242
Ser Asp Val Pro Tyr Ser Gly Lys Arg Glu Asp Ile Trp Cys Gly Ser
            3370                3375                3380 ctg att ggc aca aga gcc cga gcc acg tgg gca gaa aac atc cag gtg   10290
Leu Ile Gly Thr Arg Ala Arg Ala Thr Trp Ala Glu Asn Ile Gln Val
        3385                3390                3395 gct atc aac caa gtc aga gca atc atc gga gat gag aag tat gtg gat   10338
Ala Ile Asn Gln Val Arg Ala Ile Ile Gly Asp Glu Lys Tyr Val Asp
    3400                3405                3410 tac atg agt tca cta aag aga tat gaa gac aca act ttg gtt gag gac   10386
Tyr Met Ser Ser Leu Lys Arg Tyr Glu Asp Thr Thr Leu Val Glu Asp
3415                3420                3425                3430 aca gta ctg tag atatttaatc aattgtaaat agacaatata agtatgcata        10438
Thr Val Leu
```

-continued

```
aaagtgtagt tttatagtag tatttagtgg tgttagtgta aatagttaag aaaattttga    10498
ggagaaagtc aggccgggaa gttcccgcca ccggaagttg agtagacggt gctgcctgcg    10558
actcaacccc aggaggactg ggtgaacaaa gccgcgaagt gatccatgta agccctcaga    10618
accgtctcgg aaggaggacc ccacatgttg taacttcaaa gcccaatgtc agaccacgct    10678
acggcgtgct actctgcgga gagtgcagtc tgcgatagtg ccccaggagg actgggttaa    10738
caaaggcaaa ccaacgcccc acgcggccct agccccggta atggtgttaa ccagggcgaa    10798
aggactagag gttagaggag accccgcggt ttaaagtgca cggcccagcc tgactgaagc    10858
tgtaggtcag gggaaggact agaggttagt ggagaccccg tgccacaaaa caccacaaca    10918
aaacagcata ttgacacctg ggatagacta ggagatcttc tgctctgcac aaccagccac    10978
acggcacagt gcgccgacaa tggtggctgg tggtgcgaga acacaggatc t             11029
```

<210> SEQ ID NO 2
<211> LENGTH: 3433
<212> TYPE: PRT
<213> ORGANISM: West Nile virus

<400> SEQUENCE: 2

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Ser Leu Thr Val Gln Thr His Gly Glu
    210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
            260                 265                 270

Met Gln Arg Val Val Phe Val Val Leu Leu Leu Leu Val Ala Pro Ala
```

```
                275                 280                 285
Tyr Ser Phe Asn Cys Leu Gly Met Ser Asn Arg Asp Phe Leu Glu Gly
            290                 295                 300
Val Ser Gly Ala Thr Trp Val Asp Leu Val Leu Glu Gly Asp Ser Cys
305                 310                 315                 320
Val Thr Ile Met Ser Lys Asp Lys Pro Thr Ile Asp Val Lys Met Met
            325                 330                 335
Asn Met Glu Ala Ala Asn Leu Ala Glu Val Arg Ser Tyr Cys Tyr Leu
            340                 345                 350
Ala Thr Val Ser Asp Leu Ser Thr Lys Ala Ala Cys Pro Thr Met Gly
            355                 360                 365
Glu Ala His Asn Asp Lys Arg Ala Asp Pro Ala Phe Val Cys Arg Gln
            370                 375                 380
Gly Val Val Asp Arg Gly Trp Gly Asn Gly Cys Gly Leu Phe Gly Lys
385                 390                 395                 400
Gly Ser Ile Asp Thr Cys Ala Lys Phe Ala Cys Ser Thr Lys Ala Ile
            405                 410                 415
Gly Arg Thr Ile Leu Lys Glu Asn Ile Lys Tyr Glu Val Ala Ile Phe
            420                 425                 430
Val His Gly Pro Thr Thr Val Glu Ser His Gly Asn Tyr Ser Thr Gln
            435                 440                 445
Val Gly Ala Thr Gln Ala Gly Arg Phe Ser Ile Thr Pro Ala Ala Pro
            450                 455                 460
Ser Tyr Thr Leu Lys Leu Gly Glu Tyr Gly Glu Val Thr Val Asp Cys
465                 470                 475                 480
Glu Pro Arg Ser Gly Ile Asp Thr Asn Ala Tyr Tyr Val Met Thr Val
            485                 490                 495
Gly Thr Lys Thr Phe Leu Val His Arg Glu Trp Phe Met Asp Leu Asn
            500                 505                 510
Leu Pro Trp Ser Ser Ala Gly Ser Thr Val Trp Arg Asn Arg Glu Thr
            515                 520                 525
Leu Met Glu Phe Glu Glu Pro His Ala Thr Lys Gln Ser Val Ile Ala
            530                 535                 540
Leu Gly Ser Gln Glu Gly Ala Leu His Gln Ala Leu Ala Gly Ala Ile
545                 550                 555                 560
Pro Val Glu Phe Ser Ser Asn Thr Val Lys Leu Thr Ser Gly His Leu
            565                 570                 575
Lys Cys Arg Val Lys Met Glu Lys Leu Gln Leu Lys Gly Thr Thr Tyr
            580                 585                 590
Gly Val Cys Ser Lys Ala Phe Lys Phe Leu Gly Thr Pro Ala Asp Thr
            595                 600                 605
Gly His Gly Thr Val Val Leu Glu Leu Gln Tyr Thr Gly Thr Asp Gly
            610                 615                 620
Pro Cys Lys Val Pro Ile Ser Ser Val Ala Ser Leu Asn Asp Leu Thr
625                 630                 635                 640
Pro Val Gly Arg Leu Val Thr Val Asn Pro Phe Val Ser Val Ala Thr
            645                 650                 655
Ala Asn Ala Lys Val Leu Ile Glu Leu Glu Pro Pro Phe Gly Asp Ser
            660                 665                 670
Tyr Ile Val Val Gly Arg Gly Glu Gln Gln Ile Asn His His Trp His
            675                 680                 685
Lys Ser Gly Ser Ser Ile Gly Lys Ala Phe Thr Thr Thr Leu Lys Gly
            690                 695                 700
```

-continued

```
Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
            725                 730                 735

Gly Gly Ala Phe Arg Ser Leu Phe Gly Gly Met Ser Trp Ile Thr Gln
        740                 745                 750

Gly Leu Leu Gly Ala Leu Leu Leu Trp Met Gly Ile Asn Ala Arg Asp
    755                 760                 765

Arg Ser Ile Ala Leu Thr Phe Leu Ala Val Gly Gly Val Leu Leu Phe
770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
            805                 810                 815

Glu Ala Trp Met Asp Arg Tyr Lys Tyr Tyr Pro Glu Thr Pro Gln Gly
        820                 825                 830

Leu Ala Lys Ile Ile Gln Lys Ala His Lys Glu Gly Val Cys Gly Leu
    835                 840                 845

Arg Ser Val Ser Arg Leu Glu His Gln Met Trp Glu Ala Val Lys Asp
850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
            885                 890                 895

Ala Thr Thr Glu Lys Leu Glu Ile Gly Trp Lys Ala Trp Gly Lys Ser
        900                 905                 910

Ile Leu Phe Ala Pro Glu Leu Ala Asn Asn Thr Phe Val Val Asp Gly
    915                 920                 925

Pro Glu Thr Lys Glu Cys Pro Thr Gln Asn Arg Ala Trp Asn Ser Leu
930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
            965                 970                 975

Thr Ala Val Lys Asn Asn Leu Ala Ile His Ser Asp Leu Ser Tyr Trp
        980                 985                 990

Ile Glu Ser Arg Leu Asn Asp Thr Trp Lys Leu Glu Arg Ala Val Leu
    995                 1000                1005

Gly Glu Val Lys Ser Cys Thr Trp Pro Glu Thr His Thr Leu Trp Gly
1010                1015                1020

Asp Gly Ile Leu Glu Ser Asp Leu Ile Ile Pro Val Thr Leu Ala Gly
1025                1030                1035                1040

Pro Arg Ser Asn His Asn Arg Arg Pro Gly Tyr Lys Thr Gln Asn Gln
            1045                1050                1055

Gly Pro Trp Asp Glu Gly Arg Val Glu Ile Asp Phe Asp Tyr Cys Pro
        1060                1065                1070

Gly Thr Thr Val Thr Leu Ser Glu Ser Cys Gly His Arg Gly Pro Ala
    1075                1080                1085

Thr Arg Thr Thr Thr Glu Ser Gly Lys Leu Ile Thr Asp Trp Cys Cys
1090                1095                1100

Arg Ser Cys Thr Leu Pro Pro Leu Arg Tyr Gln Thr Asp Ser Gly Cys
1105                1110                1115                1120

Trp Tyr Gly Met Glu Ile Arg Pro Gln Arg His Asp Glu Lys Thr Leu
            1125                1130                1135
```

-continued

Val Gln Ser Gln Val Asn Ala Tyr Asn Ala Asp Met Ile Asp Pro Phe
            1140                1145                1150

Gln Leu Gly Leu Leu Val Val Phe Leu Ala Thr Gln Glu Val Leu Arg
        1155                1160                1165

Lys Arg Trp Thr Ala Lys Ile Ser Met Pro Ala Ile Leu Ile Ala Leu
    1170                1175                1180

Leu Val Leu Val Phe Gly Gly Ile Thr Tyr Thr Asp Val Leu Arg Tyr
1185                1190                1195                1200

Val Ile Leu Val Gly Ala Ala Phe Ala Glu Ser Asn Ser Gly Gly Asp
            1205                1210                1215

Val Val His Leu Ala Leu Met Ala Thr Phe Lys Ile Gln Pro Val Phe
        1220                1225                1230

Met Val Ala Ser Phe Leu Lys Ala Arg Trp Thr Asn Gln Glu Asn Ile
    1235                1240                1245

Leu Leu Met Leu Ala Ala Val Phe Phe Gln Met Ala Tyr His Asp Ala
1250                1255                1260

Arg Gln Ile Leu Leu Trp Glu Ile Pro Asp Val Leu Asn Ser Leu Ala
1265                1270                1275                1280

Val Ala Trp Met Ile Leu Arg Ala Ile Thr Phe Thr Thr Thr Ser Asn
            1285                1290                1295

Val Val Val Pro Leu Leu Ala Leu Leu Thr Pro Gly Leu Arg Cys Leu
        1300                1305                1310

Asn Leu Asp Val Tyr Arg Ile Leu Leu Leu Met Val Gly Ile Gly Ser
    1315                1320                1325

Leu Ile Arg Glu Lys Arg Ser Ala Ala Ala Lys Lys Lys Gly Ala Ser
1330                1335                1340

Leu Leu Cys Leu Ala Leu Ala Ser Thr Gly Leu Phe Asn Pro Met Ile
1345                1350                1355                1360

Leu Ala Ala Gly Leu Ile Ala Cys Asp Pro Asn Arg Lys Arg Gly Trp
            1365                1370                1375

Pro Ala Thr Glu Val Met Thr Ala Val Gly Leu Met Phe Ala Ile Val
        1380                1385                1390

Gly Gly Leu Ala Glu Leu Asp Ile Asp Ser Met Ala Ile Pro Met Thr
    1395                1400                1405

Ile Ala Gly Leu Met Phe Ala Ala Phe Val Ile Ser Gly Lys Ser Thr
1410                1415                1420

Asp Met Trp Ile Glu Arg Thr Ala Asp Ile Ser Trp Glu Ser Asp Ala
1425                1430                1435                1440

Glu Ile Thr Gly Ser Ser Glu Arg Val Asp Val Arg Leu Asp Asp Asp
            1445                1450                1455

Gly Asn Phe Gln Leu Met Asn Asp Pro Gly Ala Pro Trp Lys Ile Trp
        1460                1465                1470

Met Leu Arg Met Val Cys Leu Ala Ile Ser Ala Tyr Thr Pro Trp Ala
    1475                1480                1485

Ile Leu Pro Ser Val Val Gly Phe Trp Ile Thr Leu Gln Tyr Thr Lys
1490                1495                1500

Arg Gly Gly Val Leu Trp Asp Thr Pro Ser Pro Lys Glu Tyr Lys Lys
1505                1510                1515                1520

Gly Asp Thr Thr Thr Gly Val Tyr Arg Ile Met Thr Arg Gly Leu Leu
            1525                1530                1535

Gly Ser Tyr Gln Ala Gly Ala Gly Val Met Val Glu Gly Val Phe His
        1540                1545                1550

Thr Leu Trp His Thr Thr Lys Gly Ala Ala Leu Met Ser Gly Glu Gly

```
            1555                1560                1565
Arg Leu Asp Pro Tyr Trp Gly Ser Val Lys Glu Asp Arg Leu Cys Tyr
    1570                1575                1580
Gly Gly Pro Trp Lys Leu Gln His Lys Trp Asn Gly Gln Asp Glu Val
1585                1590                1595                1600
Gln Met Ile Val Val Glu Pro Gly Lys Asn Val Lys Asn Val Gln Thr
        1605                1610                1615
Lys Pro Gly Val Phe Lys Thr Pro Glu Gly Glu Ile Gly Ala Val Thr
    1620                1625                1630
Leu Asp Phe Pro Thr Gly Thr Ser Gly Ser Pro Ile Val Asp Lys Asn
        1635                1640                1645
Gly Asp Val Ile Gly Leu Tyr Gly Asn Gly Val Ile Met Pro Asn Gly
    1650                1655                1660
Ser Tyr Ile Ser Ala Ile Val Gln Gly Glu Arg Met Asp Glu Pro Ile
1665                1670                1675                1680
Pro Ala Gly Phe Glu Pro Glu Met Leu Arg Lys Lys Gln Ile Thr Val
            1685                1690                1695
Leu Asp Leu His Pro Gly Ala Gly Lys Thr Arg Arg Ile Leu Pro Gln
        1700                1705                1710
Ile Ile Lys Glu Ala Ile Asn Arg Arg Leu Arg Thr Ala Val Leu Ala
    1715                1720                1725
Pro Thr Arg Val Val Ala Ala Glu Met Ala Glu Ala Leu Arg Gly Leu
    1730                1735                1740
Pro Ile Arg Tyr Gln Thr Ser Ala Val Pro Arg Glu His Asn Gly Asn
1745                1750                1755                1760
Glu Ile Val Asp Val Met Cys His Ala Thr Leu Thr His Arg Leu Met
        1765                1770                1775
Ser Pro His Arg Val Pro Asn Tyr Asn Leu Phe Val Met Asp Glu Ala
        1780                1785                1790
His Phe Thr Asp Pro Ala Ser Ile Ala Ala Arg Gly Tyr Ile Ser Thr
    1795                1800                1805
Lys Val Glu Leu Gly Glu Ala Ala Ala Ile Phe Met Thr Ala Thr Pro
    1810                1815                1820
Pro Gly Thr Ser Asp Pro Phe Pro Glu Ser Asn Ser Pro Ile Ser Asp
1825                1830                1835                1840
Leu Gln Thr Glu Ile Pro Asp Arg Ala Trp Asn Ser Gly Tyr Glu Trp
        1845                1850                1855
Ile Thr Glu Tyr Thr Gly Lys Thr Val Trp Phe Val Pro Ser Val Lys
        1860                1865                1870
Met Gly Asn Glu Ile Ala Leu Cys Leu Gln Arg Ala Gly Lys Lys Val
    1875                1880                1885
Val Gln Leu Asn Arg Lys Ser Tyr Glu Thr Glu Tyr Pro Lys Cys Lys
    1890                1895                1900
Asn Asp Asp Trp Asp Phe Val Ile Thr Thr Asp Ile Ser Glu Met Gly
1905                1910                1915                1920
Ala Asn Phe Lys Ala Ser Arg Val Ile Asp Ser Arg Lys Ser Val Lys
        1925                1930                1935
Pro Thr Ile Ile Thr Glu Gly Glu Gly Arg Val Ile Leu Gly Glu Pro
        1940                1945                1950
Ser Ala Val Thr Ala Ala Ser Ala Ala Gln Arg Arg Gly Arg Ile Gly
    1955                1960                1965
Arg Asn Pro Ser Gln Val Gly Asp Glu Tyr Cys Tyr Gly Gly His Thr
    1970                1975                1980
```

-continued

Asn Glu Asp Asp Ser Asn Phe Ala His Trp Thr Glu Ala Arg Ile Met
1985                1990                1995                2000

Leu Asp Asn Ile Asn Met Pro Asn Gly Leu Ile Ala Gln Phe Tyr Gln
            2005                2010                2015

Pro Glu Arg Glu Lys Val Tyr Thr Met Asp Gly Glu Tyr Arg Leu Arg
        2020                2025                2030

Gly Glu Glu Arg Lys Asn Phe Leu Glu Leu Leu Arg Thr Ala Asp Leu
            2035                2040                2045

Pro Val Trp Leu Ala Tyr Lys Val Ala Ala Ala Gly Val Ser Tyr His
        2050                2055                2060

Asp Arg Arg Trp Cys Phe Asp Gly Pro Arg Thr Asn Thr Ile Leu Glu
2065                2070                2075                2080

Asp Asn Asn Glu Val Glu Val Ile Thr Lys Leu Gly Glu Arg Lys Ile
            2085                2090                2095

Leu Arg Pro Arg Trp Ile Asp Ala Arg Val Tyr Ser Asp His Gln Ala
        2100                2105                2110

Leu Lys Ala Phe Lys Asp Phe Ala Ser Gly Lys Arg Ser Gln Ile Gly
            2115                2120                2125

Leu Ile Glu Val Leu Gly Lys Met Pro Glu His Phe Met Gly Lys Thr
        2130                2135                2140

Trp Glu Ala Leu Asp Thr Met Tyr Val Val Ala Thr Ala Glu Lys Gly
2145                2150                2155                2160

Gly Arg Ala His Arg Met Ala Leu Glu Glu Leu Pro Asp Ala Leu Gln
            2165                2170                2175

Thr Ile Ala Leu Ile Ala Leu Leu Ser Val Met Thr Met Gly Val Phe
        2180                2185                2190

Phe Leu Leu Met Gln Arg Lys Gly Ile Gly Lys Ile Gly Leu Gly Gly
            2195                2200                2205

Ala Val Leu Gly Val Ala Thr Phe Phe Cys Trp Met Ala Glu Val Pro
        2210                2215                2220

Gly Thr Lys Ile Ala Gly Met Leu Leu Leu Ser Leu Leu Leu Met Ile
2225                2230                2235                2240

Val Leu Ile Pro Glu Pro Glu Lys Gln Arg Ser Gln Thr Asp Asn Gln
            2245                2250                2255

Leu Ala Val Phe Leu Ile Cys Val Met Thr Leu Val Ser Ala Val Ala
        2260                2265                2270

Ala Asn Glu Met Gly Trp Leu Asp Lys Thr Lys Ser Asp Ile Ser Ser
            2275                2280                2285

Leu Phe Gly Gln Arg Ile Glu Val Lys Glu Asn Phe Ser Met Gly Glu
        2290                2295                2300

Phe Leu Leu Asp Leu Arg Pro Ala Thr Ala Trp Ser Leu Tyr Ala Val
2305                2310                2315                2320

Thr Thr Ala Val Leu Thr Pro Leu Leu Lys His Leu Ile Thr Ser Asp
            2325                2330                2335

Tyr Ile Asn Thr Ser Leu Thr Ser Ile Asn Val Gln Ala Ser Ala Leu
        2340                2345                2350

Phe Thr Leu Ala Arg Gly Phe Pro Phe Val Asp Val Gly Val Ser Ala
            2355                2360                2365

Leu Leu Leu Ala Ala Gly Cys Trp Gly Gln Val Thr Leu Thr Val Thr
        2370                2375                2380

Val Thr Ala Ala Thr Leu Leu Phe Cys His Tyr Ala Tyr Met Val Pro
2385                2390                2395                2400

Gly Trp Gln Ala Glu Ala Met Arg Ser Ala Gln Arg Arg Thr Ala Ala
            2405                2410                2415

```
Gly Ile Met Lys Asn Ala Val Val Asp Gly Ile Val Ala Thr Asp Val
            2420                2425                2430

Pro Glu Leu Glu Arg Thr Thr Pro Ile Met Gln Lys Lys Val Gly Gln
            2435                2440                2445

Ile Met Leu Ile Leu Val Ser Leu Ala Ala Val Val Asn Pro Ser
            2450                2455                2460

Val Lys Thr Val Arg Glu Ala Gly Ile Leu Ile Thr Ala Ala Ala Val
2465                2470                2475                2480

Thr Leu Trp Glu Asn Gly Ala Ser Ser Val Trp Asn Ala Thr Thr Ala
            2485                2490                2495

Ile Gly Leu Cys His Ile Met Arg Gly Gly Trp Leu Ser Cys Leu Ser
            2500                2505                2510

Ile Thr Trp Thr Leu Ile Lys Asn Met Glu Lys Pro Gly Leu Lys Arg
            2515                2520                2525

Gly Gly Ala Lys Gly Arg Thr Leu Gly Glu Val Trp Lys Glu Arg Leu
            2530                2535                2540

Asn Gln Met Thr Lys Glu Glu Phe Thr Arg Tyr Arg Lys Glu Ala Ile
2545                2550                2555                2560

Ile Glu Val Asp Arg Ser Ala Ala Lys His Ala Arg Lys Glu Gly Asn
            2565                2570                2575

Val Thr Gly Gly His Pro Val Ser Arg Gly Thr Ala Lys Leu Arg Trp
            2580                2585                2590

Leu Val Glu Arg Arg Phe Leu Glu Pro Val Gly Lys Val Ile Asp Leu
            2595                2600                2605

Gly Cys Gly Arg Gly Gly Trp Cys Tyr Tyr Met Ala Thr Gln Lys Arg
            2610                2615                2620

Val Gln Glu Val Arg Gly Tyr Thr Lys Gly Gly Pro Gly His Glu Glu
2625                2630                2635                2640

Pro Gln Leu Val Gln Ser Tyr Gly Trp Asn Ile Val Thr Met Lys Ser
            2645                2650                2655

Gly Val Asp Val Phe Tyr Arg Pro Ser Glu Cys Cys Asp Thr Leu Leu
            2660                2665                2670

Cys Asp Ile Gly Glu Ser Ser Ser Ser Ala Glu Val Glu Glu His Arg
            2675                2680                2685

Thr Ile Arg Val Leu Glu Met Val Glu Asp Trp Leu His Arg Gly Pro
            2690                2695                2700

Arg Glu Phe Cys Val Lys Val Leu Cys Pro Tyr Met Pro Lys Val Ile
2705                2710                2715                2720

Glu Lys Met Glu Leu Leu Gln Arg Arg Tyr Gly Gly Gly Leu Val Arg
            2725                2730                2735

Asn Pro Leu Ser Arg Asn Ser Thr His Glu Met Tyr Trp Val Ser Arg
            2740                2745                2750

Ala Ser Gly Asn Val Val His Ser Val Asn Met Thr Ser Gln Val Leu
            2755                2760                2765

Leu Gly Arg Met Glu Lys Arg Thr Trp Lys Gly Pro Gln Tyr Glu Glu
            2770                2775                2780

Asp Val Asn Leu Gly Ser Gly Thr Arg Ala Val Gly Lys Pro Leu Leu
2785                2790                2795                2800

Asn Ser Asp Thr Ser Lys Ile Lys Asn Arg Ile Glu Arg Leu Arg Arg
            2805                2810                2815

Glu Tyr Ser Ser Thr Trp His His Asp Glu Asn His Pro Tyr Arg Thr
            2820                2825                2830

Trp Asn Tyr His Gly Ser Tyr Asp Val Lys Pro Thr Gly Ser Ala Ser
```

-continued

```
                2835                2840                2845
Ser Leu Val Asn Gly Val Arg Leu Leu Ser Lys Pro Trp Asp Thr
        2850                2855                2860
Ile Thr Asn Val Thr Thr Met Ala Met Thr Asp Thr Thr Pro Phe Gly
2865                2870                2875                2880
Gln Gln Arg Val Phe Lys Glu Lys Val Asp Thr Lys Ala Pro Glu Pro
                2885                2890                2895
Pro Glu Gly Val Lys Tyr Val Leu Asn Glu Thr Thr Asn Trp Leu Trp
            2900                2905                2910
Ala Phe Leu Ala Arg Glu Lys Arg Pro Arg Met Cys Ser Arg Glu Glu
            2915                2920                2925
Phe Ile Arg Lys Val Asn Ser Asn Ala Ala Leu Gly Ala Met Phe Glu
            2930                2935                2940
Glu Gln Asn Gln Trp Arg Ser Ala Arg Glu Ala Val Glu Asp Pro Lys
2945                2950                2955                2960
Phe Trp Glu Met Val Asp Glu Glu Arg Glu Ala His Leu Arg Gly Glu
                2965                2970                2975
Cys His Thr Cys Ile Tyr Asn Met Met Gly Lys Arg Glu Lys Lys Pro
            2980                2985                2990
Gly Glu Phe Gly Lys Ala Lys Gly Ser Arg Ala Ile Trp Phe Met Trp
            2995                3000                3005
Leu Gly Ala Arg Phe Leu Glu Phe Glu Ala Leu Gly Phe Leu Asn Glu
            3010                3015                3020
Asp His Trp Leu Gly Arg Lys Asn Ser Gly Gly Gly Val Glu Gly Leu
3025                3030                3035                3040
Gly Leu Gln Lys Leu Gly Tyr Ile Leu Arg Glu Val Gly Thr Arg Pro
            3045                3050                3055
Gly Gly Lys Ile Tyr Ala Asp Asp Thr Ala Gly Trp Asp Thr Arg Ile
            3060                3065                3070
Thr Arg Ala Asp Leu Glu Asn Glu Ala Lys Val Leu Glu Leu Leu Asp
            3075                3080                3085
Gly Glu His Arg Arg Leu Ala Arg Ala Ile Ile Glu Leu Thr Tyr Arg
            3090                3095                3100
His Lys Val Val Lys Val Met Arg Pro Ala Ala Asp Gly Arg Thr Val
3105                3110                3115                3120
Met Asp Val Ile Ser Arg Glu Asp Gln Arg Gly Ser Gly Gln Val Val
                3125                3130                3135
Thr Tyr Ala Leu Asn Thr Phe Thr Asn Leu Ala Val Gln Leu Val Arg
            3140                3145                3150
Met Met Glu Gly Glu Gly Val Ile Gly Pro Asp Asp Val Glu Lys Leu
            3155                3160                3165
Thr Lys Gly Lys Gly Pro Lys Val Arg Thr Trp Leu Phe Glu Asn Gly
            3170                3175                3180
Glu Glu Arg Leu Ser Arg Met Ala Val Ser Gly Asp Asp Cys Val Val
3185                3190                3195                3200
Lys Pro Leu Asp Asp Arg Phe Ala Thr Ser Leu His Phe Leu Asn Ala
            3205                3210                3215
Met Ser Lys Val Arg Lys Asp Ile Gln Glu Trp Lys Pro Ser Thr Gly
            3220                3225                3230
Trp Tyr Asp Trp Gln Gln Val Pro Phe Cys Ser Asn His Phe Thr Glu
            3235                3240                3245
Leu Ile Met Lys Asp Gly Arg Thr Leu Val Val Pro Cys Arg Gly Gln
            3250                3255                3260
```

```
Asp Glu Leu Val Gly Arg Ala Arg Ile Ser Pro Gly Ala Gly Trp Asn
3265                3270                3275                3280

Val Arg Asp Thr Ala Cys Leu Ala Lys Ser Tyr Ala Gln Met Trp Leu
            3285                3290                3295

Leu Leu Tyr Phe His Arg Arg Asp Leu Arg Leu Met Ala Asn Ala Ile
        3300                3305                3310

Cys Ser Ala Val Pro Val Asn Trp Val Pro Thr Gly Arg Thr Thr Trp
        3315                3320                3325

Ser Ile His Ala Gly Gly Glu Trp Met Thr Thr Glu Asp Met Leu Glu
        3330                3335                3340

Val Trp Asn Arg Val Trp Ile Glu Glu Asn Glu Trp Met Glu Asp Lys
3345                3350                3355                3360

Thr Pro Val Glu Lys Trp Ser Asp Val Pro Tyr Ser Gly Lys Arg Glu
            3365                3370                3375

Asp Ile Trp Cys Gly Ser Leu Ile Gly Thr Arg Ala Arg Ala Thr Trp
            3380                3385                3390

Ala Glu Asn Ile Gln Val Ala Ile Asn Gln Val Arg Ala Ile Ile Gly
            3395                3400                3405

Asp Glu Lys Tyr Val Asp Tyr Met Ser Ser Leu Lys Arg Tyr Glu Asp
        3410                3415                3420

Thr Thr Leu Val Glu Asp Thr Val Leu
3425                3430

<210> SEQ ID NO 3
<211> LENGTH: 251
<212> TYPE: PRT
<213> ORGANISM: Langat virus

<400> SEQUENCE: 3

Asn Glu Met Gly Leu Leu Glu Lys Thr Lys Ala Asp Leu Ala Ala Leu
1               5                   10                  15

Phe Ala Arg Asp Gln Gly Glu Thr Val Arg Trp Gly Glu Trp Thr Asn
            20                  25                  30

Leu Asp Ile Gln Pro Ala Arg Ser Trp Gly Thr Tyr Val Leu Val Val
        35                  40                  45

Ser Leu Phe Thr Pro Tyr Met Leu His Gln Leu Gln Thr Arg Ile Gln
    50                  55                  60

Gln Leu Val Asn Ser Ala Val Ala Ser Gly Ala Gln Ala Met Arg Asp
65                  70                  75                  80

Leu Gly Gly Gly Thr Pro Phe Phe Gly Val Ala Gly His Val Leu Ala
                85                  90                  95

Leu Gly Ile Ala Ser Leu Val Gly Ala Thr Pro Thr Ser Leu Ile Leu
            100                 105                 110

Gly Val Gly Leu Ala Ala Phe His Leu Ala Ile Val Val Ser Gly Leu
        115                 120                 125

Glu Ala Glu Leu Thr Gln Arg Ala His Lys Val Phe Phe Ser Ala Met
    130                 135                 140

Val Arg Asn Pro Met Val Asp Gly Asp Val Ile Asn Pro Phe Gly Asp
145                 150                 155                 160

Gly Glu Ala Lys Pro Ala Leu Tyr Glu Arg Lys Leu Ser Leu Ile Leu
                165                 170                 175

Ala Leu Val Leu Cys Leu Ala Ser Trp Met Asn Arg Thr Phe Val Ala
            180                 185                 190

Val Thr Glu Ala Gly Ala Val Gly Val Ala Ala Ala Met Gln Leu Leu
        195                 200                 205
```

```
Arg Pro Glu Met Asp Val Leu Trp Thr Met Pro Val Ala Cys Gly Met
        210                 215                 220

Ser Gly Val Val Arg Gly Ser Leu Trp Gly Leu Leu Pro Leu Gly His
225                 230                 235                 240

Arg Leu Trp Leu Arg Thr Thr Gly Thr Arg Arg
                245                 250

<210> SEQ ID NO 4
<211> LENGTH: 252
<212> TYPE: PRT
<213> ORGANISM: Tick-borne encephalitis virus

<400> SEQUENCE: 4

Asn Glu Met Gly Phe Leu Glu Lys Thr Lys Ala Asp Leu Ser Thr Ala
1               5                   10                  15

Leu Trp Ser Glu Arg Glu Pro Arg Pro Trp Ser Glu Trp Thr Asn
        20                  25                  30

Val Asp Ile Gln Pro Ala Arg Ser Trp Gly Thr Tyr Val Leu Val Val
            35                  40                  45

Ser Leu Phe Thr Pro Tyr Ile Ile His Gln Leu Gln Thr Lys Ile Gln
    50                  55                  60

Gln Leu Val Asn Ser Ala Val Ala Ser Gly Ala Gln Ala Met Arg Asp
65                  70                  75                  80

Leu Gly Gly Gly Ala Pro Phe Phe Gly Val Ala Gly His Val Met Thr
                85                  90                  95

Leu Gly Val Val Ser Leu Ile Gly Ala Thr Pro Thr Ser Leu Met Val
            100                 105                 110

Gly Val Gly Leu Ala Ala Leu His Leu Ala Ile Val Val Ser Gly Leu
        115                 120                 125

Glu Ala Glu Leu Thr Cys Arg Ala His Lys Val Phe Phe Ser Ala Met
    130                 135                 140

Val Arg Asn Pro Met Val Asp Gly Asp Val Ile Asn Pro Phe Gly Glu
145                 150                 155                 160

Gly Glu Ala Lys Pro Ala Leu Tyr Glu Arg Lys Met Ser Leu Val Leu
                165                 170                 175

Ala Thr Val Leu Cys Leu Met Ser Val Val Met Asn Arg Thr Val Ala
            180                 185                 190

Ser Ile Thr Glu Ala Ser Ala Val Gly Leu Ala Ala Ala Gly Gln Leu
        195                 200                 205

Leu Arg Pro Glu Ala Asp Thr Leu Trp Thr Met Pro Val Ala Cys Gly
    210                 215                 220

Met Ser Gly Val Val Arg Gly Ser Leu Trp Gly Phe Leu Pro Leu Gly
225                 230                 235                 240

His Arg Leu Trp Leu Arg Ala Ser Gly Gly Arg Arg
                245                 250

<210> SEQ ID NO 5
<211> LENGTH: 250
<212> TYPE: PRT
<213> ORGANISM: Powassan virus

<400> SEQUENCE: 5

Asn Glu Leu Gly Tyr Leu Glu Gln Thr Lys Thr Asp Ile Ser Gly Leu
1               5                   10                  15

Phe Arg Arg Glu Asp Gln Gly Gly Met Val Trp Asp Ala Trp Thr Asn
        20                  25                  30

Ile Asp Ile Gln Pro Ala Arg Ser Trp Gly Thr Tyr Val Leu Ile Val
```

```
                35                  40                  45
Ser Leu Phe Thr Pro Tyr Met Leu His Gln Leu Gln Thr Lys Ile Gln
 50                  55                  60

Arg Leu Val Asn Ser Ser Val Ala Ala Gly Thr Gln Ala Met Arg Asp
 65                  70                  75                  80

Leu Gly Gly Gly Thr Pro Phe Phe Gly Val Ala Gly His Trp Ala Leu
                85                  90                  95

Gly Val Thr Ser Leu Val Gly Ala Thr Pro Thr Ser Leu Ala Leu Gly
                100                 105                 110

Val Ala Leu Ala Ala Leu His Leu Ala Trp Thr Ser Gly Leu Glu Ala
                115                 120                 125

Glu Leu Thr Gln Arg Ala His Arg Ala Phe Phe Ser Ala Met Val Lys
                130                 135                 140

Asn Pro Met Val Asp Gly Glu Ile Ile Asn Pro Ile Pro Asp Gly Asp
145                 150                 155                 160

Pro Lys Pro Ala Leu Tyr Glu Arg Lys Met Ser Leu Phe Leu Ala Ile
                165                 170                 175

Gly Leu Cys Ile Ala Ala Val Ala Leu Asn Arg Thr Ala Ala Ala Met
                180                 185                 190

Thr Glu Ala Gly Ala Val Ala Val Ala Ala Leu Gly Gln Leu Leu Arg
                195                 200                 205

Pro Glu Glu Glu Ser Trp Trp Thr Met Pro Met Ala Cys Gly Met Ala
                210                 215                 220

Gly Leu Val Arg Gly Ser Leu Trp Gly Leu Leu Pro Val Leu His Arg
225                 230                 235                 240

Ile Trp Leu Arg Thr Gln Gly Ala Arg Arg
                245                 250

<210> SEQ ID NO 6
<211> LENGTH: 251
<212> TYPE: PRT
<213> ORGANISM: Omsk hemorrhagic fever virus

<400> SEQUENCE: 6

Asn Glu Met Gly Phe Leu Glu Lys Thr Lys Ala Asp Leu Ser Ala Val
 1                   5                  10                  15

Leu Trp Ser Glu Arg Glu Pro Arg Val Trp Ser Glu Trp Thr Asn
                20                  25                  30

Ile Asp Ile Gln Pro Ala Lys Ser Trp Gly Thr Tyr Val Leu Val Val
                35                  40                  45

Ser Leu Phe Thr Pro Tyr Ile Ile His Gln Leu Gln Thr Arg Ile Gln
 50                  55                  60

Gln Leu Val Asn Ser Ala Val Ala Ser Gly Ala Gln Ala Met Arg Asp
 65                  70                  75                  80

Leu Gly Gly Gly Thr Pro Phe Phe Gly Val Ala Gly His Val Leu Thr
                85                  90                  95

Leu Gly Val Val Ser Leu Val Gly Ala Thr Pro Thr Ser Leu Val Val
                100                 105                 110

Gly Val Gly Leu Ala Ala Phe His Leu Ala Ile Val Val Ser Gly Leu
                115                 120                 125

Glu Ala Glu Leu Thr Cys Arg Ala His Lys Val Phe Phe Ser Ala Met
                130                 135                 140

Val Arg Asn Pro Met Val Asp Gly Asp Val Ile Asn Pro Phe Gly Asp
145                 150                 155                 160

Gly Glu Val Lys Pro Ala Leu Tyr Glu Arg Lys Met Ser Leu Ile Leu
```

Ala Met Ile Leu Cys Phe Met Ser Trp Leu Asn Arg Thr Val Pro Ala
            180                 185                 190

Val Thr Glu Ala Ser Ala Val Gly Leu Ala Ala Gly Gln Leu Ile
        195                 200                 205

Arg Pro Glu Ala Asp Thr Leu Trp Thr Met Pro Val Ala Cys Gly Leu
            210                 215                 220

Ser Gly Val Val Arg Gly Ser Leu Trp Gly Phe Leu Pro Leu Gly His
225                 230                 235                 240

Arg Leu Trp Leu Arg Thr Ser Gly Thr Arg Arg
                245                 250

<210> SEQ ID NO 7
<211> LENGTH: 250
<212> TYPE: PRT
<213> ORGANISM: Yellow fever virus

<400> SEQUENCE: 7

Asn Glu Leu Gly Met Leu Glu Lys Thr Lys Glu Asp Leu Phe Gly Lys
1               5                   10                  15

Lys Asn Leu Ile Pro Ser Ser Ala Ser Pro Trp Ser Trp Pro Asp Leu
            20                  25                  30

Asp Leu Lys Pro Gly Ala Ala Trp Thr Val Tyr Val Gly Ile Val Thr
        35                  40                  45

Met Leu Ser Pro Met Leu His His Trp Ile Lys Val Glu Tyr Gly Asn
    50                  55                  60

Leu Ser Leu Ser Gly Ile Ala Gln Ser Ala Ser Val Leu Ser Phe Met
65                  70                  75                  80

Asp Lys Gly Ile Pro Phe Met Lys Met Asn Ile Ser Val Ile Ile Leu
                85                  90                  95

Leu Val Ser Gly Trp Asn Ser Ile Thr Val Met Pro Leu Leu Cys Gly
            100                 105                 110

Ile Gly Cys Ala Met Leu His Trp Ser Leu Ile Leu Pro Gly Ile Lys
        115                 120                 125

Ala Cys Cys Ser Lys Leu Ala Gln Arg Arg Val Phe His Gly Val Ala
    130                 135                 140

Lys Asn Pro Val Val Asp Gly Asn Pro Thr Val Asp Ile Glu Glu Ala
145                 150                 155                 160

Pro Glu Met Pro Ala Leu Tyr Glu Lys Lys Leu Ala Leu Tyr Leu Leu
                165                 170                 175

Leu Ala Leu Ser Leu Ala Ser Val Ala Met Cys Arg Thr Pro Phe Ser
            180                 185                 190

Leu Ala Glu Gly Ile Val Leu Ala Ser Ala Ala Leu Gly Pro Leu Ile
        195                 200                 205

Glu Gly Asn Thr Ser Leu Leu Trp Asn Gly Pro Met Ala Val Ser Met
    210                 215                 220

Thr Gly Val Met Arg Gly Asn Tyr Tyr Ala Glu Val Gly Val Met Tyr
225                 230                 235                 240

Asn Leu Trp Lys Met Lys Thr Gly Arg Arg
                245                 250

<210> SEQ ID NO 8
<211> LENGTH: 248
<212> TYPE: PRT
<213> ORGANISM: Yellow fever virus

<400> SEQUENCE: 8

Asn Glu Leu Gly Met Leu Glu Lys Thr Lys Glu Asp Leu Phe Gly Lys
1               5                   10                  15

Lys Asn Leu Ile Pro Ser Ser Ala Ser Pro Trp Ser Trp Pro Asp Leu
                20                  25                  30

Asp Leu Lys Pro Gly Ala Ala Trp Thr Val Tyr Val Gly Ile Val Thr
            35                  40                  45

Met Leu Ser Pro Met Leu His His Trp Ile Lys Val Glu Tyr Gly Asn
50                  55                  60

Leu Ser Leu Ser Gly Ile Ala Gln Ser Ala Ser Val Leu Ser Phe Met
65                  70                  75                  80

Asp Lys Gly Ile Pro Phe Met Lys Met Asn Ile Ser Val Ile Met Leu
                85                  90                  95

Leu Val Ser Gly Trp Asn Ser Ile Thr Val Met Pro Leu Leu Cys Gly
                100                 105                 110

Ile Gly Cys Ala Met Leu His Trp Ser Leu Ile Leu Pro Gly Ile Lys
            115                 120                 125

Ala Gln Cys Ser Lys Leu Ala Gln Arg Arg Val Phe His Gly Val Ala
130                 135                 140

Glu Asn Pro Trp Asp Gly Asn Pro Thr Val Asp Ile Glu Glu Ala Pro
145                 150                 155                 160

Glu Met Pro Ala Leu Tyr Glu Lys Lys Leu Ala Leu Tyr Leu Leu Leu
                165                 170                 175

Ala Leu Ser Leu Ala Ser Val Ala Met Cys Arg Thr Pro Ser Leu Ala
            180                 185                 190

Glu Gly Ile Val Leu Ala Ser Ala Ala Leu Gly Pro Leu Ile Glu Gly
            195                 200                 205

Asn Thr Ser Leu Leu Trp Asn Gly Pro Met Ala Val Ser Met Thr Gly
            210                 215                 220

Val Met Arg Gly Asn His Tyr Ala Phe Val Gly Val Met Tyr Asn Leu
225                 230                 235                 240

Trp Lys Met Lys Thr Gly Arg Arg
                245

<210> SEQ ID NO 9
<211> LENGTH: 248
<212> TYPE: PRT
<213> ORGANISM: Dengue virus type 1

<400> SEQUENCE: 9

Asn Glu Met Gly Leu Leu Glu Thr Thr Lys Lys Asp Leu Gly Ile Gly
1               5                   10                  15

His Val Ala Ala Glu Asn Gln His His Ala Thr Met Leu Asp Val Asp
                20                  25                  30

Leu Arg Pro Ala Ser Ala Trp Thr Leu Tyr Ala Val Ala Thr Thr Val
            35                  40                  45

Ile Thr Pro Met Met Arg His Thr Ile Glu Asn Thr Thr Ala Asn Ile
            50                  55                  60

Ser Leu Thr Ala Ile Ala Asn Gln Ala Ala Ile Leu Met Gly Leu Asp
65                  70                  75                  80

Lys Gly Trp Pro Ile Ser Lys Met Asp Ile Gly Val Pro Leu Leu Ala
                85                  90                  95

Leu Gly Cys Tyr Ser Cys Val Asn Pro Leu Thr Leu Thr Ala Ala Val
            100                 105                 110

Leu Met Leu Val Ala His Tyr Ala Ile Ile Gly Pro Gly Leu Cys Ala
            115                 120                 125

```
Lys Ala Thr Arg Glu Ala Gln Lys Arg Thr Ala Ala Gly Ile Met Lys
        130                 135                 140

Asn Pro Thr Val Asp Gly Ile Val Ala Ile Asp Leu Asp Pro Trp Tyr
145                 150                 155                 160

Asp Ala Lys Phe Glu Lys Gln Leu Gly Gln Ile Met Leu Leu Ile Leu
                165                 170                 175

Cys Thr Ser Gln Ile Leu Leu Met Arg Thr Thr Trp Ala Leu Cys Glu
            180                 185                 190

Ser Ile Thr Leu Ala Thr Gly Pro Leu Thr Thr Leu Trp Glu Gly Ser
        195                 200                 205

Pro Gly Lys Phe Trp Asn Thr Thr Ile Ala Val Ser Met Ala Asn Ile
210                 215                 220

Phe Arg Gly Ser Tyr Leu Ala Gly Ala Gly Leu Ala Phe Ser Leu Met
225                 230                 235                 240

Lys Ser Leu Gly Gly Gly Arg Arg
                245

<210> SEQ ID NO 10
<211> LENGTH: 248
<212> TYPE: PRT
<213> ORGANISM: Dengue virus type 3

<400> SEQUENCE: 10

Asn Glu Met Gly Leu Leu Glu Thr Thr Lys Arg Asp Leu Gly Met Ser
1               5                   10                  15

Lys Glu Pro Gly Val Val Ser Pro Thr Ser Tyr Leu Asp Val Asp Leu
            20                  25                  30

His Pro Ala Ser Ala Trp Thr Leu Tyr Ala Val Ala Thr Thr Val Ile
        35                  40                  45

Thr Pro Met Leu Arg His Thr Ile Glu Asn Ser Thr Ala Asn Val Ser
    50                  55                  60

Leu Ala Ala Ile Ala Asn Gln Ala Val Val Leu Met Gly Leu Asp Lys
65                  70                  75                  80

Gly Trp Pro Ile Ser Lys Met Asp Leu Gly Val Pro Leu Leu Ala Leu
                85                  90                  95

Gly Cys Tyr Ser Cys Val Asn Pro Leu Thr Leu Ile Ala Ala Val Leu
            100                 105                 110

Leu Leu Val Thr His Tyr Ala Ile Ile Gly Pro Gly Leu Cys Ala Lys
        115                 120                 125

Ala Thr Arg Glu Ala Gln Lys Arg Thr Ala Ala Gly Ile Met Lys Asn
    130                 135                 140

Pro Thr Val Asp Gly Ile Met Thr Ile Asp Leu Asp Pro Val Ile Tyr
145                 150                 155                 160

Asp Pro Lys Phe Glu Lys Gln Leu Gly Gln Val Met Leu Leu Val Leu
                165                 170                 175

Cys Ala Val Gln Leu Leu Met Arg Thr Ser Trp Ala Leu Cys Glu
            180                 185                 190

Val Leu Thr Leu Ala Thr Gly Pro Ile Thr Thr Leu Trp Glu Gly Ser
        195                 200                 205

Pro Gly Lys Phe Trp Asn Thr Thr Ile Ala Val Ser Met Ala Asn Ile
210                 215                 220

Phe Arg Gly Ser Tyr Leu Ala Gly Ala Gly Leu Ala Leu Ser Ile Met
225                 230                 235                 240

Lys Ser Val Gly Thr Gly Lys Arg
                245
```

<210> SEQ ID NO 11
<211> LENGTH: 248
<212> TYPE: PRT
<213> ORGANISM: Dengue virus type 2

<400> SEQUENCE: 11

Asn Glu Met Gly Phe Leu Glu Lys Thr Lys Lys Asp Leu Gly Leu Gly
1               5                   10                  15

Asn Ile Ala Thr Gln Gln Pro Glu Ser Asn Ile Leu Asp Ile Asp Leu
            20                  25                  30

Arg Pro Ala Ser Ala Trp Thr Leu Tyr Ala Val Ala Thr Thr Phe Ile
        35                  40                  45

Thr Pro Met Leu Arg His Ser Ile Glu Asn Ser Ser Val Asn Val Ser
    50                  55                  60

Leu Thr Ala Ile Ala Asn Gln Ala Thr Val Leu Met Gly Leu Gly Lys
65                  70                  75                  80

Gly Trp Pro Leu Ser Lys Met Asp Ile Gly Val Pro Leu Leu Ala Ile
                85                  90                  95

Gly Cys Tyr Ser Cys Val Asn Pro Ile Thr Leu Thr Ala Ala Leu Leu
            100                 105                 110

Leu Leu Val Ala His Tyr Ala Ile Ile Gly Pro Gly Leu Cys Ala Lys
        115                 120                 125

Ala Thr Arg Glu Ala Gln Lys Arg Ala Ala Ala Gly Ile Met Lys Asn
    130                 135                 140

Pro Thr Val Asp Gly Ile Thr Val Ile Asp Leu Asp Pro Ile Pro Tyr
145                 150                 155                 160

Asp Pro Lys Phe Glu Lys Gln Leu Gly Gln Val Met Leu Leu Val Leu
                165                 170                 175

Cys Val Thr Gln Val Leu Met Met Arg Thr Thr Trp Ala Leu Cys Glu
            180                 185                 190

Ala Leu Thr Leu Ala Thr Gly Pro Val Ser Thr Leu Trp Glu Gly Asn
        195                 200                 205

Pro Gly Arg Phe Trp Asn Thr Thr Ile Ala Val Ser Met Ala Asn Ile
    210                 215                 220

Phe Arg Gly Ser Tyr Leu Ala Gly Ala Gly Leu Leu Phe Ser Ile Met
225                 230                 235                 240

Lys Asn Thr Thr Ser Thr Arg Arg
                245

<210> SEQ ID NO 12
<211> LENGTH: 245
<212> TYPE: PRT
<213> ORGANISM: Dengue virus type 4

<400> SEQUENCE: 12

Asn Glu Met Gly Leu Ile Glu Lys Thr Lys Thr Asp Phe Gly Phe Tyr
1               5                   10                  15

Gln Val Lys Thr Glu Thr Thr Ile Leu Asp Val Asp Leu Arg Pro Ala
            20                  25                  30

Ser Ala Trp Thr Leu Tyr Ala Val Ala Thr Thr Ile Leu Thr Pro Met
        35                  40                  45

Leu Arg His Thr Ile Glu Asn Thr Ser Ala Asn Leu Ser Leu Ala Ala
    50                  55                  60

Ile Ala Asn Gln Ala Ala Val Leu Met Gly Leu Gly Lys Gly Trp Pro
65                  70                  75                  80

```
Leu His Arg Met Asp Leu Gly Val Pro Leu Leu Ala Met Gly Cys Tyr
                85                  90                  95
Ser Cys Val Asn Pro Thr Thr Leu Thr Ala Ser Leu Val Met Leu Leu
            100                 105                 110
Val His Tyr Ala Ile Ile Gly Pro Gly Leu Cys Ala Lys Ala Thr Arg
        115                 120                 125
Glu Ala Gln Lys Arg Thr Ala Ala Gly Ile Met Lys Asn Pro Thr Val
    130                 135                 140
Asp Gly Ile Thr Val Ile Asp Leu Phe Pro Ile Ser Tyr Asp Pro Lys
145                 150                 155                 160
Phe Glu Lys Gln Leu Gly Gln Val Met Leu Leu Val Leu Cys Ala Gly
                165                 170                 175
Gln Leu Leu Leu Met Arg Thr Thr Trp Ala Phe Cys Glu Val Leu Thr
            180                 185                 190
Leu Ala Thr Gly Pro Ile Leu Thr Leu Trp Glu Gly Asn Pro Gly Arg
        195                 200                 205
Phe Trp Asn Thr Thr Ile Ala Val Ser Thr Ala Asn Ile Phe Arg Gly
    210                 215                 220
Ser Tyr Leu Ala Gly Ala Gly Leu Ala Phe Ser Leu Ile Lys Asn Ala
225                 230                 235                 240
Gln Thr Pro Arg Arg
                245

<210> SEQ ID NO 13
<211> LENGTH: 255
<212> TYPE: PRT
<213> ORGANISM: Japanese encephalitis virus

<400> SEQUENCE: 13

Asn Glu Tyr Gly Met Leu Glu Lys Thr Lys Ala Asp Leu Lys Ser Met
1               5                   10                  15
Phe Val Gly Lys Thr Gln Ala Ser Gly Leu Thr Gly Leu Pro Ser Met
            20                  25                  30
Ala Leu Asp Leu Arg Pro Ala Thr Ala Trp Ala Leu Tyr Gly Gly Ser
        35                  40                  45
Thr Val Val Leu Thr Pro Leu Leu Lys His Leu Ile Thr Ser Glu Tyr
    50                  55                  60
Val Thr Thr Ser Leu Ala Ser Ile Asn Ser Gln Ala Gly Ser Leu Phe
65                  70                  75                  80
Val Leu Pro Arg Gly Val Pro Phe Thr Asp Leu Asp Leu Thr Val Gly
                85                  90                  95
Leu Val Phe Leu Gly Cys Trp Gly Cys Ile Thr Leu Thr Thr Phe Leu
            100                 105                 110
Thr Ala Met Val Leu Ala Thr Leu His Tyr Gly Tyr Met Leu Pro Gly
        115                 120                 125
Trp Gln Ala Glu Ala Leu Arg Ala Ala Gln Arg Arg Thr Ala Ala Gly
    130                 135                 140
Ile Met Lys Asn Ala Val Val Asp Gly Met Val Ala Thr Asp Val Pro
145                 150                 155                 160
Glu Leu Glu Arg Thr Thr Pro Leu Met Gln Lys Lys Val Gly Gln Val
                165                 170                 175
Leu Leu Ile Gly Val Ser Val Ala Ala Phe Leu Val Asn Pro Asn Val
            180                 185                 190
Thr Thr Val Arg Glu Ala Gly Val Leu Val Thr Ala Ala Thr Leu Thr
        195                 200                 205
```

```
Leu Trp Asp Asn Gly Ala Ser Ala Val Trp Asn Ser Thr Thr Ala Thr
            210                 215                 220

Gly Leu Cys His Val Met Arg Gly Ser Tyr Leu Ala Gly Gly Ser Ile
225                 230                 235                 240

Ala Trp Thr Leu Ile Lys Asn Ala Asp Lys Pro Ser Leu Lys Arg
                245                 250                 255
```

<210> SEQ ID NO 14
<211> LENGTH: 257
<212> TYPE: PRT
<213> ORGANISM: Murray Valley encephalitis virus

<400> SEQUENCE: 14

```
Asn Glu Tyr Gly Met Leu Glu Arg Thr Lys Thr Asp Ile Arg Asn Leu
1               5                   10                  15

Phe Gly Lys Ser Leu Ile Glu Glu Asn Glu Val His Ile Pro Pro Phe
            20                  25                  30

Asp Phe Phe Thr Leu Asp Leu Lys Pro Ala Thr Ala Trp Ala Leu Tyr
        35                  40                  45

Gly Gly Ser Thr Val Val Leu Thr Pro Leu Ile Lys His Leu Val Thr
50                  55                  60

Ser Gln Tyr Val Thr Thr Ser Leu Ala Ser Ile Asn Ala Gln Ala Gly
65                  70                  75                  80

Ser Leu Phe Thr Leu Pro Lys Gly Ile Pro Phe Thr Asp Phe Asp Leu
                85                  90                  95

Ser Val Ala Leu Val Phe Leu Gly Cys Trp Gly Gln Val Thr Leu Thr
            100                 105                 110

Thr Leu Ile Met Ala Thr Ile Leu Val Thr Leu His Tyr Gly Tyr Leu
        115                 120                 125

Leu Pro Gly Trp Cys Ala Glu Ala Leu Arg Ala Ala Gln Lys Arg Thr
130                 135                 140

Ala Ala Gly Ile Met Lys Asn Ala Trp Asp Gly Ile Val Ala Thr Asp
145                 150                 155                 160

Val Pro Glu Leu Glu Arg Thr Thr Pro Gln Met Gln Lys Arg Leu Gly
                165                 170                 175

Gln Ile Leu Leu Val Leu Ala Ser Val Ala Ala Val Cys Val Asn Pro
            180                 185                 190

Arg Ile Thr Thr Ile Arg Glu Ala Gly Ile Leu Cys Thr Ala Ala Ala
        195                 200                 205

Leu Thr Leu Trp Asp Asn Asn Ala Ser Ala Ala Trp Asn Ser Thr Thr
210                 215                 220

Ala Thr Gly Leu Cys His Val Met Arg Gly Ser Trp Ile Ala Gly Ala
225                 230                 235                 240

Ser Ile Ala Trp Thr Leu Ile Lys Asn Ala Glu Lys Pro Ala Phe Lys
                245                 250                 255

Arg
```

<210> SEQ ID NO 15
<211> LENGTH: 255
<212> TYPE: PRT
<213> ORGANISM: Kunjin virus

<400> SEQUENCE: 15

```
Asn Glu Met Gly Trp Leu Asp Lys Thr Lys Ser Asp Ile Ser Gly Leu
1               5                   10                  15

Phe Gly Gln Arg Ile Glu Thr Lys Glu Asn Phe Ser Ile Gly Glu Phe
            20                  25                  30
```

```
Leu Leu Asp Leu Arg Pro Ala Thr Ala Trp Ser Leu Tyr Ala Val Thr
            35                  40                  45

Thr Ala Val Leu Thr Pro Leu Leu Lys His Leu Ile Thr Ser Asp Tyr
 50                  55                  60

Ile Asn Thr Ser Leu Thr Ser Ile Asn Val Gln Ala Ser Ala Leu Phe
 65                  70                  75                  80

Thr Leu Ala Arg Gly Phe Pro Phe Val Asp Val Gly Val Ser Ala Leu
                85                  90                  95

Leu Leu Ala Ala Gly Cys Trp Gly Cys Val Thr Leu Thr Val Thr Val
            100                 105                 110

Thr Ser Ala Thr Leu Leu Phe Cys His Tyr Ala Tyr Met Val Pro Gly
        115                 120                 125

Trp Cys Ala Glu Ala Met Arg Ser Ala Gln Arg Arg Thr Ala Ala Gly
    130                 135                 140

Ile Met Lys Asn Ala Val Val Asp Gly Ile Val Ala Thr Asp Val Pro
145                 150                 155                 160

Glu Leu Glu Arg Thr Thr Pro Ile Met Gln Lys Lys Val Gly Gln Val
                165                 170                 175

Met Leu Ile Leu Val Ser Leu Ala Ala Leu Val Val Asn Pro Ser Val
            180                 185                 190

Lys Thr Val Arg Glu Ala Gly Ile Leu Ile Thr Ala Ala Ala Val Thr
        195                 200                 205

Leu Trp Glu Asn Gly Ala Ser Ser Val Trp Asn Ala Thr Thr Ala Ile
    210                 215                 220

Gly Leu Cys His Ile Met Arg Gly Gly Trp Leu Ser Cys Leu Ser Ile
225                 230                 235                 240

Thr Trp Thr Leu Val Lys Asn Met Glu Lys Pro Gly Leu Lys Arg
                245                 250                 255

<210> SEQ ID NO 16
<211> LENGTH: 254
<212> TYPE: PRT
<213> ORGANISM: West Nile virus

<400> SEQUENCE: 16

Asn Glu Met Gly Trp Leu Asp Lys Thr Lys Ser Asp Ile Ser Ser Leu
 1               5                  10                  15

Phe Gly Gln Arg Ile Glu Val Lys Glu Asn Phe Ser Met Gly Glu Phe
                20                  25                  30

Leu Leu Asp Leu Arg Pro Ala Thr Ala Trp Ser Leu Tyr Ala Val Thr
            35                  40                  45

Thr Ala Val Leu Thr Pro Leu Leu Lys His Leu Ile Thr Ser Asp Tyr
 50                  55                  60

Ile Asn Thr Ser Leu Thr Ser Ile Asn Val Gln Ala Ser Ala Leu Phe
 65                  70                  75                  80

Thr Leu Ala Arg Gly Phe Pro Phe Val Asp Val Gly Val Ser Ala Leu
                85                  90                  95

Leu Leu Ala Ala Gly Cys Trp Gly Gln Val Thr Leu Thr Val Thr Val
            100                 105                 110

Thr Ala Ala Thr Leu Leu Phe Cys His Tyr Ala Tyr Met Val Pro Gly
        115                 120                 125

Trp Cys Ala Glu Ala Met Arg Ser Ala Gln Arg Arg Thr Ala Ala Gly
    130                 135                 140

Ile Met Lys Asn Ala Trp Asp Gly Ile Val Ala Thr Asp Val Pro Glu
145                 150                 155                 160
```

```
Leu Glu Arg Thr Thr Pro Ile Met Gln Lys Lys Val Gly Gln Ile Met
                165                 170                 175

Leu Ile Leu Val Ser Leu Ala Ala Val Val Asn Pro Ser Val Lys
            180                 185                 190

Thr Val Arg Glu Ala Gly Ile Leu Ile Thr Ala Ala Val Thr Leu
        195                 200                 205

Trp Glu Asn Gly Ala Ser Ser Val Trp Asn Ala Thr Thr Ala Ile Gly
    210                 215                 220

Leu Cys His Ile Met Arg Gly Gly Trp Leu Ser Cys Leu Ser Ile Thr
225                 230                 235                 240

Trp Thr Leu Ile Lys Asn Met Glu Lys Pro Gly Leu Lys Arg
                245                 250
```

<210> SEQ ID NO 17
<211> LENGTH: 258
<212> TYPE: PRT
<213> ORGANISM: Saint Louis encephalitis virus

<400> SEQUENCE: 17

```
Asn Glu Met Gly Leu Leu Glu Lys Thr Lys Ser Asp Ile Ala Lys Leu
1               5                   10                  15

Phe Gly Ser Gln Pro Gly Ser Val Gly Phe Ala Ile Arg Thr Thr Pro
            20                  25                  30

Trp Asp Ile Ser Leu Asp Ile Lys Pro Ala Thr Ala Trp Ala Leu Tyr
        35                  40                  45

Ala Ala Ala Thr Met Val Met Thr Pro Leu Ile Lys His Leu Ile Thr
    50                  55                  60

Thr Gln Tyr Val Asn Phe Ser Leu Thr Ala Ile Ala Ser Gln Ala Gly
65                  70                  75                  80

Val Leu Leu Gly Leu Thr Asn Gly Met Pro Phe Thr Ala Met Asp Leu
                85                  90                  95

Ser Val Pro Leu Leu Val Leu Gly Cys Trp Asn Gly Met Thr Leu Pro
            100                 105                 110

Ser Leu Ala Val Ala Val Met Leu Leu Ala Ile His Tyr Ala Phe Met
        115                 120                 125

Ile Pro Gly Trp Cys Ala Glu Ala Met Arg Ala Ala Gln Arg Arg Thr
    130                 135                 140

Ala Ala Gly Ile Met Lys Asn Ala Val Val Asp Gly Ile Val Ala Thr
145                 150                 155                 160

Asp Ile Pro Asp Leu Ser Pro Ala Thr Pro Met Thr Glu Lys Lys Met
                165                 170                 175

Gly Gln Ile Leu Leu Ile Ala Ala Ala Val Leu Ala Val Leu Val Arg
            180                 185                 190

Pro Gly Ile Cys Ser Ile Lys Glu Phe Gly Val Leu Gly Ser Ala Ala
        195                 200                 205

Leu Val Thr Leu Ile Glu Gly Thr Ala Gly Val Val Trp Asn Cys Thr
    210                 215                 220

Thr Ala Val Gly Leu Cys Asn Leu Met Arg Gly Gly Trp Leu Ala Gly
225                 230                 235                 240

Met Ser Ile Thr Trp Thr Val Tyr Lys Asn Val Asp Lys Pro Lys Gly
                245                 250                 255

Lys Arg
```

<210> SEQ ID NO 18
<211> LENGTH: 258

```
<212> TYPE: PRT
<213> ORGANISM: Usutu virus

<400> SEQUENCE: 18

Asn Glu Tyr Gly Met Leu Glu Arg Thr Lys Ser Asp Leu Gly Lys Ile
1               5                   10                  15

Phe Ser Ser Thr Arg Gln Pro Gln Ser Ala Leu Pro Leu Pro Ser Met
            20                  25                  30

Asn Ala Leu Ala Leu Asp Leu Arg Pro Ala Thr Ala Trp Ala Leu Tyr
        35                  40                  45

Gly Gly Ser Thr Val Val Leu Thr Pro Leu Ile Lys His Leu Val Thr
50                  55                  60

Ser Glu Tyr Ile Thr Thr Ser Leu Ala Ser Ile Ser Ala Gln Ala Gly
65                  70                  75                  80

Ser Leu Phe Asn Leu Pro Arg Gly Leu Pro Phe Thr Glu Leu Asp Phe
                85                  90                  95

Thr Val Val Leu Val Phe Leu Gly Cys Trp Gly Cys Val Ser Leu Thr
            100                 105                 110

Thr Leu Ile Thr Ala Ala Ala Leu Ala Thr Leu His Tyr Gly Tyr Met
        115                 120                 125

Leu Pro Gly Trp Cys Ala Glu Ala Leu Arg Ala Ala Gln Arg Arg Thr
130                 135                 140

Ala Ala Gly Ile Met Lys Asn Ala Val Val Asp Gly Leu Val Ala Thr
145                 150                 155                 160

Asp Val Pro Glu Leu Glu Arg Thr Thr Pro Leu Met Gln Lys Lys Val
                165                 170                 175

Gly Gln Ile Leu Leu Ile Gly Val Ser Ala Ala Ala Leu Leu Val Asn
            180                 185                 190

Pro Cys Val Thr Thr Val Arg Glu Ala Gly Ile Leu Ile Ser Ala Ala
        195                 200                 205

Leu Leu Thr Leu Trp Asp Asn Gly Ala Ile Ala Val Trp Asn Ser Thr
210                 215                 220

Thr Ala Thr Gly Leu Cys His Val Ile Arg Gly Asn Trp Leu Ala Gly
225                 230                 235                 240

Ala Ser Ile Ala Trp Thr Leu Ile Lys Asn Ala Asp Lys Pro Ala Cys
                245                 250                 255

Lys Arg

<210> SEQ ID NO 19
<211> LENGTH: 202
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Asn Glu Met Gly Leu Leu Glu Lys Thr Lys Ala Asp Leu Leu Phe Trp
1               5                   10                  15

Leu Asp Leu Arg Pro Ala Thr Ala Trp Ala Leu Tyr Ala Val Ala Thr
            20                  25                  30

Thr Val Leu Thr Pro Leu Leu Lys His Ile Ser Tyr Asn Leu Ser Leu
        35                  40                  45

Ser Ala Ile Ala Ser Gln Ala Ala Leu Leu Gly Lys Gly Pro Phe Met
    50                  55                  60

Asp Leu Ser Val Leu Leu Leu Ala Leu Gly Cys Trp Gln Val Thr Pro
65                  70                  75                  80
```

```
Thr Thr Leu Ile Ala Val Leu Ala Leu His Tyr Ala Ile Ile Leu Pro
            85                  90                  95

Gly Leu Cys Ala Glu Ala Thr Arg Ala Gln Lys Arg Thr Ala Ala Gly
            100                 105                 110

Ile Met Lys Asn Pro Val Val Asp Gly Ile Val Asp Val Glu Leu Glu
            115                 120                 125

Pro Leu Tyr Glu Lys Lys Leu Gly Gln Ile Leu Leu Leu Val Leu Cys
            130                 135                 140

Leu Ala Ala Val Leu Val Asn Arg Thr Val Ala Val Glu Ala Gly Ile
145                 150                 155                 160

Leu Ala Thr Ala Ala Leu Leu Thr Leu Trp Glu Ala Leu Trp Asn Thr
                165                 170                 175

Ile Ala Val Gly Met Ala Val Met Arg Gly Ser Tyr Leu Ala Gly Leu
                180                 185                 190

Leu Ala Trp Thr Leu Ile Lys Asn Lys Arg
            195                 200

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 20
ccagaactcg ccgccaacac ctttgtgg                                          28

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 21
ggtcagagag agcgccacaa ctgaatgtga ctcg                                   34

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 22
ggattgaaag caggctcgct gatacgtgga agc                                    33
```

US 8,017,754 B2

ATTENUATED VIRUS STRAINS AND USES THEREOF

This application is a national phase application under 35 U.S.C. §371 of International Application No. PCT/US2006/027565 filed Jul. 14, 2006, which claims priority to U.S. Provisional Patent application Ser. No. 60/701,765 filed Jul. 22, 2005, the entire contents and disclosures of which are specifically incorporated by reference herein without disclaimer.

The United States government may own certain rights to this invention pursuant to grant number T32AI 7526 from the National Institutes of Health.

BACKGROUND OF THE INVENTION

1. Field of the Invention

The present invention generally concerns the field of virology, in particular the field of viral vaccine development.

2. Description of Related Art

Flaviviruses are a genus of blood borne pathogens that pose a significant threat to human. Flaviviruses include a variety of human pathogens such as West Nile (WNV), yellow fever (YF) and dengue (DEN) viruses. The flavivirus genome is a single-stranded, positive-sense RNA molecule approximately 11 kb in length encoding a single polyprotein that is co- and post-translationally cleaved by a combination of viral and host proteases to produce three structural and seven non-structural (NS) proteins (NS1, NS2A, NS2B, NS3, NS4A, NS4B and NS5).

In the United States West Nile virus has recently become a major human heath concern. West Nile virus is a member of the Japanese encephalitis (JE) serogroup, which also comprises Murray Valley encephalitis (MVE) and JE viruses, and was first isolated in the West Nile region of Uganda in 1937 (Smithburn 1940). Until recently WNV was found only in Africa, Asia, and Europe but emerged in the New World in 1999 when it was identified in New York. Since its introduction into northeastern U.S., WNV has spread throughout North America and has been responsible for over 16,000 human cases and 550 deaths (MMWR). There are a range of disease manifestations caused by WNV from inapparent infection to encephalitis and death due to the potential neuroinvasive and neurovirulence phenotypes of the virus.

Like other flaviviruses the WNV genome consists of a single open reading frame which encodes three structural genes including the capsid (C), membrane (prM/M), and envelope (E), 7 nonstructural genes (NS1, NS2A, NS2B, NS3, NS4A, NS4B, and NS5) and is flanked by 5' and 3' noncoding regions. Flaviviruses are unusual RNA viruses in that the NS1 protein is glycosylated in addition to the E protein (Muylaert 1990). The NS1 protein may have either two or three highly conserved glycosylation sites. All members of the JE serogroup, with the exception of JE virus, contain three glycosylation sites in the NS1 protein at positions $NS1_{130}$, $NS1_{175}$, and $NS1_{207}$ (Chambers 1990; Blitvich 2001, Sumiyoshi 1987). Other mosquito-borne flaviviruses, including JE and DEN viruses, contain two glycosylation sites in the NS1 protein at positions $NS1_{130}$ and $NS1_{207}$, while YF virus includes two sites at positions $NS1_{130}$ and $NS1_{208}$. Although the functions of the NS1 protein have not been completely elucidated, previous studies have shown that NS1 is involved in replication as shown by the colocalization of this protein and other NS proteins to double stranded RNA replicative forms (Mackenzie 1996; Westaway 1997), maturation of the virus (Mackenzie 1996) and RNA synthesis (Lindenbach and Rice 1997). Recently it has been noted that the NS1 protein may mimic extracellular matrix proteins and function to induce autoreactive antibodies (Falconar 1997, Chang 2002).

The NS1 protein exists as a hexamer, heat-labile homodimer or short-lived monomer and can be found inside the cell, associated with membranes or in secreted forms outside of the cell (Flamand 1999, Crooks 1994, Blitvich 2001, Schlesinger 1990, Mason 1989, Winkler 1988, 1989). Many forms of this protein have been shown to exist either due to alternative cleavage sites, formation of heterodimers, or differences in glycosylation (Blitvich 1995, 1999, Falgout 1995, Nestorowicz 1994, Mason 1989, Young and Falconar 1989). Previous studies with other flaviviruses containing non-glycosylated forms of the NS1 protein have concluded that glycosylation is not necessary for the dimerization of this protein although the stability of the dimer is reduced (Pryor and Wright 1993, 1994). It has also been noted that dimerization may not be necessary for the secretion of this protein or replication of the virus (Hall 1996).

NS1 is inserted into the endoplasmic reticulum by a hydrophobic signal sequence where it forms a dimer and high mannose glycans are added. The glycosylated protein then proceeds to the Golgi where complex glycans may be added before secretion from the cell (Pryor and Wright 1994, Depres 1991, Flammond 1992, Jacobs 1992, Mason 1989, Post 1991). It has been demonstrated for both DEN and YF viruses that the first glycosylation site ($NS1_{130}$) is a complex type while the second ($NS1_{207}$-[DEN]/$NS1_{208}$ [YF]) is a simple high mannose type (Muylaert 1996, Pryor 1994); however, this mixture is only seen in mammalian cells and not mosquito cells (Blitvich 1999). The lack of complex sugars at the second glycosylation site is hypothesized to be due to this site being buried within the dimer where it cannot be reached for this addition (Hall 1999). Murray Valley encephalitis virus also contains a mixture of complex and high mannose type sugars, the first site ($NS1_{130}$) is known to be complex type, while the third ($NS1_{207}$) is high mannose.(Blitvich 2001). The second glycosylation site ($NS1_{175}$) was not determined in this study.

Studies involving the ablation of the glycosylation sites of the NS1 protein have been performed for other flaviviruses, including DEN and YF viruses (Pryor 1994, 1998, Muylaert 1996, Pletnev 1993, Crabtree 2005). In contrast to WNV, these viruses contain only two glycosylation sites in their NS1 protein; the $NS1_{175}$ site being absent. Previously, deglycosylation of the NS1 protein of a tick-borne encephalitis virus (TBEV) prM and E genes-containing DEN-4 virus chimera, the $NS1_{130}$ mutant showed a decrease in neurovirulence while the mutation of the second glycosylation site ($NS1_{207}$) increased the neuroinvirulence in mice (Pletnev 1993). Similarly, a study of the deglycosylation of YF virus showed that the $NS1_{130}$ and the combined $NS1_{130/208}$ glycosylation mutants were attenuated for neurovirulence while the deglycosylated $NS1_{208}$ mutant alone was not (Muylaert 1996). This study also found that replacement the asparagine of the glycosylation motif with either alanine or serine showed similar results in in vitro studies, namely the lack of the first glycosylation site correlated with a reduction in the rate of RNA synthesis and a delay in the production of infectious virus. Comparable to these data, deglycosylated NS1 of a TBEV/DEN-4 chimera also showed a reduction in infectivity in monkey kidney LLC-MK2 and mosquito C6/36 cell types with the $NS1_{130}$ mutant showing greater reduction than the $NS1_{207}$ mutant (Pletnev 1993). Examination of the affects of the deglycosylation of the NS1 protein of DEN-2 virus New Guinea C strain showed that the $NS1_{130}$ and $NS1_{130/207}$ mutants had no detectable infectivity titer while the $NS1_{207}$ mutant had a 100-fold reduction in infectivity titer (Pryor 1998). The NS1$_{207}$ mutant virus was subsequently examined for mouse neurovirulence at an inoculum of 10 pfu and none of the mice inoculated with the NS1$_{207}$ mutant virus died while the parental virus caused 75% mortality at this dose. Recently a study involving the deglycosylation of dengue 2 virus strain 16681 showed a decrease in replication of the mutant viruses in C6/36 cells, but not mammalian cells, reduced NS1 secretion from infected cells and attenuation of neurovirulence in mice (Crabtree 2005). This study indicated that the ablation of the NS1$_{207}$ glycosylation site showed a greater difference than ablation of NS1$_{130}$ compared to the parental strain.

Another nonstructural protein that may be of interest with regard to flavivirus virulence is the small hydrophobic NS4B protein. The NS4B of West Nile virus (WNV) is cleaved by a combination of viral and host proteases (Chambers et al., 1989; Preugschat et al., 1991) and is believed to associate with other components of the viral replication complex in addition to contributing to evasion of host immune defenses. Within the family Flaviviridae, WNV NS4B exhibits ~35% identity with other mosquito-borne flaviviruses including yellow fever (YF) virus and members of the dengue (DEN) serogroup. Hepatitis C virus (HCV) NS4B displays negligible amino acid similarity with the WNV protein, however predicted topologies are similar suggesting a common function. Lundin et al., (2003) expressed recombinant HCV NS4B-GFP fusion protein in Hep3B cells and found that it was primarily localized to the endoplasmic reticulum and distributed in a reticular web-like pattern with scattered dense spots thought to represent foci of replication. Accumulation of Kunjin virus NS4B in the perinuclear region has also been described along with induction of membrane proliferation, and there is evidence that NS4B can translocate into the nucleus (Westaway et al., 1997). Recently DEN2 virus NS4B was found to inhibit the interferon-signaling cascade at the level of nuclear STAT phosphorylation (Munoz-Jordan et al., 2004).

A number of publications have described mutations in the NS4B protein in attenuated or passage-adapted mosquito-borne flaviviruses suggesting this protein plays a vital role in replication and/or pathogenesis. It is likely that NS4B interacts with a combination of viral and host factors to allow efficient replication in both vertebrates and mosquitoes. A single coding mutation (P101L) in DEN-4 virus NS4B conferred a small-plaque phenotype in C6/3 6 cells while at the same time increasing plaque size in Vero cells two-fold and Huh7 cells three-fold (Hanley et al., 2003). Pletnev et al. (2002) described DEN4 NS4B T105I and L112S substitutions that occurred in a chimeric virus expressing WNV structural proteins in a DEN-4 virus backbone. Blaney et al. (2003) noted a NS4B L112 F mutation in DEN4 virus passaged in Vero cells. The live attenuated Japanese encephalitis virus (JEV) vaccine strain SA14-14-2 has an I106V substitution in NS4B (Ni et al., 1995). A viscerotropic Asibi strain of YF virus generated by passaging seven times through hamsters accumulated seven amino acid substitutions including a V98I substitution in NS4B (McArthur et al., 2003). Interestingly YF vaccine strains also display an I95M mutation in NS4B (Hahn et al., 1987; Wang et al., 1995).

While both NS1 and NS4B may play a role in virulence of flavivirus it was previously unclear in the art what changes in these proteins would effectively attenuate flaviviruses. Thus, the present invention answers a long standing need in the art by providing mutant flaviviruses that are high attenuated and identifying mutations in viral nonstructural proteins that can mediate such attenuation.

SUMMARY OF THE INVENTION

In one embodiment of the invention, there is provided a nucleic acid molecule comprising sequence capable of encoding a mutant flaviviral NS4B protein of either the Japanese encephalitis or dengue sero- and genetic groups. This mutant NS4B protein has a central region, and comprises an amino acid deletion or substitution at a cysteine residue in the central region wherein, mutant flaviviruses encoding the mutant NS4B have reduced virulence as compared to wild type viruses. The term NS4B central domain as used here means the highly conserved stretch of amino acids shown in FIG. 1B. For example, the central region of Usutu virus extents from amino acid 100 (L) to amino acid 117(A) while the central region of WNV extents from amino acid 97 (L) to amino acid 114(A). The term nucleic acid sequence as used herein comprises both RNA and DNA sequences, consistent with its usage in the art. The Japanese encephalitis serogroup comprises Japanese encephalitis virus (JE), Kunjin virus (KUN), Murray Valley encephalitis virus (MVE), Saint Louis encephalitis virus (SLE), Usutu virus (USU) and West Nile virus while the dengue virus serogroup comprises Dengue virus, including dengue virus type 1, 2, 3 and 4 (see Lindenbach and Rice, 2001). Thus, the mutant NS4B sequences comprising a mutated central region from each of these viruses is included as part of the current invention.

In some specific embodiments, a mutant flaviviral NS4B according to the invention may comprise an amino acid substitution or deletion at a cysteine residue in the central region. It will be understood that a cysteine residue in an NS4B central region may be substituted for any other amino acid, since cysteine residues are the only amino acids with the unique ability to form disulfide bonds. In some further examples, a mutant flaviviral NS4B protein of the invention may include but is not limited to polypeptides comprising an amino acid substitution or deletion at cysteine 99 of DEN1 NS4B, cysteine 98 of DEN2 or DEN3 NS4B, cysteine 95 of DEN4 NS4B, cysteine 102 of JEV, Kunjin or WNV NS4B or cysteine 105 of MVEV, SLE or Usutu NS4B. In some specific embodiments, the amino acid substitution may be a cysteine to serine substitution. Therefore, in certain embodiments, the mutant NS4B protein may be a WNV NS4B protein comprising a deletion or an amino acid substitution at cysteine 102 (see FIG. 1B). In a specific example, the mutant WNV NS4B protein (SEQ ID NO:16) may comprise a cysteine to serine substitution at amino acid 102.

In additional embodiments, the invention provides a mutant flaviviral NS4B polypeptide comprising an amino acid deletion or substitution at the amino acid position corresponding to proline 38 of the WNV382-99 NS4B protein or a nucleic acid capable of encoding the same. As here the phrase "corresponding amino acid position" referred to amino acids that occupy the same position in two homologous polypeptide sequences when the two sequences are aligned with one another based upon amino acid identity or similarity. Some examples of amino acid positions corresponding to proline 38 of WNV382-99 are shown in FIG. 1A. Thus, a mutant flavivirus NS4B polypeptide of the invention may include but is not limited to an amino acid substitution or deletion at proline 37 in Langat (LGT), tick-borne encephalitis (TBE), Powassan or Omsk hemorrhagic fever (OHF) NS4B, proline 36 in YFV NS4B, proline 35 in DEN1 NS4B, proline 34 in DEN2 or DEN3 NS4B, proline 31 in DEN1 NS4B, proline 38 in WNV, JEV or Kunjin NS4B or proline 41 in SLE, MVEV or Usutu NS4B. It will be understood that any amino acid may be substituted for an NS4B proline residue of the invention. For instance in some specific embodiments, proline is substituted for glycine. Thus, in certain specific cases the invention provides a mutant WNV comprising a proline to glycine substitution at amino acid 38 of NS4B.

Furthermore, in certain aspects of the invention a mutant flavivirus NS4B polypeptide of the invention may also comprise a deletion or substitution at an amino acid position corresponding to $T_{116}$ of the WNV382-99 see FIG. 1B. For example, a mutant flavivirus NS4B may comprise a substitution or deletion at amino acid position corresponding to proline 38 of the WNV382-99 NS4B and a substitution or deletion at an amino acid position corresponding to $T_{116}$ of the WNV382-99 NS4B. In certain specific cases, a mutant NS4B protein of the invention may be a mutant WNV NS4B that comprises an amino acid substitution at $P_{38}$ and $T_{116}$ (e.g., $P_{38}G/T_{116}I$).

Thus, in certain specific a mutant NS4B polypeptide may comprise an amino acid substitution or deletion at an amino acid position corresponding to proline 38 of WNV382-99 and at an amino acid position corresponding to cysteine 102 of WNV382-99. Thus, in certain aspects the mutant NS4B polypeptide may be a WNV NS4B comprising an amino acid substitution or deletion at proline 38 and at cysteine 102. Furthermore, a mutant WNV NS4B may additionally comprise an amino acid substitution or deletion at threonine 116. Thus, in certain very specific cases, a mutant NS4B of the invention may be WNV NS4B $C_{102}S/P_{38}G$ or $C_{102}S/P_{38G}/T_{116}I$.

In some embodiments, the invention provides a nucleic acid molecule comprising a sequence encoding a mutant West Nile virus NS1 protein wherein the NS1 protein comprises an amino acid deletion or substitution that abrogates glycosylation of said NS1 protein and reduces the virulence of a virus encoding said NS1 protein. Thus, in certain embodiments, a mutant WNV NS1 comprises a single amino acid substitution or deletion in each of the glycosylation consensus sites of the WNV NS1 protein. For example, a mutant WNV NS1 can comprise a single amino acid substitution in each of the glycosylation consensus sites that control glycosylation at amino acids 130 (amino acid 921 in SEQ ID NO: 1), 175 (amino acid 966 in SEQ ID NO: 1) and 207 (amino acid 998 in SEQ ID NO: 1). As used herein the term glycosylation consensus site means the Asn-Xaa-Ser/Thr glycosylation acceptor sequence, wherein Asn is glycosylated and Xaa is any amino acid except proline. Thus, it will be understood that any amino acid deletion, substitution or insertion that disrupts the glycosylation consensus sequence of an NS1 protein is included as part of the invention. In a very specific example, a mutant WNV NS1 protein may comprise an amino acid substitution at amino acid 130, 175 and 207 of the WNV NS1 protein. For instance, a mutant WNV NS1 protein may comprise an asparagine to alanine substitution at amino acids 130, 175 and 207 of the WNV NS1 protein.

In further embodiments of the current invention, nucleic acid sequences described above also comprise additional sequences, such as additional viral sequences. For example, in some cases, the additional viral sequence is additional flaviviral sequence. In certain cases, these sequence are from the same virus as the origin of the mutant NS4B sequence however, in other cases, they may originate from other flaviviruses. In some embodiments, these sequences may comprise a complete viral genome. Therefore, in certain cases, the sequences may comprise an infectious flavivirus clone. In some aspects, the complete viral genome may be defined as a chimeric viral genome. As used herein the term "chimeric viral genome" refers to a viral genome comprising viral genes of gene fragments from two or more different flaviviruses. As used herein the term infectious clone means any nucleic acid sequence capable of producing replicating virus upon expression of the nucleic acid in a susceptible cell type. In a further embodiment, nucleic acid sequences according to the invention are comprised in a virus. It will be understood by one of skill in the art that such a virus may be chimeric virus comprising sequences derived from two or more viruses.

In some embodiments, additional flavivirus sequences comprise mutant flaviviral NS1 protein sequences wherein viruses encoding the mutant NS1 protein have reduced neurovirulence and neuroinvasiveness as compared to wild type viruses. For example, a nucleic acid sequence according to the invention may additionally comprise a mutant flaviviral NS1 protein wherein, said NS1 protein comprises a deletion or an amino acid substitution at a residue that is N-glycosylated. In some specific embodiments, the mutant flavivirus NS1 protein may comprise a deletion or amino acid substitution at all N-glycosylated residues of the NS1 protein. It will be understood by one of skill in the art that an amino acid substitution at an N-glycosylated residue in a flavivirus NS1 protein may be a substitution of any amino acid for the asparagine. However, in some specific embodiments, an amino acid substitutions in a flaviviral NS1 protein is an asparagine to alanine substitution. In certain cases, the mutant flaviviral NS1 protein is a mutant WNV NS1 protein comprising an amino acid substitution at position 130, 175 or 207 of the WNV NS1 protein. In specific examples, the mutant WNV NS1 protein comprises an amino acid substitution at amino acid 130, 175 and 207 of the WNV NS1 protein. Thus, in yet more specific examples, a mutant WNV NS1 protein comprises an asparagine to alanine substitution at amino acids 130, 175 and 207 of the WNV NS1 protein.

Additional flaviviral sequences of the invention may comprise mutant flaviviral E protein sequences wherein viruses encoding the mutant E proteins have reduced virulence as compared to wild type viruses. For example, a nucleic acid sequence according to the invention may additionally comprise a mutant flaviviral E protein wherein the E protein comprises a deletion or amino acid substitution at a residue that is N-glycosylated or a mutation that disrupts the glycosylation consensus sequence in a E protein. In some specific embodiments, the mutant flavivirus E protein may comprise a deletion or amino acid substitution at all N-glycosylated residues of the E protein. It will be understood by one of skill in the art that an amino acid substitution at an N-glycosylated residue in an E protein may substitute any amino acid for the asparagine. However, in some specific embodiments, an amino acid substitution in a flavivirus E protein is an asparagine to serine substitution. For instance, the mutant flaviviral E protein may be a mutant WNV E protein comprising an amino acid substitution at position 154 (amino acid 444 of SEQ ID NO:1) of the WNV E protein. In yet further embodiments the mutant flaviviral E protein is WNV E protein comprising a asparagine to serine substitution at amino acid 154. For instance in some cases the invention provides a mutant flavivirus comprising a mutant WNV NS1 coding sequence wherein the encoded protein is not N-glycosylated (i.e., an encoded sequence mutated at amino acids 130, 175 and 207) and a mutant WNV E protein with a substitution at position 154.

Thus, in certain embodiments of the current invention, there is provided a mutant flavivirus comprising nucleic acid encoding mutant NS4B and/or NS1 protein as described above. In certain aspects of the invention, such a mutant flavivirus may be further defined as an attenuated flavivirus that has reduced virulence, neuroinvasivness and/or neurovirulance relative to a wild type virus. In a further embodiment there is provided an immunogenic composition comprising a mutant flavivirus, according to the invention, and pharmaceutically acceptable excipient. Thus, it will be understood that an immunogenic composition may comprise any of the mutant flaviviruses described herein. In some embodiments, the mutant flavivirus is replication competent. However, in other embodiments the viruses are inactivated. For example in some specific cases the viruses according to the invention may be inactivated by irradiation, or chemical treatment, such as formalin treatment. In further embodiments, Immunogenic compositions according the invention may further comprise additional elements such as an adjuvant, an immunomodulator and/or a preservative. In yet further specific embodiments, an immunogenic composition may comprise sequences from two or more viruses according to the current the invention. Furthermore, in certain aspects of the invention, the immunogenic composition may be defined as a vaccine composition.

In certain aspects, a mutant flavivirus of the invention is defined as an attenuated virus. For example in some cases the attenuated virus may have reduced virulence. In some aspects, for example an attenuated virus will be defined as neuroattenuated virus. Such viruses may have reduced neuroinvasiveness or neurovirulence as compared to a wild type virus. As used the term "neuroinvasiveness" refers to the ability of a virus to spread to neuronal tissues such as the brain. On the other hand the term "neurovirulence" refers to the ability of a virus to replicate in neuronal tissue such as the brain. Thus, the neuroinvasiveness of a virus may be assessed by administering a virus to an animal systemically and later assessing how much virus is detected in a neuronal tissue such as the brain. On the other hand neurovirulence is assessed by administering virus directly to a neuronal tissue (e.g., by intracranial inoculation) and later determining how much the virus replicates or the severity of clinical disease caused by the virus. Thus, in certain aspects of the invention attenuated viruses may be defined as 10, 100, 1,000, 10,000, 100,000, 1,000,000 or more less virulent, neurovirulent or neuroinvasive than a wild type virus.

In certain preferred embodiments, there is provided a mutant flavivirus comprising at least two mutations as described herein. The skilled artisan will readily understand that due to the high mutation rate of RNA viruses attenuated viruses often revert to wild type virulent viruses through mutation that occurs during replication. Thus, attenuated viruses optimally comprise multiple attenuating mutations. For instance, a preferred attenuated virus may comprise a first mutations selected from a mutant NS4B coding sequence wherein the encoded protein comprises a deletion or substitution at an amino acid position corresponding to $P_{38}$ of WNV NS4B or corresponding to $C_{102}$ of WNV NS4B. Furthermore, the attenuated virus may comprise at least a second mutation selected from a sequence encoding a flavivirus NS1 protein with reduced glycosylation, a flavivirus E protein with reduced glycosylation or a mutant NS4B coding sequence wherein the encoded protein comprises a deletion or substitution at an amino acid position corresponding to $P_{38}$ of WNV NS4B or corresponding to $C_{102}$ of WNV NS4B. Furthermore, in some aspects of the invention mutations that abrogate glycosylation of an NS1 or E protein will comprise multiple amino acid changes in the glycosylation consensus thereby reducing the probability that a virus can revert to a wild type during replication.

In still further embodiments of the invention of the invention there is provided a method of generating an immune response in an animal comprising administering to the animal an immunogenic composition of the invention. Thus, there is further provided a method of vaccinating an animal comprising obtaining a vaccine composition according the invention and administering the vaccine composition to an animal. For example, the vaccine composition may be administered to a human, however the method may also be used to vaccinate livestock, animals in zoological gardens, wild and domesticated birds, cats, and dogs. In certain cases, the vaccine composition may be administered, orally, intravenously, intramuscularly, intraperitoneally, or subcutaneously. Additionally, in some cases, a vaccine composition may be administered multiple times, and in certain cases each administration may be separated by a period of days, weeks, months or years.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claims, when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawing in combination with the detailed description of specific embodiments presented herein.

FIG. 1A-C: Complete NS4B amino acid alignments including both tick-borne and mosquito-borne flaviviruses show conservation of the WNV C102 residue within the DEN and JE genetic groups. This residue is not found in the tick-borne flaviviruses or yellow fever virus. In contrast, the WNV C120 and C237 residues are only found in WNV and Kunjin virus while C227 is found throughout the JE genetic group. Various mutations occurring in attenuated or passage-adapted virus strains localize between consensus residues 100 and 120. The NS4B central region is underlined in FIG. 1B. Abbreviations and sequence listings are as follows Langat virus (Langat) (SEQ ID NO: 3), TBE (Tick-borne encephalitis virus) (SEQ ID NO: 4), Powassan virus (Powassan) (SEQ ID NO: 5), Omsk hemorrhagic fever virus (OHF) (SEQ ID NO: 6), Yellow fever virus strain ASIBI (YFVasibi) (SEQ ID NO: 7), Yellow fever virus 17D-213), vaccine strain (YFV17D) (SEQ ID NO: 8), Dengue Virus serotype 1 (DEN1) (SEQ ID NO: 9), Dengue Virus serotype 2 (DEN2)

(SEQ ID NO: 10), Dengue Virus serotype 3 (DEN3) (SEQ ID NO: 11), Dengue Virus serotype 4 (DEN4) (SEQ ID NO: 12), Japanese encephalitis virus (JEV) (SEQ ID NO: 13), Murray Valley fever virus (MVEV) (SEQ ID NO: 14), Kunjin virus (Kunjin) (SEQ ID NO: 15), West Nile virus, strain New York 382-99 (WNV382-99) (SEQ ID NO: 16), Saint Louis encephalitis virus (SLE) (SEQ ID NO: 17) and Usutu virus (Usutu) (SEQ ID NO: 18). The consensus sequence is listed as SEQ ID NO: 19.

FIG. 2A-D: Multiplication kinetics of recombinant wild-type and cysteine mutant viruses in monkey kidney Vero, mouse Neuro2A, and mosquito C6/36 cells as indicated. Growth curves are conducted at a multiplicity of infection (m.o.i.) of 0.01, the limit of detection is <0.7 log 10PFU/mL. Growth kinetics are determined in Vero cells at 37° C. (FIG. 2A), Vero cells at 41° C. (FIG. 2B), Neuro2A cells at 37° C. (FIG. 2C) and C6/36 cells at 28° C. (FIG. 2D).

FIG. 3A-D: Viral RNA (FIG. 3A-B) and protein (FIG. 3C-D) levels from cellular lysates of wild-type and C102S mutant infected cell cultures incubated at 37° C. and 41° C. FIG. 3A-B, Taqman quantitative real-time RTPCR is conducted on total cellular RNA preparations using primers localizing to the WNV 3'-UTR. Data is converted to RNA genome equivalents (GEQ) utilizing a standardized curve and plotted along with viral titer as determined by plaque assay. FIG. 3C-D, are reproductions of Western blots for WNV E protein (upper panels) or β-actin (lower panels) in Vero cells infected with either wild type virus of $C_{102}S$ mutant virus at 37° C. (FIG. 3A) and 41° C. (FIG. 3B).

FIG. 4A-B: Western Blot analysis of the glycosylation mutants compared to parental strain. FIG. 4A, Three potential glycosylation sites in the NS1 protein. Lysates are prepared from Vero infected cells with either $NS1_{130}$, $NS1_{175}$ or $NS1_{207}$ and compared to the NY99 infected cell lysate. Differences in the molecular weight confirm all three sites are glycosylated in mammalian cells. FIG. 4B, NS1 protein from supernatant confirms all nonglycosylated mutants secrete NS1. Lane 1: NY99, Lane 2: $NS1_{130}$, Lane 3: $NS1_{175}$, Lane 4: $NS1_{207}$, Lane 5: $NS1_{130/175}$) Lane 6: $NS1_{130/207}$, Lane 7: $NS1_{175/207}$, Lane 8: $NS1_{130/175/207}$.

FIG. 5A-C: Growth curve analysis in Vero (FIG. 5A), P388 (FIG. 5B) and C6/36 (FIG. 5C) cells. All three growth curves are analyzed by plaque titration in Vero cells. Confluent monolayers are infected with an m.o.i. of 0.1 with either parental NY99, attenuated $NS1_{130/207}$ or $NS1_{130/175/207}$ mutant viruses.

FIG. 6A-B: Serum (FIG. 6A) and brain (FIG. 6B) viral titer six days post infection with the parental NY99 and two attenuated ($NS1_{130/207}$ and $NS1_{130/175/207}$) viruses. Mice are infected with $10^3$ pfu virus. Serum chart shows clearance of virus by 4 days post infection. Only mice infected with parental virus showed virus in the brain which is detectable beginning on day 4.

FIG. 7A-D: In vitro replication kinetics of various West Nile viruses. Assays are performed as previously described and in each case the Y-axis indicates $Log_{10}PFU/ml$ and the X-axis indicates hours post infection. Replication assays are examined in P388 cells (FIG. 7A, D), Nero2A cells (FIG. 7B) and Vero cells (FIG. 7C).

FIG. 8A-B: In vitro replication kinetics for the indicated West Nile viruses. Assays are performed as previously described and in each case the Y-axis indicates $Log_{10}$ PFU/ml and the X-axis indicates hours post infection. Replication assays are examined in Vero cells at 37° C. (FIG. 8A) and Vero cells at 41° C. (FIG. 7B).

DETAILED DESCRIPTION OF THE INVENTION

Figure 1A:
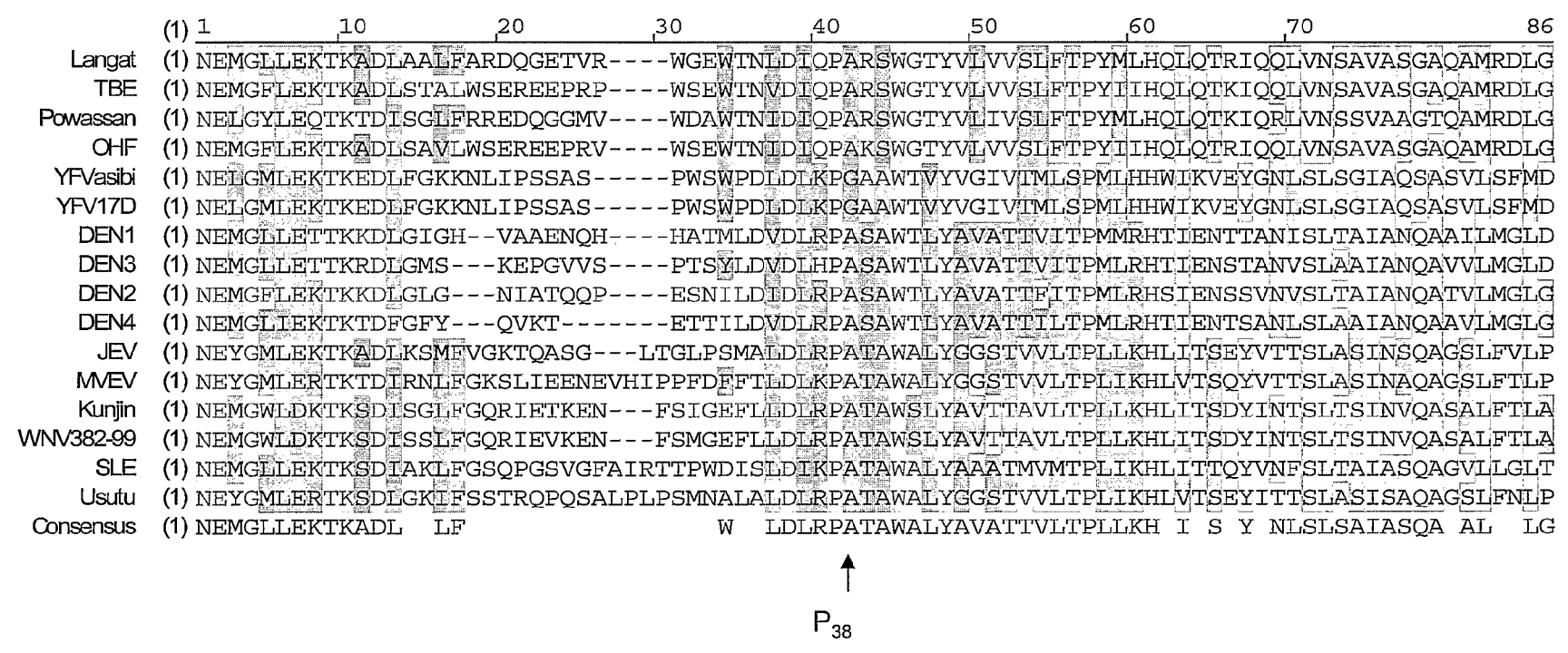

Studies herein demonstrate the role of the cysteine residues in the function of the flavivirus NS4B protein using WNV model system. Although there are four cysteine residues (102, 120, 227 and 237) only mutation of the 102 residue altered the phenotypic properties of NS4B. Specifically, mutation of residue 102 attenuate virulence in mice and induce a temperature sensitive phenotype. There is considerable evidence to suggest that the central region of NS4B plays a role in the virulence phenotype of flaviviruses. However, this is the first time a single engineered amino acid substitution in this region has been shown to directly confer an attenuated phenotype in an animal model. Examination of a hydrophobicity plot of NS4B generated by the SOSUI program suggests that NS4B C120 is in a transmembrane region, C227 and C237 are in the lumenal C-terminus, and C102 is predicted to reside near the junction of a lumenal ectodomain and a transmembrane region (not shown). Interestingly, this cysteine residue is conserved in all members of the Japanese encephalitis and dengue genetic groups (FIG. 1A-C) suggesting that the $C_{102}S$ mutation will attenuate all of these viruses in these families.

The attenuation phenotype of the $C_{102}S$ mutant were found 10,000-fold for both mouse neuroinvasiveness and neurovirulence. This high level of attenuation is exceeded only by chimeric constructs such as the WNV PrM-E/DEN4 chimera (Pletnev et al., 2002) or WNV PrM-E/YFV 17-D chimera (Monath et al., 2001), neither of which are encoded by the WNV replication machinery. Thus, neither of these chimeric viruses is able to elicit an immune response against WNV nonstructural proteins, a deficiency that may limit their use as vaccines. The fact that a single nucleotide change in WNV can lead to such a dramatic attenuated phenotype implies that the NS4B protein encodes a critical function in virulence that may not be readily identifiable in cell culture. The $C_{102}S$ mutant grew comparably to wild-type virus in Vero cells, Neuro2A cells, and C6/36 cells at permissive temperatures, however the mutant virus did displayed an altered phenotype in Vero cells at 41° C. This attribute is very important since viruses lacking NS4B C102 can be grown to high titer in tissue culture enabling the efficient manufacture of immunogenic compositions such as vaccines.

Additionally, it is demonstrated herein that WNV utilizes three glycosylation sites in the NS1 protein, each with either complex or high mannose sugars. Most significantly, mutation(s) of these sites attenuate the neuroinvasivness and neurovirulence phenotypes of WNV in mice. The ablation of glycosylation sites of the NS1 protein in various combinations still allows viral replication, although both cell culture and in vivo data suggest that replication is not as efficient as parental virus. It is apparent that there may be multiple factors leading to the suppression of replication of the NS1 mutants. The first evidence comes from the growth curve data. Replication of the most attenuated mutant showed a reduction in infectivity titer in the P388 cell line compared to the parental strain particularly at the 12 and 48 hour time points. This is consistent with previous studies that indicated a delay in the production of infectious YF virus (Muylaert 1996). This impediment may result in an earlier clearance of the virus from the blood resulting in the inability of this virus to replicate to high enough titers to invade the blood brain barrier. In vitro data also suggests that although NS1 is still secreted that the rate may be diminished or otherwise compromised. This would suggest that secreted NS1 functions contribute toward the virulence of this virus.

Perhaps most importantly, comparison of parental NY99 with the two $NS1_{130/207}$ and $NS1_{130/175/207}$ attenuated mutants showed that mice that succumbed to infection had a higher viremia on days 2 and 3 post-infection than mice that survived infection. Neuroinvasive disease correlated with a peak viremia of >600 pfu/mil in all mice examined in this study. Mice with viremia less than 600 pfu/ml survived infection, except for one mouse that showed a reversion at NS $1_{130}$. Furthermore, mice inoculated with the attenuated strains did not have detectable virus in the brain, suggesting that the attenuated strains do not produce sufficient virus to cross the blood-brain barrier and invade the brain.

The studies herein demonstrate the important role of the NS1 and NS4B non-structural proteins is in flaviviral virulence. In particular, it is shown that by abrogating glycosylation of the NS protein the virulence of WNV can be substantially reduced. Further studies demonstrate that NS4B mutations can also contribute to an flavivirus attention.

Vaccines based on these mutations either alone or in combination could offer significant advantages over other vaccine strategies. For example, in certain cases viruses comprising mutations of the invention may be used in live attenuated vaccine, such as a WNV vaccine.

Such vaccines may be advantageous in there ability to produce a robust immune response as compared to inactivated viral vaccines. Nonetheless, by incorporating multiple mutations in a live attenuated vaccine strain the chance of a revertent, virulent virus emerging is greatly decreased.

I. Additional Attenuating Flaviviral Mutations

In some embodiments the current invention concerns mutant West Nile virus (WNV) sequences, thus in some cases mutations can be made in WNV strains New York 382-99 (NY99) (GenBank accession no. AF196835) (SEQ ID NO:1) or TM171-03 (GenBank accession no. AF196835) SEQ ID NO:2.

In certain embodiments mutant viruses according to the current invention may additionally comprise other attenuating mutations. For example an amino acid substitution at amino acid 154 (numbering relative to the 382-99 strain) of the West Nile virus E protein. In some other embodiments, a WNV E protein may comprise additional mutations for example mutations in the E protein fusion loop (L107), the receptor binding domain III (A316), or a stem helix (K440) (Beasley et al., 2005).

II. Variation or Mutation of an Amino Acid Coding Region

The following is a discussion based upon changing of the amino acids of a protein. For example, certain amino acids may be substituted for other amino acids in a protein structure without appreciable loss of interactive binding capacity. In certain aspects of the invention substitution of unrelated amino acids may be preferred in order to completely abolish the activity of a particular viral polypeptide. However in other aspects amino acid may be substituted for closely related amino acids in order to maintain proper folding of a polypeptide sequence. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of as discussed below.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine*−0.5); cysteine (−1.0); methionine (−1.3); valine (−1.5); leucine (−1.8); isoleucine (−1.8); tyrosine (2.3); phenylalanine (−2.5); tryptophan (−3.4).

It is understood that an amino acid can be substituted for another having a similar hydrophilicity value and still produce, a biologically equivalent and immunologically equivalent protein. In such changes, the substitution of amino acids whose hydrophilicity values are within ±2 is preferred, those that are within ±1 are particularly preferred, and those within ±0.5 are even more particularly preferred. Thus, as used herein the term "percent homology" refers to a comparison between amino acid sequences, for example wherein amino acids with hydrophilicities within +/−1.0, or +/−0.5 points are considered homologous.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

However, it will also be understood that certain amino acids have specific properties, and thus any amino acid substitution will abolish said property. For example cysteine residues have the unique ability to form di-sulfide bonds, that can be crucial for protein structure and activity. Thus, a substitution of cysteine residue for any other amino acid may be expected, by one of skill in the art, to alter the activity of a protein. Likewise asparagine residues that glycosylated in cells have a very specific property, and thus substitution of any other amino acid for said asparagine residue will abolish these properties.

The term "functionally equivalent codon" is used herein to refer to codons that encode the same amino acid, such as the six codons for arginine and/or serine, and/or also refers to codons that encode biologically equivalent amino acids. Thus when an amino acid coding sequence is mutated, one, two, or three nucleotide changes may be introduce to alter the coding region of a nucleic acid sequence. Table 1, indicates the nucleic acid codons that single for incorporation of particular amino acid sequences. Thus one of skill in the art can use this information to alter and amino acid coding region, and thus alter the amino sequence of the protein encoded by that region. Additionally this information allows one of skill in the art to determine many nucleic acid sequences that can be used to code for a given amino acid sequence. In each case the post used codon for each amino acid, in mammals, is indicated in the left column of Table 1. For example, the most preferred codon for alanine is thus "GCC", and/or the least is "GCG" (see Table 1, below).

TABLE 1

Preferred Human DNA Codons

| Amino Acids | | | Codons |
|---|---|---|---|
| Alanine | Ala | A | GCC GCT GCA GCG |
| Cysteine | Cys | C | TGC TGT |
| Aspartic acid | Asp | D | GAC GAT |
| Glutamic acid | Glu | E | GAG GAA |
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG CTC TTG CTT CTA TTA |
| Methionine | Met | M | ATG |
| Asparagine | Asn | N | AAC AAT |
| Proline | Pro | P | CCC CCT CCA CCG |
| Glutamine | Gln | O | CAG CAA |
| Arginine | Arg | R | CGC AGG CGG AGA CGA CGT |
| Serine | Ser | S | AGC TCC TCT AGT TCA TCG |
| Threonine | Thr | T | ACC ACA ACT ACG |
| Valine | Val | V | GTG GTC GTT GTA |
| Tryptophan | Trp | W | TGG |
| Tyrosine | Tyr | Y | TAC TAT |

It will also be understood that amino acid and/or nucleic acid sequences may include additional residues, such as additional N and/or C terminal amino acids and/or 5' and/or 3' sequences, and/or yet still be essentially as set forth in one of the sequences disclosed herein. The addition of terminal sequences particularly applies to nucleic acid sequences that may, for example, include various non-coding sequences flanking either of the 5' and/or 3' portions of the coding region and/or may include various internal sequences, i.e., introns, which are known to occur within genes.

Excepting intronic and/or flanking regions, and/or allowing for the degeneracy of the genetic code, sequences that have between about 70% and/or about 79%; and/or more preferably, between about 80% and/or about 89%; and/or even more preferably, between about 90% and/or about 99%; of nucleotides that are identical to a given nucleic acid sequence.

III. Vaccine Component Purification

In any case, a vaccine component (e.g., an antigenic peptide, polypeptide, nucleic acid encoding a proteinaceous composition or virus particle) may be isolated and/or purified from the chemical synthesis reagents, cell or cellular components. In a method of producing the vaccine component, purification is accomplished by any appropriate technique that is described herein or well known to those of skill in the art (e.g., Sambrook et al., 1987). Although preferred for use in certain embodiments, there is no general requirement that an antigenic composition of the present invention or other vaccine component always be provided in their most purified state. Indeed, it is contemplated that less substantially purified vaccine component, which is nonetheless enriched in the desired compound, relative to the natural state, will have utility in certain embodiments, such as, for example, total recovery of protein product, or in maintaining the activity of an expressed protein. However, it is contemplate that inactive products also have utility in certain embodiments, such as, e.g., in determining antigenicity via antibody generation.

The present invention also provides purified, and in preferred embodiments, substantially purified vaccines or vaccine components. The term "purified vaccine component" as used herein, is intended to refer to at least one vaccine component (e.g., a proteinaceous composition, isolatable from cells), wherein the component is purified to any degree relative to its naturally obtainable state, e.g., relative to its purity within a cellular extract or reagents of chemical synthesis. In certain aspects wherein the vaccine component is a proteinaceous composition, a purified vaccine component also refers to a wild type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 1989; and Freifelder, Physical Biochemistry, Second Edition, pages 238 246, incorporated herein by reference).

Given many DNA and proteins are known (see for example, the National Center for Biotechnology Information's Genbank and GenPept databases (http://www.ncbi.nlm.nih.gov/)), or may be identified and amplified using the methods described herein, any purification method for recombinately expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al. 1989, incorporated herein by reference). In further aspects, a purification of a proteinaceous sequence may be conducted by recombinately expressing the sequence as a fusion protein. Such purification methods are routine in the art. This is exemplified by the generation of an specific protein glutathione S transferase fusion protein, expression in E. coli, and isolation to homogeneity using affinity chromatography on glutathione agarose or the generation of a polyhistidine tag on the N or C terminus of the protein, and subsequent purification using Ni affinity chromatography. In particular aspects, cells or other components of the vaccine may be purified by flow cytometry. Flow cytometry involves the separation of cells or other particles in a liquid sample, and is well known in the art (see, for example, U.S. Pat. Nos. 3,826,364, 4,284,412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified antigen or other vaccine component.

IV. Additional Vaccine Components

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s).

a. Immunomodulators

For example, it is contemplated that immunomodulators can be included in the vaccine to augment a cell's or a patient's (e.g., an animal's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

i. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations thereof.

ii. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

iii. Immunogenic Carrier Proteins

In certain embodiments, an antigenic composition may be chemically coupled to a carrier or recombinantly expressed with a immunogenic carrier peptide or polypeptide (e.g., a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m maleimidobenzoyl N hydroxysuccinimide ester, carbodiimide and bis biazotized benzidine.

iv. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low dose cyclophosphamide (CYP; 300 mg/m2) (Johnson/Mead, NJ), or a gene encoding a protein involved in one or more immune helper functions, such as B 7.

b. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° C. to about 101° C. for a 30 second to 2 minute period, respectively. Aggregation by reactivating with pepsin treated (Fab) antibodies to albumin, mixture with bacterial cell(s) such as C. parvum, an endotoxin or a lipopolysaccharide component of Gram negative bacteria, emulsion in physiologically acceptable oil vehicles, such as mannide mono oleate (Aracel A), or emulsion with a 20% solution of a perfluorocarbon (Fluosol DA®) used as a block substitute, also may be employed.

Some adjuvants, for example, certain organic molecules obtained from bacteria, act on the host rather than on the antigen. An example is muramyl dipeptide (N acetylmuramyl L alanyl D isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611).

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N acetylmuramyl L alanyl D isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (bacillus Calmette-Guerin, an attenuated strain of *Mycobacterium*) and BCG cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579, 945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE® BCG (Organon Inc., West Orange, N.J.).

In a typical practice of the present invention, cells of *Mycobacterium bovis*-BCG are grown and harvested by methods known in the art. For example, they may be grown as a surface pellicle on a Sauton medium or in a fermentation vessel containing the dispersed culture in a Dubos medium (Rosenthal, 1937). All the cultures are harvested after 14 days incubation at about 37° C. Cells grown as a pellicle are harvested by using a platinum loop whereas those from the fermenter are harvested by centrifugation or tangential-flow filtration. The harvested cells are resuspended in an aqueous sterile buffer medium. A typical suspension contains from about $2\times10^{10}$ cells/ml to about $2\times10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non irradiated tumor cells, is irrelevant in such circumstances.

One group of adjuvants preferred for use in some embodiments of the present invention are those that can be encoded by a nucleic acid (e.g., DNA or RNA). It is contemplated that such adjuvants may be encoded in a nucleic acid (e.g., an expression vector) encoding the antigen, or in a separate vector or other construct. These nucleic acids encoding the adjuvants can be delivered directly, such as for example with lipids or liposomes.

c. Excipients, Salts and Auxillary Substances

An antigenic composition of the present invention may be mixed with one or more additional components (e.g., excipients, salts, etc.) which are pharmaceutically acceptable and compatible with at least one active ingredient (e.g., antigen). Suitable excipients are, for example, water, saline, dextrose, glycerol, ethanol and combinations thereof.

An antigenic composition of the present invention may be formulated into the vaccine as a neutral or salt form. A pharmaceutically acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2 ethylamino ethanol, histidine, procaine, and combinations thereof.

In addition, if desired, an antigenic composition may comprise minor amounts of one or more auxiliary substances such as for example wetting or emulsifying agents, pH buffering agents, etc. which enhance the effectiveness of the antigenic composition or vaccine.

V. Vaccine Preparations

Once produced, synthesized and/or purified, an antigen, virus or other vaccine component may be prepared as a vaccine for administration to a patient. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an antigenic composition comprising flaviviral protein or nucleic acid sequence as active ingredient(s), in light of the present disclosure. In preferred embodiments, the compositions of the present invention are prepared to be pharmacologically acceptable vaccines.

Pharmaceutical vaccine compositions of the present invention comprise an effective amount of one or more flaviviral antigens or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one flaviviral antigen or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The anti-flaviviral vaccine may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The Flaviviral vaccine, according to the invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the flaviviral vaccine is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VI. Vaccine Administration

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., innoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1 5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the flavivirus can be performed, following immunization.

VII. Enhancement of an Immune Response

The present invention includes a method of enhancing the immune response in a subject comprising the steps of contacting one or more lymphocytes with a flavivirus antigenic composition, wherein the antigen comprises as part of its sequence a sequence nucleic acid or aminoacid sequence encoding mutant NS4B or NS1 protein, according to the invention, or a immunologically functional equivalent thereof. In certain embodiments the one or more lymphocytes is comprised in an animal, such as a human. In other embodiments, the lymphocyte(s) may be isolated from an animal or from a tissue (e.g., blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained with from an animal (e.g., a patient), then pulsed with composition comprising an antigenic composition. In a preferred embodiment, the lymphocyte(s) may be administered to the same or different animal (e.g., same or different donors).

a. Cytotoxic T Lymphocytes

In certain embodiments, T-lymphocytes are specifically activated by contact with an antigenic composition of the present invention. In certain embodiments, T-lymphocytes are activated by contact with an antigen presenting cell that is or has been in contact with an antigenic composition of the invention.

T cells express a unique antigen binding receptor on their membrane (T cell receptor), which can only recognize antigen in association with major histocoinpatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cells that recognizes an antigen MHC complex proliferates and differentiates into an effector cell called a cytotoxic T lymphocyte (CTL). CTLs eliminate cells of the body displaying antigen by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemagglutinin stimulated IL 2 expanded cell line established from PBMC (Bernard et al., 1998) or by T cells isolated from a previously immunized subject and restimulated for 6 days with DC infected with an adenovirus vector containing antigen using standard 4 h 51Cr release microtoxicity assays. In another fluorometric assay developed for detecting cell mediated cytotoxicity, the fluorophore used is the non toxic molecule alamarBlue (Nociari et al., 1998). The alamarBlue is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard 51Cr release assay.

In certain aspects, T helper cell responses can be measured by in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

b. Antigen Presenting Cells

In general, the term "antigen presenting cell" can be any cell that accomplishes the goal of the invention by aiding the enhancement of an immune response (i.e., from the T-cell or -B-cell arms of the immune system) against an antigen (e.g., a flaviviral sequence according to the invention or a immunologically functional equivalent) or antigenic composition of the present invention. Such cells can be defined by those of skill in the art, using methods disclosed herein and in the art. As is understood by one of ordinary skill in the art, and used herein certain embodiments, a cell that displays or presents an antigen normally or preferentially with a class II major histocompatability molecule or complex to an immune cell is an "antigen presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, pp. 65 66, 71-74 1986; Campbell, pp. 75 83, 1984; Kohler and Milstein, 1975; Kohler and Milstein, 1976, Gefter et al., 1977, each incorporated herein by reference. In some cases, the immune cell to which an antigen presenting cell displays or presents an antigen to is a $CD4^+TH$ cell. Additional molecules expressed on the APC or other immune cells may aid or improve the enhancement of an immune response. Secreted or soluble molecules, such as for example, immunomodulators and adjuvants, may also aid or enhance the immune response against an antigen. Such molecules are well known to one of skill in the art, and various examples are described herein.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Rescue of Mutant Viruses

Figure 1B:
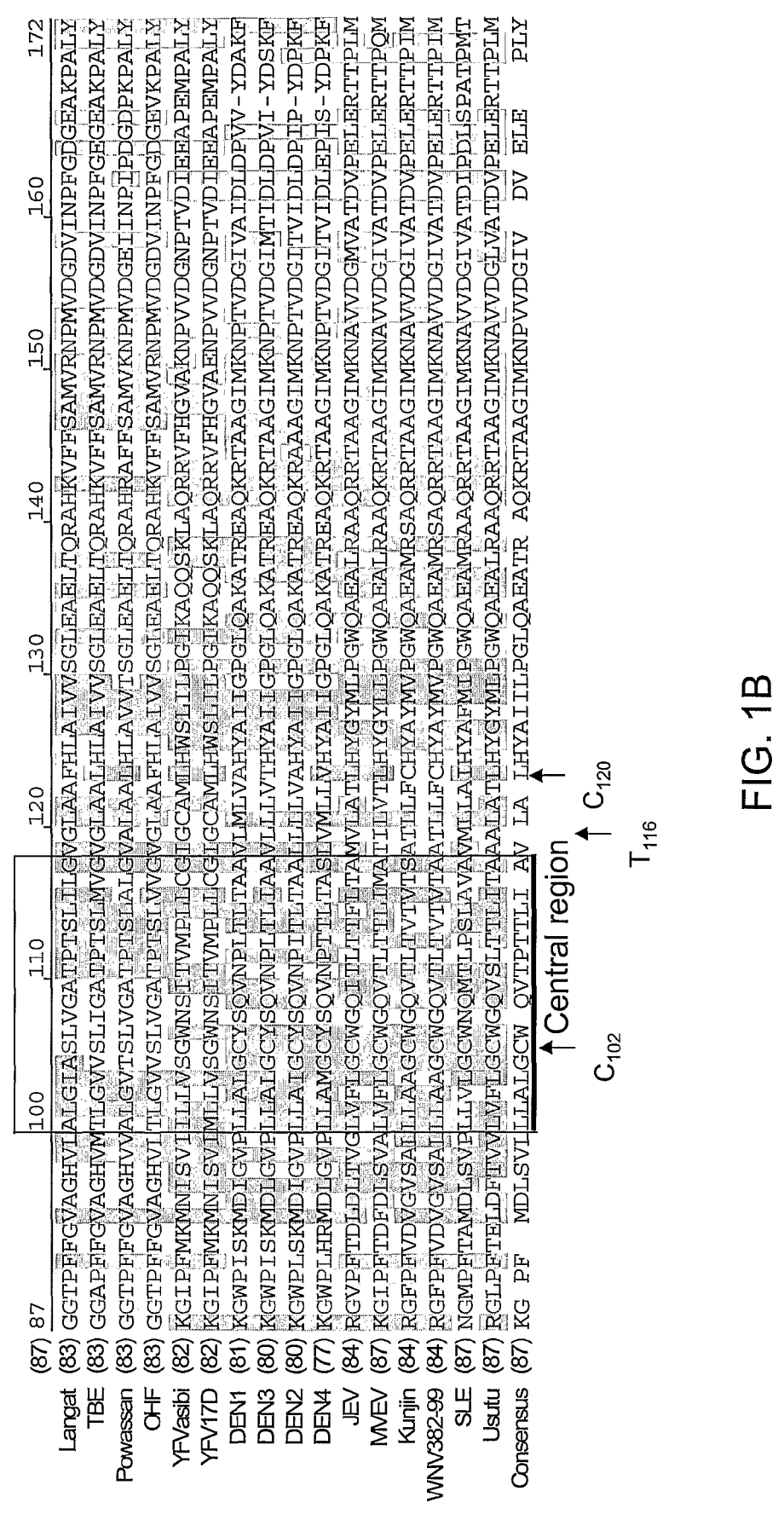
Figure 1C:
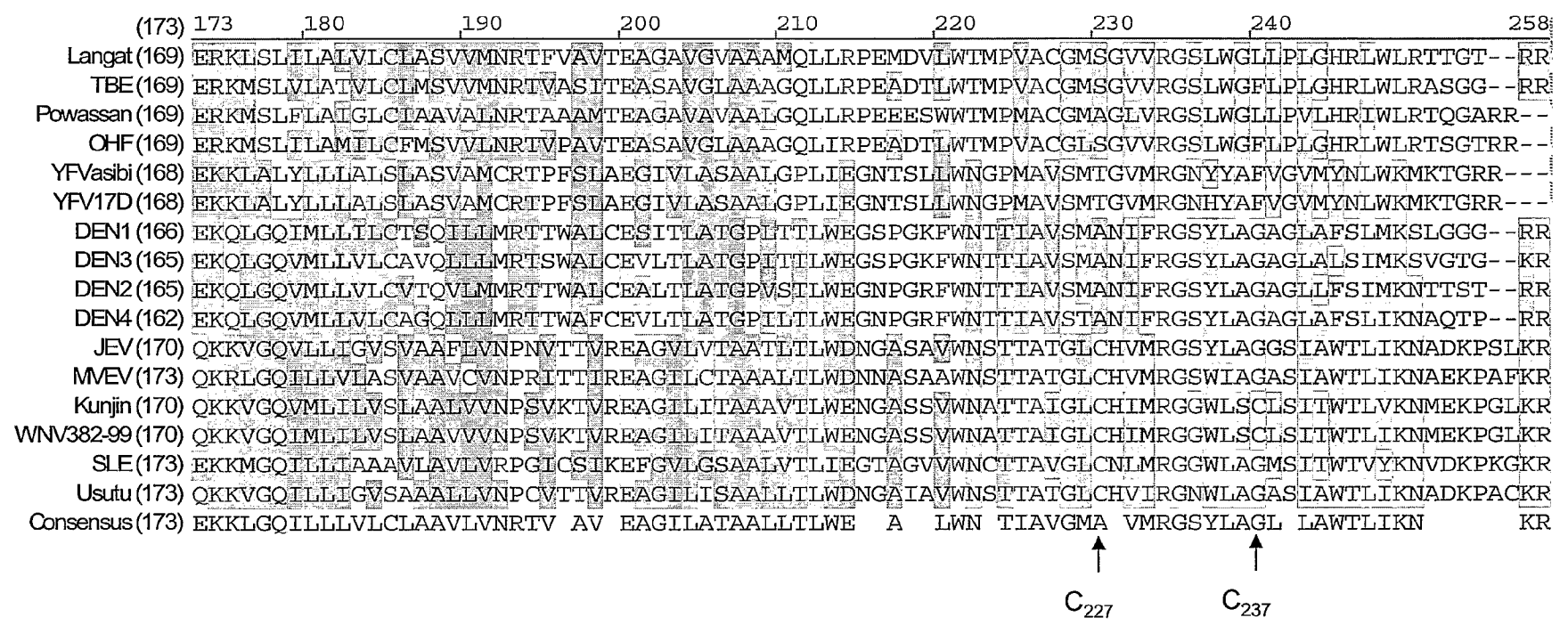

The flavivirus NS4B protein secondary structure predictions suggest that it is a very hydrophobic protein with four transmembrane regions (see FIG. 1A-C). The protein has four cysteine residues at positions 102, 120, 227 and 237. Examination of amino acid alignments of flaviviral NS4B proteins reveals that C102 and C120 localize to a central region. While $C_{102}$ is conserved throughout all members of the dengue and JE serogroups, $C_{120}$ is unique to WNV and Kunjin viruses. Both $C_{227}$ and $C_{237}$ are located in the C-terminal region of the protein that is thought to reside in the ER-lumen. The $C_{227}$ residue is conserved within the JE serogroup while $C_{237}$ is again unique to WNV and Kunjin viruses. Since cysteines are often critical for proper protein function, the role of the four cysteine residues in the NS4B protein is investigated by mutating each of them to a serine using reverse genetics.

The 3' plasmid of the WNV infectious clone WN/IC P991 serves as the template for introduction of mutations (Beasley et al., 2005). Mutagenesis is conducted using the Quick-Change XL Site-Directed Mutagenesis Kit (Stratagene) following the protocol accompanying the kit. Sets of primers are designed for each engineered mutation ($C_{102}S$, $C_{120}S$, $C_{227}S$, $C_{237}S$) including sufficiently long flanking regions to obtain a predicted melting temperature of at least 78° C. Mutagenesis reactions are carried out in a thermocycler following specific cycling parameters listed in the protocol. Products are then digested with Dpn I to remove parental DNA and transformed into XL-10 Gold ultracompetent cells that are subsequently plated on LB/ampicillin plates. Four colonies from each mutagenesis reaction are picked and miniprepped, and DNA sequencing is conducted to confirm the presence of the desired mutation and absence of additional mutations in the NS4B gene. Appropriate plasmids are grown in 200 mL cultures to obtain concentrated DNA for farther manipulation.

The WNV NY-99 infectious clone is constructed in two plasmids as described by Beasley et al. (2005). 3 µg each of 5' pWN-AB and 3' pWN-CG infectious clone plasmids are digested simultaneously with NgoMIV and XbaI restriction enzymes. Appropriate DNA fragments are visualized on an agarose gel and purified using a gel extraction kit (Qiagen). Fragments are ligated overnight on the benchtop using T4 DNA ligase. DNA is linearized by digesting with XbaI, treated with Proteinase K, and is extracted twice with phenol/chloroform/isoamyl alcohol and once with chloroform. DNA is ethanol precipitated, and the pellet is resuspended in TE buffer. The resulting product served as the template for transcription using a T7 ampliscribe kit and A-cap analog. Following a 3 hour incubation at 37° C., the transcription reaction is added to $1.5 \times 10^7$ Vero cells suspended in 500 uL PBS, and transfection is accomplished using electroporation. Cells are placed in a 0.2 cm electrode gap cuvette on ice and pulsed twice at 1.5 kV, infinite Ohms, and 25 uF. Tubes are allowed to incubate at room temperature for ten minutes before being transferred to T75 flasks containing MEM with 8% FBS, grown at 37° C. and 5% $CO_2$, and viruses are ready to harvest by day 5 or 6 post-transfection. Supernatant containing virus is spun down 5 minutes at 12,000 rpm and 1 mL aliquots were stored at −80° C. 140 uL of supernatant was added to an aliquot of AVL buffer, and viral RNA was isolated using the Viral RNA Mini-Spin kit (Qiagen).

The presence of the desired mutation is confirmed by amplifying the NS4B region using the Titan One-Step RT-PCR kit with subsequent DNA sequencing. Full-length genomic sequencing of the recombinant viruses reveals the presence of the mutation of interest and the absence of any additional mutations. The original virus yield from the transfection is used in all subsequent studies with no further passaging. All recombinant viruses generated infectivity titers in excess of 5 log 10 pfu/mL by five days post-transfection.

Example 2

Replication Kinetics of Mutant Viruses

Each recombinant mutant virus is investigated for temperature sensitivity by plaquing in Vero cells at both 37° C. and 41° C. Titers of recombinant viruses are determined by plaquing in Vero cells at both 37° C. and 41° C. Vero cells are allowed to grow to approximately 90% confluency in six-well plates. Media is removed, and cells are rinsed with PBS. Virus stocks are serially diluted, and 200 µL dilution is added to each well. Virus is allowed to incubate for 30 minutes before overlaying with a 50:50 mixture of 4% BGS 2xMEM and 2% agar. Two days after the first overlay, 2 mL of a mixture of 2% agar and 4% BGS 2xMEM supplemented with 2% neutral red was added to each well. Plaques are visualized and counted the following day and viral titers are calculated. Viruses found to be attenuated at 41° C. are plaqued at 39.5° C. to determine if this was a permissive temperature. Wild-type, and the $C_{120}S$, $C_{227}S$, and $C_{237}S$ mutant viruses all showed a comparable level efficiency of plaquing at both temperatures (Table 2). In comparison, the $C_{102}S$ mutant exhibited an infectivity titer of 5.71 log 10 pfu/mL at 37° C. while no plaques (<0.7 log 10 pfu/mL) were detectable at 41° C., i.e., an efficiency of plaquing of >−5.0. However, the $C_{102}S$ mutant was not temperature sensitive at 39.5° C. and grew as well at this temperature as it did at 37° C.

Growth curves are conducted as described for the four cysteine mutants as well as wildtype virus in Vero cells (37° C. and 41° C.), Neuro2A cells (37° C.) and C6/36 cells (28° C.). Cells are grown in six-well plates in appropriate media and were infected with 200 uL virus diluted in PBS to a moi of 0.01. Adsorption is allowed to proceed for 30 minutes, and cells are washed three times with PBS. Appropriate media was added, and 0.5 mL samples were removed at 0, 12, 24, 48, 72, and 96 hours. Samples are then plaqued in Vero cells in twelve-well plates. Each growth curve is performed in triplicate, and each plaque assay was undertaken in duplicate.

Growth curves of wild-type and the four cysteine mutants at moi of 0.01 in Vero cells at both 37° C. and 41° C. are shown in FIG. 2A-B. Other than the $C_{102}S$ mutant, the cysteine mutants grew as well as wild-type virus at both 37° C. and 41° C. Although the $C_{102}S$ mutant grew comparably to wild-type virus at 37° C. (FIG. 2A), infectivity titers were found to peak approximately 5 log 10 lower than wild-type at 41° C. (FIG. 2B). Growth curves were also conducted in mouse neuroblastoma Neuro2A cells (FIG. 2C) and mosquito C6/36 cells (FIG. 2D). Recombinant viruses containing $C_{102}S$, $C_{120}S$, $C_{227}S$, and $C_{237}S$ substitutions multiplied at levels comparable to wild-type in both cell lines.

Example 3

In Vivo Virulence of Mutant Viruses

Recombinant viruses are diluted in PBS to obtain doses ranging from $10^3$ pfu to $10^{-1}$ pfu. 100 µL of each virus dose is injected intraperitoneally into groups of five 3-4 week old female NIH Swiss mice (methods also described in Beasley et al., 2002). Clinical signs of infection are recorded for the following 14 days, and LD50 values are calculated for the various viruses. Three weeks following inoculation, surviving mice are challenged with a uniformly lethal dose (100 pfu) of wild-type NY-99 WNV to determine if mice had induced a protective immune response. If a virus is found to be attenuated via the IP route, it is administered by the intracerebral (IC) route to investigate the mouse neurovirulence phenotype.

The $C_{120}S$, $C_{227}S$, and $C_{237}S$ mutants are as virulent as wild-type WNV following intraperitoneal inoculation in terms of lethality and average survival time (Table 2). In contrast, the $C_{102}S$ mutant is attenuated when inoculated by the intraperitoneal route with no mice showing clinical signs of infection following an inoculum of 10,000 pfu. Subsequent studies showed that the $C_{102}S$ mutant is also attenuated for neurovirulence. The $C_{102}S$ mutant fails to kill any mice at an inoculum of 1000 pfu whereas wild-type recombinant WNV had a LD50 value of 0.2 pfu resulting in at least 5,000-fold attenuation. While the $C_{102}S$ mutant is highly attenuated, it is still capable of inducing a protective immune response with an IP PD50 value of 0.4 pfu.

To determine where the block in viral replication occurs with respect to the $C_{102}S$ virus at 41° C., intracellular viral RNA and protein levels are assayed in Vero cells at both 37° C. and 41° C. Quantitative real-time RT-PCR results indicate comparable levels of viral RNA synthesis for both wild-type and $C_{102}S$ viruses in Vero cells at 37° C. (FIG. 3A). In contrast, there is a sharp reduction in synthesis of viral RNA levels in $C_{102}S$ virus-infected cells compared to wild-type virus-infected cells at 41° C. (FIG. 3B). Unexpectedly, initial intracellular RNA levels for the $C_{102}S$ virus-infected cells appear significantly higher than infectivity viral titers would indicate. This is attributed to the presence of non-infectious viral particles in the inoculum as the lower infectivity titer of $C_{102}S$ virus requires a lower dilution of $C_{102}S$ virus culture than wild-type virus culture to give a moi of 0.01. Viral protein levels are measured by Western blot utilizing an anti-WNV EDIII antibody to probe cell lysates generated from virus-infected Vero cells. Viral protein levels for both wild-type and $C_{102}S$ virus-infected cells are comparable at 37° C. (FIG. 3C), while viral protein is sharply reduced in $C_{102}S$ virus-infected cells compared to wild-type virus-infected cells at 41° C. (FIG. 3D). β-actin is used as an internal standard, and levels are similar in all samples (FIG. 3C-D, lower panel).

TABLE 2

| Virus | i.p. LD$_{50}$ (PFU) | i.p. AST (days ± SD) | i.p. PD$_{50}$ (PFU) | i.c. LD$_{50}$ (PFU) | i.c. PD$_{50}$ (PFU) | 37° C. Log$_{10}$ PFU | 41° C. Log$_{10}$ PFU | Efficiency of plaquing (41° C./37° C.) |
|---|---|---|---|---|---|---|---|---|
| NY99  | 0.5    | 7.4 ± 0.9 | n.d. | 0.2    | n.d. | 6.5 | 6.7  | 0.2  |
| C102S | >10,000 | >35      | 0.4  | >1,000 | 1.2  | 5.9 | <0.7 | >-5.2 |
| C120S | 0.7    | 8.0 ± 1.0 | n.d. | n.d.   | n.d. | 5.4 | 5.2  | -0.2 |
| C227S | 2.0    | 9.4 ± 2.4 | n.d. | n.d.   | n.d. | 5.9 | 5.5  | -0.4 |
| C237S | 5.0    | 8.6 ± 1.1 | n.d. | n.d.   | n.d. | 5.2 | 5.3  | 0.1  |

Example 4

Reversion of Temperature Sensitive Viruses

To generate temperature sensitive revertants, growth curve samples harvested at the 48 hour time point from either 37° or 41° C. were tested for the presence of revertants by picking plaques at 41° C., amplifying in Vero cells at 37° C., and determining the efficiency of plaquing at 37° C. versus 41° C. Plaque picks were identified that had a reversion of $S_{102}C$ and displayed neuroinvasiveness and neurovirulence characteristics similar to wild-type WNV.

Example 5

Protein and RNA Levels in Mutant Virus Infected Cells

Total viral and cellular RNA is isolated from Vero cell cultures at 0, 12, 24, and 48 hour time points using the Qiagen RNeasy Mini kit. A~100-bp fragment of the 3' noncoding region is amplified using TaqMan one-step RT-PCR as described by Beasley et al. 2005. To determine protein levels, cell lysates are generated by solubilizing virus- or mock-infected monolayers in RIPA buffer supplemented with 10% SDS. Lysates are run on an 12.5% SDS-PAGE gel and transferred to a PVDF membrane in duplicate. One membrane is probed with rabbit polyclonal anti-WNV envelope domain III antibody to determine viral protein levels, while the other membrane is probed with mouse anti-B actin antibody (Sigma) to assay cellular protein levels.

Example 6

Recover of WNV NS1 Mutant Viruses

A cDNA infectious clone designed from WNV NY99 (382-99) (SEQ ID NO: 1) is used for these experiments (Beasley et al., 2005). Briefly, the clone consists of a two plasmid system containing the 5' noncoding region, the structural genes and up to the NgoMIV site of the NS1 protein in one plasmid and the NgoMIV site of the NS1 through the 3' noncoding region in the second. An XbaI site is engineered after the NgoMIV site of the 5' plasmid and at the end of the 3'noncoding region (NCR) for the second plasmid. The vector plasmid is a modified pBr322 to remove the tetracycline gene and contains a T7 promotor upstream of the 5' noncoding region.

The glycosylation mutants are derived using site-directed mutagenesis (Stratagene QuikchangeII XL). In the case of the NS1 mutants, the 3' plasmid was used to change the asparagine to an alanine for $NS1_{130}$, $NS1_{175}$, and $NS1_{207}$ (5'-CCAGAACTCGCCGCCAACACCTTTGTGG (SEQ ID NO: 20), 5'-GGTCAGAGAGAGCGCCACAACTGAATGTGACTCG (SEQ ID NO: 21), 5'-GGATTGAAAGCAGGCTCGCTGATACGTGGAAGC (SEQ ID NO: 22), respectively). Clones are derived that included each of the NS1 mutations alone or in all possible combinations (Table 3). Since it is necessary to incorporate each of the mutations separately, $NS1_{130}$ mutant is used as a template to add the $NS1_{175}$ mutation, and this is used as a template to add the third mutation at $NS1_{207}$. Similarly, this technique is used in the generation of the other mutant combinations.

Since this is a two-plasmid system infectious clone system, in vitro ligation is necessary before transcription. The two plasmids are prepared for ligation by cutting approximately 1 µg of DNA from the 5' and 3' plasmid with NgoMIV and XbaI. This linearizes the 5' vector plasmid and leaves only the NS1 through 3' NCR of the 3' plasmid. Following restriction enzyme digestion, the DNA is run on a 1% TAE gel containing no DNA stain. A small portion of the well lane is cut after electrophoresis and placed in ethidium bromide. The band of interest is cut from this stained sample and realigned with the rest of the gel. The remaining band is excised from the unstained gel and purified using the QiAquik Gel Purification kit (Qiagen) according to the manufacturer's instructions. The purified DNA fragments are ligated using T4 DNA ligase (NEB) overnight at 4° C., heat inactivated for 10 minutes at 70° C. followed by XbaI linearization. The ligation mixture is treated with 100 µg proteinase K for 1 hour at 37°, followed by two phenol/chloroform/isoamyl alcohol extractions and one chloroform extraction before ethanol precipitation. The pelleted DNA is rehydrated in 10 µl of TE buffer pH 8.0 (Invitrogen) and used as a template for transcription incorporating an A cap analog (NEB) using the Ampliscribe T7 transcription kit (Epicentre). The reactions are placed at 37° C. for two hours at which time 2 µl is run on in agarose gel to ensure that transcription has taken place. Concurrently, 3.3× $10^6$ Vero cells were prepared in 500 µl of phosphate buffered saline (PBS-Gibco). The remaining transcription reaction is mixed with cells, placed in a 2 cm electrode gap cuvette (Bio-RAD), and pulsed twice at 1.5 volts, 25 µF, and ∞ ohms using a Gene Pulser (Bio-RAD). The cells are then left at room temperature for 10 minutes before adding to 35 ml of minimal essential medium (MEM-Gibco) supplemented with 8% bovine growth serum (BGS-Hyclone), 2% penicillin/streptomycin (Gibco), 2% non essential amino acids (Sigma), and 2% L-glutamine (Gibco) in a T75 $cm^2$ tissue culture flask and incubated at 37° C. The virus is harvested 4-5 days post infection when cytopathic effects (CPE) are apparent. The cell debris is pelleted by centrifugation before collection of the supernatant and 1 ml aliquots are frozen at −80° C. RNA is extracted (Qiagen Viral RNAmini kit) from a sample of each mutant virus and amplified using RT-PCR (Roche Titan One Step kit) and sequenced around the mutated region for verification of the mutation(s).

A total of 7 mutants are generated, via the methods described above (see Table 3) and are rescued as virus by transfecting cells with RNA as described in Materials and Methods. Four to five days post-transfection, each virus is harvested and infectivity titer is determined by plaque titration in Vero cells at 37° C. All the viruses used in subsequent experiments are derived from the transfection supernatant except for $NS1_{207}$, which is passaged once in Vero cells after transfection to gain a higher infectivity titer. Neither parental NY99 strain nor any of the mutant viruses derived from it are temperature sensitive at 39.5° and the plaque morphology of the mutants were not statistically smaller than NY99.

All mutant viruses are sequenced following amplification by RT-PCR to verify the engineered site mutation(s). The genomes of two attenuated viruses, $NS1_{130/207}$ and $NS1_{130/175/207}$ are completely sequenced via RT-PCR to determine if any changes resulted from the mutagenesis or transfection process. Full-length consensus sequence of the entire genome except the first 50 bases of the 5'NCR and last 50 bases of the 3' noncoding region are analyzed. The $NS1_{130/207}$ mutant contains one nucleotide change in NS5 at nucleotide 10221 which does not result in an amino acid change while the other attenuated virus ($NS1_{130/175/207}$) has no nucleotide substitution other than those engineered compared to the cDNA infectious NY99 clone.

TABLE: 3

| Virus | $NS1_{130}$ ASN→ALA | $NS1_{175}$ ASN→ALA | $NS1_{207}$ ASN→ALA |
|---|---|---|---|
| $NS1_{130}$ | X | | |
| $NS1_{175}$ | | X | |
| $NS1_{207}$ | | | X |
| $NS1_{130/175}$ | X | X | |
| $NS1_{175/207}$ | | X | X |
| $NS1_{130/207}$ | X | | X |
| $NS1_{130/175/207}$ | X | X | X |

Example 7

Characterization of NS1 Mutations

Tissue culture petri dishes containing a confluent monolayer of Vero cells are inoculated with mutant virus or parental strain virus and left to adsorb for 30 minutes. The virus inoculum is aspirated and the cells washed twice with PBS before adding 10 ml of MEM with 2% BGS supplemented as above. The plates are incubated at 37° C. and harvested at two days post infection. The plates are washed twice with PBS and then the cells are scraped from the plate before adding RIPA lysis buffer (Eliceiri 1998). This solution is then homogenized and centrifuged lysates are transferred to a fresh tube. Supernatant is also collected and prepared by reducing the 10 ml volume to 250 µl using Amicon 10 kd filter and adding the same volume of RIPA lysis buffer. The lysates and supernatants are then used for western blotting with a transblot (BioRad) according to manufacturer's instructions following the addition of Laemmli loading dye with out reducing agent.

Western blot analysis of lysates collected from infected Vero cells is used to determine the apparent molecular weight of the NS1 protein. An anti-NS1 monoclonal antibody (8 NS1) is used to probe the parental and deglycosylated $NS1_{130}$, $NS1_{175}$, $NS1_{207}$ viruses. Boiling of the samples in the absence of reducing agent reveals the dimeric and monomeric states of this protein. It is evident from the Western blot that the NS1 protein of all three glycosylation mutants migrate faster than the parental strain and that the parental strain has an apparent molecular weight of 37 kD. Analysis of these three glycosylation mutants on a 10% gel also shows that $NS1_{130}$ migrates faster than the other two glycosylation mutants ($NS1_{175}$, $NS1_{207}$) suggesting that WNV glycosylation sites contain one complex type sugar at $NS1_{130}$ and two high mannose type sugars at $NS1_{175}$ and $NS1_{207}$ (FIG. 4A). Also, a panel of 22 anti-NS1 monoclonal antibodies generated against WNV is used to probe $NS1_{130}$, $NS1_{175}$, $NS1_{207}$ and $NS1_{130/175/207}$ virus infected cell lysates. Each of the antibodies recognizes the NS1 protein from these four viruses suggesting that the conformation of this protein is not altered by the ablation of the glycosylation sites.

NS1 is a secreted protein and therefore Western blot analysis is used to determine if the deglycosylated NS1 proteins are still being secreted. Vero cells are infected with the mutants and supernatants are collected at 48 hours post infection. These supernatants are concentrated and the proteins run on a 10% non-reducing gel (FIG. 4B). All seven glycosylation mutant samples and the parental strain are recognized by the anti-NS1 monoclonal antibody 4NS1, indicating that nonglycosylated NS1 is indeed secreted.

Example 8

Localization of NS1 Mutant Protein

NS1 protein is visualized in vitro by infecting Vero and P388 cells with either parental strain, $NS1_{130/207}$ or $NS1_{130/175/207}$. 12 mm circular glass cover slips are infected at an m.o.i. of either 1 or 10 for Vero and 1 for P388 cells. The virus is left to adsorb for 45 minutes then the inoculum removed and the cells washed once with PBS. Maintenance media is added and the cells left at 37° C. for 48 hours at which time the media is removed and the cover slips fixed in a 1:1 acetone/methanol solution for 20 minutes. The cover slips are dried and placed at −20 overnight before probing. An anti NS1 monoclonal antibody culture supernatant is used undiluted and placed on the cover slips for 30 minutes at 37° C. Then the cover slips are washed 3 times in PBS for five minutes followed by the addition of the secondary alexoflour anti mouse antibody (Invitrogen) for 30 minutes at room temperature. After another three PBS washes, then drying dapi is added with mounting media (Prolong gold antifade-Invitrogen). The stained cells are visualized by confocal microscopy using the same gain for each of the slides.

Results of these experiments show that nonglycosylated NS1 attenuated mutant virus shows perinuclear localization while the parental strain shows a more diffuse pattern with NS1 protein seen from outside the nucleus to the cell membrane. Like other studies of nonglycosylated NS1 flaviviruses, these sugar residues seem to facilitate the release of the protein from the perinuclear region and therefore may result in a reduced secretion from the cell (Crabtree 2005). P388 cells shows a similar phenotype in that the parental strain fluorescence showed a much denser staining than that of the nonglycosylated NS1 mutant.

Example 9

Replication NS1 Mutant Virus in Cell Culture

Analysis of the replication kinetics in vitro includes growth curves in monkey kidney Vero and mouse macrophage P388 cells. Virus is added to a confluent monolayer of cells at m.o.i. of 0.1 and left to adsorb for 45 minutes at room temperature. Viral supernatant is aspirated and maintenance media containing 2% serum is added. Triplicate monolayers are infected for each virus and samples are collected at 12, 24, 36, 48, 60, 72 and 96 hours post-infection, centrifuged to pellet cell debris, and frozen at −80° C. until analyzed by plaque titration in Vero cells. When performing the plaque titration, the virus is left to adsorb for 45 minutes at room temperature before adding the agarose/media mixture.

Infectivity of each virus is measured by plaque titration using 6-well tissue culture plates (Costar-3506) containing a confluent Vero cell monolayer. The virus is added to the cells in ten-fold dilutions and left at room temperature for 30 minutes, rocking the plates every 5 minutes. After this time, 4 ml of 2% agarose/MEM overlay is added to the cells and the plates are placed at 37° C., or 39.5° C. for temperature sensitivity assays. Two days later, a second overlay containing 2.4% neutral red was added. Plaques are visualized over the next two days.

Growth curves of the two most attenuated ($NS1_{130/207}$ and $NS1_{130/175/207}$) mutant and parental NY99 viruses are compared in monkey kidney Vero, mouse macrophage-like P388 and mosquito C6/36 cells infected at a moi of 0.1. The student t-test is used to determine the statistical significant difference of samples from each of the time points. No significant differences in the multiplication of the mutant and parental viruses were seen in Vero cells (FIG. 5A) while the growth curves in P388 cells exhibits a small difference in infectivity titer with two attenuated viruses having a statistically lower infectivity titer compared to the parental strain at the 12 and 48 hour time points (FIG. 5B). C6/36 cells, however, show differences at each time point until 144 hours post-infection when the parental strain and two attenuated glycosylation mutants show similar infectivity titer (FIG. 5C). This is consistent with a previous study which found no differences in growth of nonglycosylated NS1 mutant viruses in mammalian cells but significant difference in C6/36 cells (Crabtree 2005).

Example 10

In Vivo Virulence of NS1 Mutant Virus

To study replication kinetics, groups of mice are inoculated ip with 100 pfu of either $NS1_{130/207}$, $NS1_{130/175/207}$, or NY99. Three mice are sacrificed each day post infection for six days, and brains and blood are collected. Blood samples are stored at 4° C. overnight, then centrifuged before collecting the serum and storing at −80° C. Each brain is resuspended 500 µl of 2% MEM and frozen at −80° C. All samples are plaque titrated in Vero cells.

To determine the mouse virulence phenotype of the mutant viruses, 3-4 week old female NIH Swiss (Harlan Sprague-Dawley) mice are examined for neuroinvasiveness and neurovirulence following intraperitoneal (ip) and intracerebral (ic) inoculation of virus, respectively. Serial 10-fold concentrations of virus are inoculated into groups of five mice. The parental NY99 strain derived from the infectious clone is used as a positive control in each experiment and PBS was used as a negative control. Mice are observed for 21 days and 50% lethal dose was calculated.

The mouse neuroinvasive phenotype is examined following intraperitoneal inoculation of 3-4 week old mice. Two of the mutants, $NS1_{130/207}$ and $NS1_{130/175/207}$, show a >1000-fold attenuation compared to parental NY99 strain and the other mutant viruses (Table 4). The attenuation of these two viruses was confirmed by two additional experiments. Mouse neurovirulence is determined following intracerebral inoculation and the $NS1_{130/207}$ mutant displayed a >50-fold attenuation while the $NS1_{130/175/207}$ mutant shows >100-fold attenuation.

TABLE: 4

| Virus | Pfu/LD$_{50}$ ip | AST + SD | p-Value* | Pfu/LD$_{50}$ ic |
|---|---|---|---|---|
| NY99 | 0.1 | 8.5 ± 2.0 | NA | 0.3 |
| NS1$_{130}$ | 2 | 10.0 ± 2.0 | <0.5 | ~ |
| NS1$_{175}$ | 50 | 10.4 ± 1.4 | <0.5 | ~ |
| NS1$_{207}$ | 1.3 | 8.0 ± 0.7 | >0.5 | ~ |
| NS1$_{130/175}$ | 80 | 9.7 ± 1.0 | >0.5 | ~ |
| NS1$_{130/207}$ | 320 | 9.6 ± 1.5 | >0.5 | 25 |
| NS1$_{175/207}$ | 20 | 8.8 ± 1.5 | >0.5 | ~ |
| NS1$_{130/175/207}$ | 5000 | 8.8 ± 1.5 | >0.5 | 80 |

Since some mice succumb to infection, the full-length genomic consensus sequence was also determined for a virus isolated from found the brain of a mouse that succumbed to infection following inoculation with the $NS1_{130/175/207}$ mutant at a dose of 1000 pfu by the ip route. This virus is found to have reversion at the $NS1_{130}$ site back to an asparagine and also two additional amino acid mutations at E-M203V and E-E236G. This "revertant" virus is used to inoculate a new group of mice and was found to have a virulent phenotype with <0.1 pfu/LD50. The mutations at E203 and E236 are put into the NY99 infectious clone alone and virus is generated. Mice infected with these viruses show a LD50 of 20 PFU for the E203 mutant and a LD50 of 2 PFU for the E236 mutant. However, some mice die at a dose of 0.1 PFU, which may account for the increase of neurovirulence seen in the original virus isolated from the brain.

Examination of the multiplication of the $NS1_{130/207}$ and $NS1_{130/175/207}$ mutant viruses and parental WNV in mice revealed that virus from all three strains was cleared from the serum after the third day post infection (FIG. 6A). The attenuated strains containing the mutations at $NS1_{130/207}$ and $NS1_{130/175/207}$ also show a decrease and slight delay in the onset of peak viremia when compared to parental NY99 virus. Not surprisingly, NY99 virus appears in the brain by the fifth day post-infection whereas neither of the two attenuated virus mutants examined show any detectable virus in the brain at any time post-infection (FIG. 6B).

In an effort to investigate a possible correlation of viremia with mortality of the animals, groups of 5 mice are inoculated with one of the two attenuated mutants, $NS1_{130/207}$ or $NS1_{130/175/207}$ with either 1000 or 100 pfu in order to achieve groups of mice that either succumb to or survive infection. Similarly, mice are inoculated with either 100 or 10 pfu of NY99 virus for the same reason. Mice are bled days 2 and 3 post-infection to measure viremia. Moribund animals are euthanized and brains are harvested and homogenized before passaging once in Vero cells for isolation and sequencing of the virus. Concurrently the brains of mice that die are also collected. The viremia is significantly reduced in the mice infected by either of the two attenuated viruses compared to those of the parental strain on either day 2 or day 3 post-infection (Table 5). The $NS1_{130/175/207}$ mutant with the higher LD50 value than the $NS1_{130/207}$ mutant had the greatest reduction in infectious virus. In the case of the parental NY99 strain only one mouse showed no detectable viremia and did not succumb to infection, however this mouse did not survive challenge. For the $NS1_{130/207}$ groups of mice, only two mice survive infection at an inoculum of either 100 or 1000 pfu. One of the surviving mice had a viremia of 3500 pfu/ml on day three, which is higher than most mice that succumbed to infection in this group; however the mouse exhibited encephalitic manifestations by partial paralysis and survived challenge. All other mice infected with $NS1_{130/207}$ show a viremia in the 100 to 1000 pfu/ml range. In the case of the $NS1_{130/175/207}$ group, two animals with a viremia greater than 1000 pfu/ml of virus died. Another mouse succumbed to infection without detectable viremia. However, the virus isolated from the brain of this mouse showed a reversion back to asparagine at the $NS1_{130}$ site. All other surviving mice showed a peak viremia of less than 100 pfu.

TABLE: 5

| Mouse | NY99 (10 pfu) | | $NS1_{130/207}$ (100 pfu) | | $NS1_{130/175/207}$ (100 pfu) | |
|---|---|---|---|---|---|---|
| | Day 2 | Day 3 | Day 2 | Day 3 | Day 2 | Day 3 |
| 1 | <50 | 15000* | 50 | 600* | <50 | <50 |
| 2 | <50 | <50 | <50 | <50 | <50 | <50*R |
| 3 | 2000 | 150000* | 1000 | 5000* | <50 | <50 |
| 4 | 4000 | 50000* | 2000 | 5000* | <50 | <50 |
| 5 | 2500 | 300000* | 50 | 200* | <50 | <50 |

TABLE: 5-continued

| Mouse | NY99 (100 pfu) | | $NS1_{130/207}$ (1000 pfu) | | $NS1_{130/175/207}$ (1000 pfu) | |
|---|---|---|---|---|---|---|
| | Day 2 | Day 3 | Day 2 | Day 3 | Day 2 | Day 3 |
| 1 | 5000 | 2000* | 1500 | 600* | 50 | <50 |
| 2 | 6500 | 3000* | 100 | 3500[1] | 100 | 100 |
| 3 | 10000 | 5000* | 100 | 1100* | <50 | <50 |
| 4 | 4000 | 10000* | 500 | 600* | 50 | 4500*R |
| 5 | <50 | 12500* | 250 | 1000* | 400 | 1500*R |

Example 11

Multiple Mutations in an NS1 Glycosylation Motif

Given the propensity for reversion of NS1 mutant viruses in may be advantageous to mutate multiple amino acid residues in a glycosylation-motif. Additional point mutations are introduced into NS1 mutant viruses by methods outlined in the previous examples. Mutations of the nucleic acid sequences results in corresponding amino acid mutations that are listed in Table 6. The other two glycosylation motifs in WNV NS1 (i.e., surrounding positions 175 and 207) may also be mutated. For instance, $NS1_{176}$ may be mutated from Thr to Gln, $NS1_{177}$ may be mutated from Thr to Ala, $NS1_{208}$ may be mutated from Asp to Gln and/or $NS1_{209}$ may be mutated from Thr to Ala.

TABLE: 6

| Virus | $NS1_{130}$ | $NS1_{131}$ | $NS1_{132}$ |
|---|---|---|---|
| NY-99 | Asn | Asn | Thr |
| $NS1_{130}$ | Ala | Asn | Thr |
| $NS1_{130S}$ | Ser | Val | Thr |
| $NS1_{130Q}$ | Gln | Gln | Ala |

Mutant viruses are generated by transfection of nucleic acid into permissive cells as previously described. The in vitro replication kinetics of the mutant viruses are measured in P388 (FIG. 7A) and Neuro2A (FIG. 7B) tissue culture. These studies indicate that each of the mutant viruses is capable of tissue culture replication. However, the NS1 mutant viruses replicate less efficiently than wild type NY99 in both P388 and Neuro2A cells. This effect is most prominent in the $NS1_{130S/175/207}$ virus.

To test the neuroinvasiveness and neurovirulence of the NS1 mutant viruses mice are inoculated either ip or ic with wild type or NS1 mutant viruses to determine the lethal dose 50. The results of the studies are presented in Table 7. These in vivo studies indicate that additional mutation of the glycosylation motif in NS1 results in at least 10-fold increase in $LD_{50}$ (compare results with the $NS1_{130/175/207}$ to results with the $NS1_{130S/175/207}$ or $NS1_{130Q/175/207}$ viruses). Thus, the studies indicate that mutation at multiple amino acid positions in a glycosylation motif may be used to generate highly attenuated flaviviruses with reduced risk of reversion.

TABLE: 7

| Virus | $ipLD_{50}$ | $icLD_{50}$ |
|---|---|---|
| NY-99 | 13 | 13 |
| $NS1_{130/175/207}$ | 1,300 | 20 |
| $NS1_{130S}$ | 316 | >100 |
| $NS1_{130Q}$ | 500 | 500 |
| $NS1_{130S/175/207}$ | 80,000 | 500 |
| $NS1_{130Q/175/207}$ | >1,000,000 | 800 |

Example 12

NS1/E Combination Mutants

Vaccine viruses may optimally comprise attenuating mutations at multiple positions in the viral genome. Such mutations further reduce the risk that vaccine virus will revert to a virulent phenotype via mutagenesis. To this end, studies are performed to test the attenuation phenotypes of viruses comprising NS1 mutations along with mutations in the WNV E protein. A mutation is introduced into NS1 mutant viruses that changes $E_{154}$ from Asn to Ser as previous described by Beasley et al. (2005). These viruses are tested in tissue culture replication assays to determine their in vitro replication kinetics. Results from these studies indicate that NS1 mutant viruses additionally comprising the $E_{154}$ mutation replicate similarly to viruses comprising the NS1 mutations alone (FIGS. 7A and B) and less efficiently than wild type WNV NY99 (FIG. 7A-D).

In order to further investigate the attenuation phenotype of these E/NS1 mutant viruses, neuroinvasiveness and neurovirulence is examined in a mouse model. The indicated virus is administered as previous described and the lethal dose 50 is determined. Results from these studies are shown in Table 8. All of the mutant viruses that are tested are at least 10,000 fold less neuroinvasive and nearly 1,000 fold less neurovirulent than wild type virus. These data demonstrate that viruses comprising NS1 and E protein mutations, such as glycosylation abrogating mutations, are highly attenuated and ideal vaccine candidates.

TABLE: 8

| Virus | ipLD$_{50}$ | icLD$_{50}$ |
|---|---|---|
| NY-99 | 0.1 | 0.1 |
| $E_{154}$/NS1$_{130/175/207}$ | >100,000 | 100 |
| $E_{154}$/NS1$_{130S/175/207}$ | >100,000 | 126 |
| $E_{154}$/NS1$_{130Q/175/207}$ | >1,000 | <100 |

Example 13

Analysis of Additional Mutations in NS4B

The effect of additional NS4B mutations on WNV is studied. Methods previously described are used to generate WNV viruses comprising point mutations in the NS4B coding region. Mutations are made based upon homology with other viruses in the amino-terminal region ($D_{35}E$, $P_{38}G$, $W_{42}F$, $Y_{45}F$) or to match mutations found in passage adapted dengue, YF or JE viruses ($L_{108}P$, $L_{97}M$, $A_{100}V$ and $T_{116}I$), see FIG. 1 for reference. Viruses comprising the foregoing mutations are assayed for a temperature sensitive phenotype in tissue culture replication as previously described. Results of these studies, shown in Table 9, indicate that a WNV comprising both a $P_{38}G$ and $T_{116}I$ substitution displays a significant temperature sensitivity (all values indicate $\log_{10}$ PFU/ml, n.d. indicates that the value is not determined).

TABLE: 9

| Virus | Temperature | | | EOP* |
|---|---|---|---|---|
| | 37° C. | 39.5° C. | 41° C. | |
| $D_{35}E$ | 5.7 | n.d. | 5.4 | −0.3 |
| $P_{38}G/T_{116}I$ | 6.2 | 5.8 | 3.0 | −3.2 |
| $W_{42}F$ | 6.7 | n.d. | 6.5 | −0.2 |
| $Y_{45}F$ | 5.5 | n.d. | 5.8 | 0.3 |
| $L_{97}M$ | 6.5 | n.d. | 6.8 | 0.3 |
| $L_{108}P$ | 6.8 | n.d. | 7.0 | 0.2 |
| $A_{100}V$ | 7.0 | n.d. | 6.7 | −0.3 |
| $T_{116}I$ | 6.9 | n.d. | 7.0 | 0.1 |
| Wt | 6.5 | 6.4 | 6.7 | 0.2 |

*indicates change in log10 PFU/ml 37° C. versus 41° C.

Replication kinetics for these mutant viruses are further examined in a variety of tissue culture cells. For the viruses comprising the $L_{108}P$, $L_{97}M$ or $A_{100}V$ substitutions no change in viral replication kinetics is apparent. In confirmation of the studies shown in Table 9, the $P_{38}G/T_{116}I$ virus has significantly slower replication kinetics than wild type WNV when grown in Vero cells at 41° C. However, this virus mutant grows normally in Vero cells at 37° C. (FIG. 8A). Additionally, even under restrictive temperature conditions (i.e., at 41° C.) 96 hours post-infection the amount of $P_{38}G/T_{116}I$ virus in the tissue culture media is similar to that of wild type virus (FIG. 8B).

The neuroinvasiveness and neurovirulance of NS4B mutant viruses is determined in mice as previously described. Results of these studies are shown in Table 10. Significantly, the $P_{38}G/T_{116}I$ mutant virus is over 10,000 fold less neuroinvasive than wild type virus, however no change in neurovirulence is exhibited.

TABLE: 10

| Virus | ipLD$_{50}$ | icLD$_{50}$ | ip AST* |
|---|---|---|---|
| $D_{35}E$ | 0.4 | n.d. | 7.2 ± 0.9 |
| $P_{38}G/T_{116}I$ | >10,000 | <0.1 | N/A |
| $W_{42}F$ | <0.1 | n.d. | 7.4 ± 0.9 |
| $Y_{45}F$ | <0.1 | <0.1 | 7.4 ± 0.9 |
| $L_{97}M$ | 0.4 | n.d. | 7.6 ± 1.0 |
| $L_{108}P$ | <0.1 | n.d. | 7.6 ± 1.5 |
| $A_{100}V$ | <0.1 | n.d. | 7.8 ± 2.4 |
| $T_{116}I$ | 0.5 | n.d. | 8.0 ± 1.8 |
| Wt | 0.5 | <0.1 | 7.4 ± 0.9 |

*indicates average survival time for after ip administration.

Given the substantial attenuation exhibited by the $P_{38}G/T_{116}I$ virus, this virus is used to inoculate mice prior to challenge with wild type WNV. Mice are inoculated with the $P_{38}G/T_{116}I$ virus and then challenged with 100 LD$_{50}$ of wild type WNV via ip route. Results of this study show that the $P_{38}G/T_{116}I$ virus has a protective dose 50 (PD$_{50}$) 0.3 PFU under assay conditions. Thus, flaviviruses comprising the $P_{38}G/T_{116}I$ may be ideal vaccine candidates.

\* \* \*

All of the compositions and methods disclosed and claimed herein can be made and executed without undue experimentation in light of the present disclosure. While the compositions and methods of this invention have been described in terms of preferred embodiments, it will be apparent to those of skill in the ail that variations may be applied to the compositions and methods and in the steps or in the sequence of steps of the method described herein without departing from the concept, spirit and scope of the invention.

More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,826,364
U.S. Pat. No. 3,949,064
U.S. Pat. No. 4,174,384
U.S. Pat. No. 4,284,412
U.S. Pat. No. 4,435,386
U.S. Pat. No. 4,436,727
U.S. Pat. No. 4,436,728
U.S. Pat. No. 4,498,766
U.S. Pat. No. 4,505,899
U.S. Pat. No. 4,505,900
U.S. Pat. No. 4,520,019
U.S. Pat. No. 4,554,101
U.S. Pat. No. 4,579,945
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,661,913
U.S. Pat. No. 4,714,682
U.S. Pat. No. 4,767,206
U.S. Pat. No. 4,774,189
U.S. Pat. No. 4,857,451
U.S. Pat. No. 4,866,034
U.S. Pat. No. 4,877,611
U.S. Pat. No. 4,950,645
U.S. Pat. No. 4,989,977
U.S. Pat. No. 5,160,974
U.S. Pat. No. 5,478,722
Azuma et al., *Cell Immunol.*, 116(1):123-134, 1988.
Beasley et al., *J. Virol.*, 79, 8339-47, 2005.
Beasley et al., *Virology*, 296:17-23, 2002.
Bernard et al., *AIDS*, 12(16):2125-39, 1998.
Blaney, Jr. et al., *Vaccine*, 21:4317-4327, 2003.
Blitvich et al., *Arch. Virol.*, 140:145-156, 1995.
Blitvich et al., *J. Gen. Virol.*, 82:2251-2256, 2001.
Blitvich et al., *Virus Research*, 60:67-79, 1999.
Campbell, In: *Monoclonal Antibody Technology, Laboratory Techniques in Biochemistry and Molecular Biology*, Burden and Von Knippenberg (Eds.), Elseview, Amsterdam, 75-83, 1984.
Chambers et al., *Ann. Rev. Microbiology*, 44,649-688, 1990.
Chambers et al., *Virology*, 169:100-109, 1989.
Chang et al., *J. Infectious Disease*, 186:743-51, 2002.
Crabtree et al., *Arch Virol.*, 150:771-786, 2005.
Crooks et al., *J. Virology*, 75:3453-3460, 1994.
Eliceiri et al., *J. Cell Biol.*, 140:1255-1263, 1988.
Falconar, *Arch. Virol.*, 142(5):897-916, 1997.
Falgout and Markoff, *J. Virology*, 69(11):7232-7243, 1995.
Flamand et al., *J. Virology*, 73:6104-6110, 1999.
Flamand et al., *Virology*, 191:826-836, 1992.
Freifelder, In: *Physical Biochemistry Applications to Biochemistry and Molecular Biology*, 2nd Ed. Wm. Freeman and Co., NY, 1982.
Gefter et al., *Somatic Cell Genet.*, 3:231-236, 1977.
Goding, In: *Monoclonal Antibodies: Principles and Practice*, 2d ed., Academic Press, Orlando, Fl, pp 65-66, 71-74, 1986.
Hahn et al., *Proc. Natl. Acad. Sci. USA*, 84:2019-2023, 1987.
Hall et al., *J. Gen. Virol.*, 77:287-1294, 1996.
Hall et al., *Virology*, 264:66-75, 1999.
Hanley et al, *Virology*, 312:222-232, 2003.
Husson et al, *J. Bacteriol.*, 172(2):519-524, 1990.
Jacobs et al., *J Virology*, 66(4):2086-2095, 1992.
Kohler and Milstein, *Nature*, 256:495-497, 1975.
Kyte and Doolittle, *J. Mol. Biol.*, 157(1):105-132, 1982.
Lidenbach and Rice, *Field Virology, fourth edition*, 991-1041, 2001.
Lindenbach and Rice, *J. Virology*, 91:9608-9617, 1997.
Lotte et al., *Adv. Tuberc. Res.*, 21:107-93; 194-245, 1984.
Luelmo, *Am. Rev. Respir. Dis.*, 125(3 Pt 2):70-72, 1982.
Lundin et al., *J. Virol.*, 77:5428-5438, 2003.
Mackenzie et al., *Virology*, 220:232-240, 1996.
Martin, *J. Biol. Chem.*, 265(34):20946-20951, 1990.
Mason, *Virology*, 169:354-364, 1989.
McArthur et al., *J. Virol.*, 77:1462-1468, 2003.
Monath et al., *Curr. Drug Targets Infect. Disord.*, 1:37-50, 2001.
Muylaert et al., *Virology*, 222:159-168, 1996.
Nestorowicz et al., *Virology*, 199:114-123, 1994.
Ni et al., *J. Gen. Virol.*, 76:409-413, 1995.
Nociari et al., *J Immunol Methods*, 213(2):157-67, 1998.
PCT Appln. WO 91/16347
Pletnev et al., *J. Virology*, 67(8):4956-4963, 1993.
Pletnev et al, *Proc. Natl. Acad. Sci. USA*, 99:3036-3041, 2002.
Post et al, *Virus Res.*, 18:291-302, 1991.
Preugschat and Strauss, *Virology*, 185:689-697, 1991.
Pryor and Wright, *J. Gen Virol.*, 75:1183-1187, 1994.
Pryor and Wright, *Virology*, 194:769-780, 1993.
Pryor et al., *J. Gen Virol.*, 79:2931-2639, 1998.
Rabinovich et al., *Science*, 265(5177):1401-1404, 1994.
Remington's Pharmaceutical Sciences, 18th Ed. Mack Printing Company, pp. 1289-1329, 1990.
Rosenthal, *Am. Rev. Tuber.* 35:678-684, 1937.
Sambrook et al., In: *Molecular cloning: a laboratory manual*, $2^{nd}$ Ed., Cold Spring Harbor Laboratory Press, Cold Spring Harbor, N.Y., 1987.
Sambrook et al., In: *Molecular cloning: a laboratory manual*, $2^{nd}$ Ed., Cold Spring Harbor Laboratory Press, Cold Spring Harbor, N.Y., 1989.
Schlesinger et al., *J. Gen Virol,* 71. 593-599, 1990.
Snapper et al., *Proc. Natl. Acad. Sci. USA*, 85(18):6987-6991, 1988.
Sumiyoshi et al., *Virology*, 161:497-510, 1987.
Takada et al., *Infection and Immunity*, 63(1):57-65, 1995.
Tong et al., *BBRC.*, 299:366-372, 2002.
Wang et al., *J. Gen. Virol.*, 76:2749-2755, 1995.
Westaway et al., *J. Virol.*, 71:6650-6661, 1997.
Westaway et al., *Virology*, 234:31-41, 1997.
Winkler et al., *Virology*, 162:187-196, 1988.
Winkler et al., *Virology*, 171:302-305, 1989.
Yamamoto et al., *Nature*, 334(6182):494-498, 1988.
Yin et al., *J. Biol. Resp. Modif,* 8:190-205, 1989.
Young, and Falconar, *Arbovirus Res. Australia*, 5:62-67, 1989.

The invention claimed is:

1. A nucleic acid molecule comprising a sequence encoding a mutant flaviviral NS4B protein of a Japanese encephalitis or dengue sero- and genetic group, the NS4B protein having a central region, and wherein said NS4B protein comprises a serine substitution at a cysteine residue in the central region that reduces the virulence of a virus encoding said NS4B protein, wherein said central region corresponds to amino acid positions 70-85 of the consensus sequence of SEQ ID NO: 19.

2. The nucleic acid molecule of claim 1, wherein said mutant flaviviral NS4B protein is a NS4B protein of a Dengue virus, Japanese encephalitis virus, Murray valley encephalitis virus, Kunjin virus, West Nile virus, Saint Louis encephalitis virus or Usutu virus, which NS4B protein comprises a serine substitution at a cysteine residue in the central region that reduces the virulence of a virus encoding said NS4B protein.

3. The nucleic acid molecule of claim 2, wherein said mutant flaviviral NS4B protein is a dengue virus type 1, 2, 3, or 4 NS4B protein.

4. The nucleic acid molecule of claim 2, wherein said amino acid substitution is at a position corresponding to amino acid 102 of the West Nile virus NS4B protein sequence of SEQ ID No: 16.

5. The nucleic acid molecule of claim 4, wherein said amino acid substitution is a cysteine to serine substitution at a position corresponding to amino acid 102 of the West Nile virus NS4B protein sequence of SEQ ID NO: 16.

6. The nucleic acid molecule of claim 1, further comprising an additional viral sequence.

7. The nucleic acid molecule of claim 6, wherein the additional viral sequence is a sequence encoding a flavivirus E protein.

8. The nucleic acid molecule of claim 7, wherein said Flavivirus E protein comprises a deletion or amino acid substitution at a site of N-linked glycosylation in the E protein.

9. The nucleic acid molecule of claim 8, further comprising a deletion or amino acid substitution at all sites of N-linked glycosylation in the E protein.

10. The nucleic acid molecule of claim 9, wherein said deletion or amino acid substitution is at a position corresponding to amino acid 444 of SEQ ID NO: 1.

11. The nucleic acid molecule of claim 10, where said amino acid substitution in the E protein is an asparagine to serine substitution.

12. The nucleic acid molecule of claim 6, wherein the additional viral sequence is a sequence encoding a flavivirus NS1 protein.

13. The nucleic acid molecule of claim 12, wherein said flavivirus NS1 protein comprises a deletion or amino acid substitution at a site of N-linked glycosylation of the NS1 protein.

14. The nucleic acid molecule of claim 13, wherein said amino acid substitution at a site of N-linked glycosylation of the NS1 protein comprises a substitution of two or more amino acid residues.

15. The nucleic acid molecule of claim 13, further comprising a deletion or amino acid substitution at all sites of N-linked glycosylation in the NS1 protein.

16. The nucleic acid molecule of claim 13, where said amino acid deletion or substitution abrogates glycosylation at an amino acid position corresponding to amino acid 921, 966 or 998 of SEQ ID NO: 1.

17. The nucleic acid molecule of claim 16, where said amino acid deletion or substitution abrogates glycosylation at an amino acid position corresponding to amino acid 921, 966 and 998 of SEQ ID NO: 1.

18. The nucleic acid molecule of claim 16, where said amino acid substitution is at an amino acid position corresponding to amino acid 921, 966 or 998 of SEQ ID NO: 1.

19. The nucleic acid molecule of claim 18, where said amino acid substitution is an asparagine to alanine substitution at an amino acid position corresponding to amino acid 921, 966 or 998 of SEQ ID NO: 1.

20. The nucleic acid molecule of claim 6, wherein the nucleic acid sequence is an infectious clone.

21. A chimeric virus comprising the infectious clone of claim 20.

22. The nucleic acid molecule of claim 1, wherein the nucleic acid is DNA.

23. The nucleic acid molecule of claim 1, wherein the nucleic acid is RNA.

24. A virus comprising the RNA nucleic acid molecule of claim 23.

* * * * *

UNITED STATES PATENT AND TRADEMARK OFFICE
CERTIFICATE OF CORRECTION

| | | |
|---|---|---|
| PATENT NO. | : 8,017,754 B2 | Page 1 of 1 |
| APPLICATION NO. | : 11/995920 | |
| DATED | : September 13, 2011 | |
| INVENTOR(S) | : Jason A. Wicker et al. | |

It is certified that error appears in the above-identified patent and that said Letters Patent is hereby corrected as shown below:

On the title page, item (75) Inventors, delete "Michael D. T. Barrett" and insert
--Alan D. T. Barrett-- therefor.

In column 1, lines 11-13, delete paragraph and insert
--This invention was made with government support under grant number T32AI 7526 awarded by the National Institutes of Health. The government has certain rights in the invention.-- therefor.

Signed and Sealed this

Thirteenth Day of December, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,017,754 B2 | Page 1 of 1 |
| APPLICATION NO. | : 11/995920 | |
| DATED | : September 13, 2011 | |
| INVENTOR(S) | : Wicker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 342 days.

Signed and Sealed this
Thirty-first Day of January, 2012

David J. Kappos
*Director of the United States Patent and Trademark Office*